United States Patent
Nazare et al.

(10) Patent No.: US 9,221,828 B2
(45) Date of Patent: Dec. 29, 2015

(54) N-[4-(1H-PYRAZOLO[3,4-B]PYRAZIN-6-YL)PHENYL]SULFONAMIDES AS PHARMACEUTICALS

(71) Applicant: SANOFI, Paris (FR)

(72) Inventors: Marc Nazare, Frankfurt am Main (DE); Nis Halland, Frankfurt am Main (DE); Friedemann Schmidt, Frankfurt am Main (DE); Tilo Weiss, Frankfurt am Main (DE); Uwe Dietz, Bad Soden (DE); Armin Hofmeister, Frankfurt am Main (DE); Jean-Christophe Carry, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/299,417

(22) Filed: Jun. 9, 2014

(65) Prior Publication Data
US 2014/0288083 A1    Sep. 25, 2014

Related U.S. Application Data

(63) Continuation of application No. 13/236,027, filed on Sep. 19, 2011, now abandoned.

(51) Int. Cl.
*A61K 31/4985* (2006.01)
*C07D 487/04* (2006.01)

(52) U.S. Cl.
CPC .................................. *C07D 487/04* (2013.01)

(58) Field of Classification Search
CPC .......................... A61K 31/4985; C07D 487/04
USPC ................ 514/250; 544/350; 546/200, 268.1; 548/373.1; 549/59, 355, 356
See application file for complete search history.

(56) References Cited

U.S. PATENT DOCUMENTS

| | | |
|---|---|---|
| 2005/0070542 A1 | 3/2005 | Hodgetts et al. |
| 2008/0167380 A1 | 7/2008 | Gericke et al. |
| 2010/0029653 A1 | 2/2010 | Schirok et al. |
| 2010/0063115 A1 | 3/2010 | Klein et al. |
| 2013/0072493 A1 | 3/2013 | Nazare et al. |

FOREIGN PATENT DOCUMENTS

| | | |
|---|---|---|
| DE | 102005015255 A1 | 10/2006 |
| DE | 102007002717 A1 | 7/2008 |
| WO | WO 03061130 A1 | 7/2003 |
| WO | WO 2006061130 A2 | 6/2006 |
| WO | WO 2013041119 A1 | 3/2013 |

OTHER PUBLICATIONS

Belaiba R.S. et al., "The Serum- and Glucocorticoid-Inducible Kinase Sgk-1 is Involved in Pulmonary Vascular Remodeling-Role in Redox-Sensitive Regulation of Tissue Factor by Thrombin", Circulation Research 98:828-836 (Mar. 31, 2006).

Bhargava A. et al., "The Serum- and Glucocorticoid-Induced Kinase is a Physiological Mediator of Aldosterone Action", Endocrinology 142(4):1587-1594 (2001).

Akutsu N. et al., "Regulation of Gene Expression by 1α,25-Dihydroxyvitamin D3 and its Analog EB1089 Under Growth-Inhibitory Conditions in Squamous Carcinoma Cells", Molecular Endocrinology 15(7):1127-1139 (2001).

Alliston T.N. et al., "Expression and Localization of Serum/Glucocorticoid-Induced Kinase in the Rat Ovary: Relation to Follicular Growth and Differentiation", Endocrinology 141(1):385-395 (2000).

Alliston T.N. et al., "Follicle Stimulating Hormone-Regulated Expression of Serum/Glucocorticoid-Inducible Kinase in Rat Ovarian Granulosa Cells: A Functional Role for the Sp1 Family in Promoter Activity", Molecular Endocrinology 1934-1949 (1997).

Alvarez De La Rosa D. et al., "Role of SGK in Hormonal Regulation of Epithelial Sodium Channel in A6 Cells", Am J Physiol Cell Physiol 284:C404-C414 (2003).

Alvarez De La Rosa D. et al., "The Serum and Glucocorticoid Kinase sgk Increases the Abundance of Epithelial Sodium Channels in the Plasma Membrane of Xenopus Oocytes", The Journal of Biological Chemistry 274 (53):37834-37839 (Dec. 1999).

Atsumi T. et al., "A Chondrogenic Cell Line Derived from a Differentiating Culture of AT805 Teratocarcinoma Cells", Cell Differentiation and Development 30:109-116 (1990).

(Continued)

*Primary Examiner* — Douglas M Willis
(74) *Attorney, Agent, or Firm* — Morrison & Foerster LLP

(57) ABSTRACT

The present invention relates to N-[4-(1H-pyrazolo[3,4-b]pyrazin-6-yl)-phenyl]-sulfonamides of the formula I,

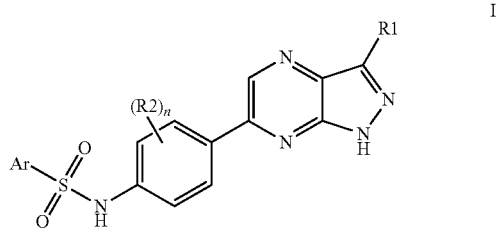

wherein Ar, R1, R2 and n have the meanings indicated in the claims. The compounds of the formula I are valuable pharmacologically active compounds which modulate protein kinase activity, specifically the activity of serum and glucocorticoid regulated kinase (SGK), in particular of serum and glucocorticoid regulated kinase isoform 1 (SGK-1, SGK1), and are suitable for the treatment of diseases in which SGK activity is inappropriate, for example degenerative joint disorders or inflammatory processes such as osteoarthritis or rheumatism. The invention furthermore relates to processes for the preparation of the compounds of the formula I, their use as pharmaceuticals, and pharmaceutical compositions comprising them.

17 Claims, No Drawings

(56) References Cited

OTHER PUBLICATIONS

Biondi R.M. et al., "The PIF-Binding Pocket in PDK1 is Essential for Activation of S6K and SGK, But Not PKB", The EMBO Journal 20(16):4380-4390 (2001).
Boehmer C. et al., "Properties and Regulation of Glutamine Transporter SN1 by Protein Kinases SGK and PKB", Biochemical and Biophysical Research Communications 306:156-163 (2003).
Boehmer C. et al., "Serum and Glucocorticoid Inducible Kinases in the Regulation of the Cardiac Sodium Channel SCN5A", Cardiovascular Research 57:1079-1084 (2003).
Böhmer C. et al., "The Shrinkage-Activated Na+ Conductance of Rat Hepatocytes and its Possible Correlation to rENaC", Cellular Physiology and Biochemistry 10:187-194 (2000).
Brennan F.E. et al., "Rapid Upregulation of Serum and Glucocorticoid-Regulated Kinase (sgk) Gene Expression by Corticosteroids In Vivo", Molecular and Cellular Endocrinology 166:129-136 (2000).
Camp D. et al., "Mechanism of the Mitsunobu Esterification Reaction. 1. The Involvement of Phosphoranes and Oxyphosphonium Salts", J. Org. Chem. 54:3045-3049 (1989).
Cecchi L. et al., "Reaction of 3-Phenyl-4,5-Diaminopyrazole With 1,2-Dioxocompounds: 3-Phenylpyrazolo[4,5-b] Pyrazines", II Farmaco Ed. Sc. 37(2):116-122 (1982).
Chan D.M.T. et al., "New N- and O-Arylations With Phenylboronic Acids and Cupric Acetate", Tetrahedron Letters 39:2933-2936 (1998).
Chien T-C et al., "Facile Synthesis of 1-Substituted 4,5-Diaminopyrazoles and its Application Toward the Synthesis of Pyrazolo[3,4-b]Pyrazines", Tetrahedron Letters 45:4105-4108(2004).
Colombo A. et al., "Synthesis of Pyrazolo[3,4-b][1,4]Diazepines and Pyrazolo[3,4-b]Pyrazines", J. Heterocyclic Chem. 26:949-955 (Jul.-Aug. 1989).
Cooper M.S. et al., "Modulation of 11B-Hydroxysteroid Dehydrogenase Isozymes by Proinflammatory Cytokines in Osteoblasts: An Autocrine Switch from Glucocorticoid Inactivation to Activation", Journal of Bone and Mineral Research 16(6):1037-1044 (2001).
Crich D. et al., "Some Observations on the Mechanism of the Mitsunobu Reaction", J. Org. Chem. 54:257-259 (1989).
Davies S.P. et al., "Specificity and Mechanism of Action of Some Commonly Used Protein Kinase Inhibitors", Biochem. J. 351:95-105 (2000).
Debonneville C. et al., "Phosphorylation of Nedd4-2 by Sgk1 Regulates Epithelial Na+ Channel Cell Surface Expression", The EMBO Journal 20(24):7052-7059 (2001).
Faletti C.J. et al., "Sgk: An Essential Convergence Point for Peptide and Steroid Hormone Regulation of ENaC-Mediated Na+ Transport", Am J Physiol Cell Physiol 282:C494-0500 (2002).
Feng Y. et al., "SGK1-Mediated Fibronectin Formation in Diabetic Nephropathy", Cellular Physiology and Biochemistry 16:237-244 (2005).
Filák L. et al., "A New Cyclization to Fused Pyrazoles Tunable for Pericyclic or Pseudopericyclic Route: An Experimental and Theoretical Study", J. Org. Chem. 73:3900-3906 (2008).
Fillon S. et al., "Expression of the Serine/Threonine Kinase hSGK1 in Chronic Viral Hepatitis", Cellular Physiology and Biochemistry 12:47-54 (2002).
Firestone G.L. et al., "Stimulus-Dependent Regulation of Serum and Glucocorticoid Inducible Protein Kinase (SGK) Transcription, Subcellular Localization and Enzymatic Activity", Cellular Physiology and Biochemistry 13:001-012 (2003).
Foks H. et al., "Synthesis and Antibacterial Activity of 1H-Pyrazolo[3,4-b]Pyrazine and -Pyridine Derivatives", II Farmaco 60:513-517 (2005).
Friedrich B. et al., "The Serine/Threonine Kinases SGK2 and SGK3 are Potent Stimulators of the Epithelial Na+ Channel $\alpha,\beta,\gamma$-ENaC", Eur J Physiol 445:693-696 (2003).
Funder J., "Mineralocorticoids and Cardiac Fibrosis: The Decade in Review", Clinical and Experimental Pharmacology and Physiology 28:1002-1006 (2001).
Gamper N. et al., "IGF-1 Up-Regulates K+ Channels Via PI3-Kinase, PDK1 and SGK1", Eur J Physiol 443:625-634 (2002).
Giori P. et al., "Reactivity of Pyrazolo[4,3-c][1,2,5]Oxadiazin-3(5H)-Ones Toward C-Nucleophiles: Synthesis of Pyrazolo[3,4-b]Pyrazines", J. Heterocyclic Chem. 23:585-588 (Mar.-Apr. 1986).
Gonzalez-Robayna I.J. et al., "Follicle-Stimulating Hormone (FSH) Stimulates Phosphorylation and Activation of Protein Kinase B (PKB/Akt) and Serum and Glucocorticoid-Induced Kinase (Sgk): Evidence for a Kinase-Independent Signaling by FSH in Granulosa Cells", Molecular Endocrinology 14(8):1283-1300 (2000).
Gonzalez-Robayna I.J. et al., "Functional and Subcellular Changes in the A-Kinase-Signaling Pathway: Relation to Aromatase and Sgk Expression During the Transition of Granulosa Cells to Luteal Cells", Molecular Endocrinology 13(8):1318-1337 (1999).
Hackam D.G. et al., "Translation of Research Evidence from Animals to Humans", JAMA 296(14):1731-1732 (Oct. 11, 2006).
Hartwig J.F., "Ubergangsmetall-Katalysierte Synthese Von Arylaminen und Arylethern aus Arylhalogeniden und- Triflaten: Anwendungen und Reaktionsmechanismus", Angewandte Chemie 110(15):2154-2177 (Aug. 3, 1998), together with an English-language abstract.
Hayashi M. et al., "BMK1 Mediates Growth Factor-Induced Cell Proliferation Through Direct Cellular Activation of Serum and Glucocorticoid-Inducible Kinase", The Journal of Biological Chemistry 276(12):8631-8634 (Mar. 23, 2001).
Henke G. et al., "Regulation of the Voltage Gated K+ Channel Kv1.3 by the Ubiquitin Ligase Nedd4-2 and the Serum and Glucocorticoid Inducible Kinase SGK1", Journal of Cellular Physiology 1999:194-199 (2004).
Hughes D.L. et al., "A Mechanistic Study of the Mitsunobu Esterification Reaction", J. Am. Chem. Soc. 110:6487-6491 (1988).
Imaizumi K. et al., "Differential Expression of Sgk mRNA, a Member of the Ser/Thr Protein Kinase Gene Family, in Rat Brain After CNS Injury", Molecular Brain Research 26:189-196 (1994).
Jordan V.C., "Tamoxifen: A Most Unlikely Pioneering Medicine", Nature Reviews-Drug Discovery 2:205-213 (Mar. 2003).
Kang S-K. et al., "Copper-Catalyzed N-Arylation of Aryl Iodides With Benzamides or Nitrogen Heterocycles in the Presence of Ethylenediamine", Synlett 3:427-430 (2002).
Klapars A. et al., "A General and Efficient Copper Catalyst for the Amidation of Aryl Halides and the N-Arylation of Nitrogen Heterocycles", J. Am. Chem. Soc. 123:7727-7729 (2001).
Klingel K. et al., "Expression of Cell Volume-Regulated Kinase H-Sgk in Pancreatic Tissue", Am J Physiol Gastrointest Liver Physiol 279:G998-G1002 (2000).
Kobayashi T. et al., "Activation of Serum- and Glucocorticoid-Regulated Protein Kinase by Agonists that Activate Phosphatidylinositide 3-Kinase is Mediated by 3-Phosphoinositide-Dependent Protein Kinase-1 (PDK1) and PDK2", Biochem. J. 339:319-328 (1999).
Kobayashi T. et al., "Characterization of the Structure and Regulation of Two Novel Isoforms of Serum- and Glucocorticoid-Induced Protein Kinase", Biochem. J. 344:189-197 (1999).
Kočevar M. et al., "New Synthetic Approach for Pyrazolo[3,4-b]Pyrazines and Isoxazolo [4,5-b]Pyrazines", Heterocycles 19(2):339-342 (1982).
Kočevar M. et al., "Neighbouring Group Participation in Formation of Condensed Azines. Formation of Pyrazolo(3,4-b)Pyrazines, Isoxazolo (4,5-b)Pyrazines and Isothiazolo(5,4-b)-Pyridine", Monatshefte für Chemie 113:731-744 (1982).
Kumar J.M. et al., "Sgk, a Putative Serine/Threonine Kinase, is Defferentially Expressed in the Kidney of Diabetic Mice and Humans", J Am Soc Nephrol 10:2488-2494 (1999).
Kwong F Y et al., "Copper-Catalyzed Coupling of Alkylamines and Aryl Iodides: An Efficient System Even in an Air Atmosphere", Organic Letters 4(4):581-584 (2002).
Lam P.Y.S. et al., "New Aryl/Heteroaryl C—N Bond Cross-Coupling Reactions Via Arylboronic Acid/Cupric Acetate Arylation", Tetrahedron Letters 39:2941-2944 (1998).

(56) References Cited

OTHER PUBLICATIONS

Lang F. et al., "Regulation of Channels by the Serum and Glucocorticoid-Inducible Kinase-Implications for Transport, Excitability and Cell Proliferation", Cellular Physiology and Biochemistry 13:041-050 (2003).

Lang F. et al., "Deranged Transcriptional Regulation of Cell-Volume-Sensitive Kinase hSGK in Diabetic Nephropathy", PNAS 97(14):8157-8162 (Jul. 5, 2000).

Lee E. et al., "Tissue-Specific Expression of the Transcriptionally Regulated Serum and Glucocorticoid-Inducible Protein Kinase (Sgk) During Mouse Embryogenesis", Mechanisms of Development 103:177-181 (2001).

Lidström P. et al., "Microwave Assisted Organic Synthesis-A Review", Tetrahedron 57:9225-9283 (2001).

Lin H. et al., "2,3,5-Trisubstituted Pyridines as Selective AKT Inhibitors. Part II: Improved Drug-Like Properties and Kinase Selectivity from Azaindazoles", Bioorganic & Medicinal Chemistry 20:679-683 (2010).

Littke A.F. et al., "Palladium-Catalyzed Coupling Reactions of Aryl Chlorides", Angew. Chem. Int. Ed. 41:4176-4211 (2002).

Liu D. et al., "Identification of CISK, a New Member of the SGK Kinase Family that Promotes IL-3-Dependent Survival", Current Biology 10:1233-1236 (2000).

Loffing J. et al., "SGK Kinases and Their Role in Epithelial Transport", Annu. Rev. Physiol. 68:461-490 (2006).

Loffing J. et al., "Aldosterone Induces Rapid Apical Translocation of ENaC in Early Portion of Renal Collecting System: Possible Role of SGK", Am J Physiol Renal Physiol 280:F675-F682 (2001).

McCormick J.A. et al., "SGK1: A Rapid Aldosterone-Induced Regulator of Renal Sodium Reabsorption", Physiology 20:134-139 (2005).

Mitsunobu O., "The Use of Diethyl Azodicarboxylate and Triphenylphosphine in Synthesis and Transformation of Natural Products", Synthesis pp. 1-28 (Jan. 1981).

Mizuno H. et al., "The ERK MAP Kinase Pathway Mediates Induction of SGK (Serum- and Glucocorticoid-Inducible Kinase) by Growth Factors", Genes to Cells 6:261-268 (2001).

Mosrin M. et al., "High Temperature Zincation of Functionalized Aromatics and Heteroaromatics Using TMPZnCl LiCl and Microwave Irradiation", Chem. Commun. pp. 5615-5617 (2009).

Muci A.R. et al., "Practical Palladium Catalysts for C—N and C—O Bond Formation", Topics in Current Chemistry 219:131-209 (2002).

Netherton M.R. et al., "Palladium-Catalyzed Cross-Coupling Reactions of Unactivated Alkyl Electrophiles with Organometallic Compounds", Top Organomet Chem 14:85-108 (2005).

Nichols D.E. et al., "1-(2,5-Dimethoxy-4-(Trifluoromethyl)Phenyl)-2-Aminopropane: A Potent Secrotonin 5-HT2A/2C Agonist", J. Med. Chem. 37:4346-4351 (1994).

Park J. et al., "Serum and Glucocorticoid-Inducible Kinase (SGK) is a Target of the PI 3-Kinase-Stimulated Signaling Pathway", The EMBO Journal 18(11):3024-3033 (1999).

Pelletier J.C. et al., "Mitsunobu Reaction Modifications Allowing Product Isolation Without Chromatography: Application to a Small Parallel Library", Tetrahedron Letters 41:797-800 (2000).

Perrin D. et al., "Capillary Microfluidic Electrophoretic Mobility Shift Assays: Application to Enzymatic Assays in Drug Discovery", Expert Opin. Drug Discovery 5(1):51-63 (2010).

Perrotti N. et al., "Activation of Serum- and Glucocorticoid-Induced Protein Kinase (Sgk) by Cyclic AMP and Insulin", The Journal of Biological Chemistry 276(12):9406-9412 (Mar. 23, 2001).

Qing F-L et al., "First Synthesis of Ortho-Trifluoromethylated Aryl Triflates", J. Chem. Soc., Perkin Trans. 1:3053-3057 (1997).

Richards J.S. et al., "Ovarian Cell Differentiation: A Cascasde of Multiple Hormones, Cellular Signals, and Regulated Genes", Recent Progress in Hormone Research 50:223-254 (1995).

Robson H. et al., "Thyroid Hormone Acts Directly on Growth Plate Chondrocytes to Promote Hypertrophic Differentiation and Inhibit Clonal Expansion and Cell Proliferation", Endocrinology 141(10):3887-3897 (2000).

Rozansky D.J. et al., "Hypotonic Induction of SGK1 and Na+ Transport in A6 Cells", Am J Physiol Renal Physiol 283:F105-F113 (2002).

Sakamoto T. et al., "Palladium-Catalyzed Cyanation of Aryl and Heteroaryl Iodides With Copper(I) Cyanide", J. Chem. Soc., Perkin Trans. 1 pp. 2323-2326 (1999).

Sakoda H. et al., "Differing Roles of Akt and Serum- and Glucocorticoid-Regulated Kinase in Glucose Metabolism, DNA Synthesis, and Oncogenic Activity", The Journal of Biological Chemistry 278(28):25802-25807 (Jul. 11, 2003).

Shenolikar S. et al., "NHERF: Targeting and Trafficking Membrane Proteins", Am J Physiol Renal Physiol 280: F389-F395 (2001).

Shigaev A. et al., "Regulation of Sgk by Aldosterone and its Effects on the Epithelial Na+ Channel", Am J Physiol Renal Physiol 278:F613-F619 (2000).

Shukunami C. et al., "Sequential Progression of the Differentiation Program by Bone Morphogenetic Protein-2 in Chondrogenic Cell Line ATDC5", Experimental Cell Research 241:1-11 (1998).

Shukunami C. et al., "Chondrogenic Differentiation of Clonal Mouse Embryonic Cell Line ATDC5 In Vitro: Differentiation-Dependent Gene Expression of Parathyroid Hormone (PTH)/PTH-Related Peptide Receptor", The Journal of Cell Biology 133(2):457-468 (Apr. 1996).

Sicker D. et al., "A Facile Synthesis of Pyrazolo[3,4-b]Pyrazines", J. Prakt. Chemie. Band 332:584-586 (1990).

Snyder P.M. et al., "Serum and Glucocorticoid-Regulated Kinase Modulates Nedd4-2-Mediated Inhibition of the Epithelial Na+ Channel", The Journal of Biological Chemistry 277(1):5-8 (Jan. 4, 2002).

Staub O. et al., "Regulation of Stability and Function of the Epithelial Na+ Channel (ENaC) by Ubiquitination", The EMBO Journal 16(21):6325-6336 (1997).

Su D-B et al., "Methyl Chlorodifluoroacetate a Convenient Trifluoromethylating Agent", Tetrahedron Letters 32 (52):7689-7690 (1991).

Tunoori A R et al., "Polymer-Bound Triphenylphosphine as Traceless Reagent for Mitsunobu Reactions in Combinatorial Chemistry: Synthesis of Aryl Ethers from Phenols and Alcohols", Tetrahedron Letters 39:8751-8754 (1998).

Urata H. et al., "A Novel and Convenient Method for Trifluoromethylation of Organic Halides Using CF3SiR'3/KF/Cu (I) System", Tetrahedron Letters 32(1):91-94 (1991).

Vallon V. et al., "New Investigator Award in Regulatory and Integrative Physiology-Role of Sgk1 in Salt and Potassium Homeostasis", Am J Physiol Regul Integr Comp Physiol 288:R4-R10 (2005).

Vallon V. et al., "New Insights into the Role of Serum- and Glucocorticoid-Inducible Kinase SGK1 in the Regulation of Renal Function and Blood Pressure", Current Opinion in Nephrology and Hypertension 14:59-66 (2005).

Vinot N. et al., "Properties of [1]Benzopyrano[2,3-b]Quinoxalin-12-One", Journal of Heterocyclic Chemistry 20 (6):1645-1650 (Nov.-Dec. 1983).

Wagner C.A. et al., "Effects of the Serine/Threonine Kinase SGK1 on the Epithelial Na+ Channel (ENaC) and CFTR: Implications for Cystic Fibrosis", Cellular Physiology and Biochemistry 11:209-218 (2001).

Wagner C.A. et al., "The Heterodimeric Amino Acid Transporter 4F2hc/LAT1 is Associated in Xenopus Oocytes With a Non-Selective Cation Channel that is Regulated by the Serine/Threonine Kinase Sgk-1", Journal of Physiology 526 (1):35-46 (2000).

Waldegger S. et al., "H-Sgk Serine-Threonine Protein Kinase as Transcriptional Target of p38/MAP Kinase Pathway in HepG2 Human Hepatoma Cells", Cellular Physiology and Biochemistry 10:203-208 (2000).

Waldegger S. et al., "H-Sgk Serine-Threonine Protein Kinase Gene as Transcriptional Target of Transforming Growth Factor β in Human Intestine", Gastroenterology 116:1081-1088 (1999).

Waldegger S. et al., "Cloning and Characterization of a Putative Human Serine/Threonine Protein Kinase Transcriptionally Modified During Anisotonic and Isotonic Alterations of Cell Volume", Proc. Natl. Acad. Sci. 94:4440-4445 (Apr. 1997).

Wang J. et al., "SGK Integrates Insulin and Mineralocorticoid Regulation of Epithelial Sodium Transport", Am J Physiol Renal Physiol 280:F303-F313 (2001).

(56) References Cited

OTHER PUBLICATIONS

Wärntges S. et al., "Excessive Transcription of the Human Serum and Glucocorticoid Dependent Kinase hSGK1 in Lung Fibrosis", Cellular Physiology and Biochemistry 12:135-142 (2002).

Wärntges S. et al., "Cerebral Localization and Regulation of the Cell Volume-Sensitive Serum- and Glucocorticoid-Dependent Kinase SGK1", Eur J Physiol 443:617-624 (2002).

Webster M.K. et al., "Immediate-Early Transcriptional Regulation and Rapid mRNA Turnover of a Putative Serine/Threonine Protein Kinase", The Journal of Biological Chemistry 268(16):11482-11485 (Jun. 5, 1993).

Webster M.K. et al., "Characterization of Sgk, a Novel Member of the Serine/Threonine Protein Kinase Gene Family Which is Transcriptionally Induced by Glucocorticoids and Serum", Molecular and Cellular Biology 13(4):2031-2040 (Apr. 1993).

Yang B.H. et al., "Palladium-Catalyzed Amination of Aryl Halides and Sulfonates", Journal of Organometallic Chemistry 576:125-146 (1999).

Yoshida K. et al., "Synthesis of Condensed Quinoxalines. VI. Synthesis of 1H-Pyrazolo[3,4-b]Quinoxaline N-Oxides and Related Compounds", Chem. Pharm. Bull. 32(9):3361-3365 (1984).

Yun C.C., "Concerted Roles of SGK1 and the Na+/H+ Exchanger Regulatory Factor 2 (NHERF2) in Regulation of NHE3", Cellular Physiology and Biochemistry 13:029-040 (2003).

Yun C.C. et al., "Glucocorticoid Activation of Na+/H+ Exchanger Isoform 3 Revisited", The Journal of Biological Chemistry 277(10):7676-7683 (Mar. 8, 2002).

International Search Report dated Nov. 29, 2011 received from the European Patent Office from related International Application No. PCT/EP2011/066220 and U.S. Appl. No. 13/236,027.

International Search Report dated Oct. 31, 2012 received from the European Patent Office from related International Application No. PCT/EP2012/068291 and U.S. Appl. No. 14/345,488.

Chemical Abstract Registry No. 1279891-92-7, indexed in the Registry File on STN CAS Online Apr. 14, 2011 (1 page).

Chemical Abstract Registry No. 1279877-61-0, indexed in the Registry File on STN CAS Online Apr. 14, 2011 (1 page).

Chemical Abstract Registry No. 1279839-55-2, indexed in the Registry File on STN CAS Online Apr. 14, 2011 (1 page).

Chemical Abstract Registry No. 1279839-29-0, indexed in the Registry File on STN CAS Online Apr. 14, 2011 (1 page).

Chemical Abstract Registry No. 1279839-28-9, indexed in the Registry File on STN CAS Online Apr. 14, 2011 (1 page).

Chemical Abstract Registry No. 1279839-27-8, indexed in the Registry File on STN CAS Online Apr. 14, 2011 (1 page).

Chemical Abstract Registry No. 1279830-11-3, indexed in the Registry File on STN CAS Online Apr. 14, 2011 (1 page).

Chemical Abstract Registry No. 1279829-87-6, indexed in the Registry File on STN CAS Online Apr. 14, 2011 (1 page).

U.S. Office Action dated Nov. 17, 2014 in U.S. Appl. No. 14/345,488.

Final Office Action mailed on Feb. 26, 2015, for U.S. Appl. No. 14/345,488, filed Sep. 18, 2012, six pages.

U.S. Attorney's Office, New Jersey (May 7, 2012). Press Release: "Former research chemist at global pharmaceutical company sentenced to 18 months in prison for theft of trade secrets," located at http://www.justice.gov/archive/usao/nj/Press/files/Li,%20Yuan%20Sentencing%20News%20Release.html>, last visited on May 19, 2015, two pages.

Ogura, K. (1997). Kyoto University Graduate School. Engineering Graduate Course, 16 Total Pages (with Machine Translation).

N-[4-(1H-PYRAZOLO[3,4-B]PYRAZIN-6-YL)PHENYL]SULFONAMIDES AS PHARMACEUTICALS

CROSS REFERENCE TO RELATED APPLICATIONS

The instant application is a continuation of U.S. application Ser. No. 13/236,027, filed Sep. 19, 2011, which is incorporated herein by reference in its entirety.

The present invention relates to N-[4-(1H-pyrazolo[3,4-b]pyrazin-6-yl)-phenyl]-sulfonamides of the formula I,

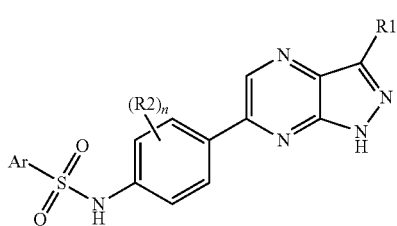

wherein Ar, R1, R2 and n have the meanings indicated below. The compounds of the formula I are valuable pharmacologically active compounds which modulate protein kinase activity, specifically the activity of serum and glucocorticoid regulated kinase (SGK), in particular of serum and glucocorticoid regulated kinase isoform 1 (SGK-1, SGK1), and are suitable for the treatment of diseases in which SGK activity is inappropriate, for example degenerative joint disorders or inflammatory processes such as osteoarthritis or rheumatism. The invention furthermore relates to processes for the preparation of the compounds of the formula I, their use as pharmaceuticals, and pharmaceutical compositions comprising them.

Due to their physiologic importance, variety, and ubiquity, protein kinases have become one of the most important and widely-studied family of enzymes in biochemical and medical research. Currently, there are about 500 different known protein kinases. However, because three to four percent of the human genome is a code for the formation of protein kinases, there may be many thousands of distinct and separate kinases in the human body. Protein kinases serve to catalyze the phosphorylation of an amino acid side chain in various proteins by the transfer of the gamma-phosphate of the ATP-$Mg^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity.

The protein kinase family of enzymes is typically classified into two main subfamilies, protein tyrosine kinases, which phosphorylate tyrosine residues, and protein serine/threonine kinases (PSTK), which phosphorylate serine and threonine residues. The PSTK subfamily includes cyclic AMP- and cyclic GMP-dependent protein kinases, calcium- and phospholipid-dependent protein kinase, calcium- and calmodulin-dependent protein kinases, casein kinases, cell division cycle protein kinases and others. These kinases are usually cytoplasmic or associated with the particulate fractions of cells, possibly by anchoring proteins.

Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and their associated signal transduction pathways are important targets for drug design.

Serum and glucocorticoid regulated kinases, also designated as serum/glucocorticoid regulated kinase, serum and glucocorticoid induced kinase, serum and glucocorticoid inducible kinase or serum and glucocorticoid dependent kinase, form a family of serine/threonine kinases. Currently three members are known, designated as SGK-1, SGK-2 and SGK-3. SGK-3 is also described under the name SGKL (SGK-like), and CISK. SGK-1 was described in 1993 for the first time as an "immediate early genes" in a rat mammary cancer cell line (Webster et al., 1993a; Webster et al., 1993b). At the protein level the three isoforms show a homology of at least 80% in their catalytic domain. SGK-1 is expressed in almost all tissues that have been tested so far, but the amounts of mRNA expressed vary greatly depending on the nature of the studied tissue type (Gonzalez-Robayna et al., 1999; Waldegger et al., 1999; Alliston et al., 2000; Klingel et al., 2000; Lang et al., 2000; Loffing et al., 2001; Fillon et al., 2002; Warntges et al., 2002a). In addition, SGK-1 mRNA is found in several embryonic tissues. During mouse embryogenesis, the SGK-1 mRNA shows development-dynamic changes in specific tissues of the embryo (decidua, yolk sac, otic vesicle), and is detectable during the organogenesis in lung buds, brain, heart, liver, thymus, etc. (Lee et al., 2001). SGK-2 is expressed with greatest abundance in epithelial tissues, such as in the kidney, liver, pancreas, and specific areas of the brain (Kobayashi et al., 1999). SGK-3 was detected in all tested tissues and is especially found in the adult heart and spleen (Kobayashi et al., 1999; Liu et al., 2000).

A distinguishing feature of SGK to many other kinases is based on the stringent stimulus-dependent regulation of transcription, cellular localization and enzymatic activation (Firestone et al., 2003) of the molecule. In order to induce and activate SGK-1, a variety of stimuli are known. These include mineralocorticoids (Brennan and Fuller, 2000; Shigaev et al., 2000; Bhargava et al., 2001), gonadotropins (Richards et al., 1995; Gonzalez-Robayna et al., 2000), 1,25(OH)2D3 (Akutsu et al., 2001), p53, osmotic, hypotonic and cellular volume changes (Waldegger et al., 1997; Klingel et al., 2000; Waldegger et al., 2000; Rozansky et al., 2002; Warntges et al., 2002a), cytokines such as GM-CSF and TNF-alpha (Cooper et al., 2001) or by TGF-beta (Kumar et al., 1999; Waldegger et al.; 1999; Lang et al., 2000). In further growth-dependent signaling pathways SGK is induced by serum (Webster et al., 1993a), insulin and IGF-1 (Kobayashi and Cohen, 1999; Park et al., 1999; Perrotti et al., 2001), FSH (Alliston et al., 1997), Fibroblast and Platelet-derived growth factor (Davies et al., 2000), activators of the Erk signaling cascade (Hayashi et al., 2001) and TPA (Mizuno and Nishida, 2001). SGK-1 is also known to be activated in pathological changes such as ischemic brain injury (Imaizumi et al., 1994), viral hepatitis (Fillon et al., 2002), pulmonary fibrosis (Warntges et al., 2002b) or cardiac fibrosis (Funder 2001).

In order to be converted into its functional form, SGK-1 requires activation by phosphorylation. This is mediated by a signaling cascade involving the phosphatidylinositol 3 (PI-3)

kinase and phosphoinositide 3-dependent kinases PDK1 and PDK2. The activation of SGK-1 through the PI-3 kinase signaling pathway is known to be a response to insulin, IGF and growth factors. For activation the phosphorylation of two amino acid residues is necessary, threonine$^{256}$ on the T-loop and serine$^{422}$ at the hydrophobic motif of the protein. Phosphorylation at threonine$^{256}$ is mediated by PDK1, phosphorylation at serine$^{422}$ should be catalyzed by a putative PDK2, which is not yet known (Kobayashi and Cohen, 1999; Park et al., 1999; Biondi et al., 2001).

For the function of SGK, there are a series of studies that show regulatory influence of SGK-1, SGK-2 and SGK-3 on cell membrane channels. It was shown that the epithelial Na$^+$ channel (ENaC), the main transporter for the mineralocorticoid-regulated Na$^+$ reabsorption in the renal tubule, is a target of SGK-1, SGK-2 and SGK-3 (Alvarez de la Rosa et al., 1999; Bohmer et al., 2000; Wagner et al, 2001; Wang et al., 2001; Faletti et al., 2002; Friedrich et al., 2003). The interaction of ENaC and SGK is not by direct phosphorylation (Lang et al., 2000), but due to the inactivation of the ubiquitin ligase Nedd-4-2 (Debonneville et al., 2001; Snyder et al., 2002) as a result of phosphorylation by SGK. As a result, the amount and residence time of ENaC in the cell membrane is increased (Staub et al., 1997; Alvarez de la Rosa et al., 1999; Wagner et al., 2001). It has also been shown in a number of experiments that ROMK1 is a molecular target of SGK. However, ROMK1 is not directly regulated by SGK, but needs the "Na$^+$/H$^+$ exchange regulating factor 2" (NHERF2) as an intermediary molecule (Shenolikar and Weinmann, 2001; Yun, 2003). The same mechanism applies to another target molecule of SGK, the Na$^4$YH$^+$ transporter NHE3 (Yun et al., 2002). In addition it has also been shown in experiments on *Xenopus* oocytes that SGK influences the Kv1.3 channel-dependent K$^+$ current (Gamper et al., 2002; Warntges et al., 2002a). It was also reported that SGK regulates the amino acid transporter SN1 and 42F/LAT (Wagner et al., 2000; Böhmer et al., 2003a, b). SGK-1 has also been shown to play a role in cell proliferation and electrolyte homeostasis (Loffing et al., 2006; McCormick et al., 2005; Vallon et al., 2005; Vallon and Lang, 2005; Lang et al., 2003). SGK-1 is thought to regulate several cellular mechanisms that contribute to disease states. For example, SGK-1 has been shown to mediate fibronectin formation in diabetic nephropathy (Feng et al., 2005). SGK1 has also been shown to mediate insulin, IGF-1, and aldosterone-induced Na$^+$ retention in renal and cardiovascular disease (McCormick et al., 2005; Vallon et al., 2005; Lang et al., 2003). In addition, SGK-1 has been shown to be involved in inducing the transcription and procoagulation activity of tissue factor (TF) (BelAiba et al., 2006), and in regulating IGF-1-mediated cell proliferation (Henke et al., 2004).

Osteoarthritis (OA) is one of the most common degenerative joint diseases and leads in an advanced stage to a loss of joint function. During the chronic course of illness, there is a destruction of the articular cartilage down to the underlying bone tissue, which makes a joint replacement surgery in affected patients necessary. In addition to the destruction of the cartilage, pathological changes in the synovial membrane and the ligaments can also be observed. The disease is temporarily accompanied by inflammatory processes like in rheumatoid arthritis, but differs from it. The exact causes of the disease are still unknown, however, several factors come into question, such as metabolic changes, mechanical stress, genetic disorders or joint injuries. Regardless of the original trigger, the degradation of articular cartilage occurs as a common pathological feature of OA. A key feature of the pathological condition of OA is the proteolytic cleavage of collagens and proteoglycans. Simultaneously a number of other processes occur such as anabolic repair mechanisms redifferentiation of the cells or cell death. The precise molecular mechanisms underlying these processes are still poorly understood.

The healthy functioning of the adult cartilage is created by its unique biomechanical properties, providing both the resistance against high pressure as well as the necessary elasticity of the tissue. The decisive factor is the special organization of the cartilage tissue. Unlike most other tissues, the cartilage cells are not in direct contact but are embedded separately from each other in an extracellular matrix (ECM). The macromolecules of this ECM guarantee the viability of the articular cartilage and joints. The basic structure of the ECM consists of a network that is formed by fibrils of collagen types II, IX and XI.

Proteoglycans, mainly aggrecan, are embedded in the ECM producing an extremely high osmotic water binding capacity. The water pressure generated in connection with the properties of the collagen backbone guarantee the specific properties of the cartilage. A main feature of the pathogenesis of OA is the loss of the ECM of the cartilage and the articular cartilage tissue. The function of the affected joint is restricted by or lost by this mechanism. In addition, various symptomatic parameters such as pain appear during symptomatic progression of the disease. Current treatments for osteoarthritis are limited mostly to the alleviation of symptomatic complaints. A causal therapy based on drugs, which leads to the decrease of cartilage degeneration, is not possible to current knowledge. Therefore, there is a considerable need for novel drugs for the prevention and/or therapy of osteoarthritis.

It has been shown, through comparative gene expression analysis of samples of total-cellular RNA from healthy and degenerated/degenerating cartilage that SGK-1 is expressed in degenerated/degenerating osteoarthritic cartilage, while it is not detectable in healthy articular cartilage (Bartnik et al., 2006). Moreover, further experiments gave evidence of the causal implication of SGK in the pathogenesis of degenerative cartilage changes (Bartnik et al., 2006). As a conclusion of these studies, SGK-1 is specifically involved in pathological conditions of the cartilage, for example in the context of rheumatoid arthritis or osteoarthritis, in particular in the context of osteoarthritis, and thus represents a key molecule inducing cartilage degradative processes. Due to the high homology between the SGK family members, it is assumed that this also applies to the SGK-2 and SGK-3.

The identification of these relationships allows the discovery of drugs for the prevention or therapy of degenerative cartilage changes by determining the effect of potential drugs on the activity of SGK and/or the levels of SGK by known test methods. The causal implication of SGK in the pathogenesis of degenerative joint disease allows a focused search for therapeutic agents that target regulatory mechanisms for the restoration of normal cell physiology of cartilage. In the joints of mouse embryos SGK-1 mRNA was detected specifically in hypertrophic chondrocytes but not in proliferative cells. The role of SGK-1 in this model of skeletal development and endochondral ossification shows that the natural occurrence of SGK-1 in cartilage is not associated with the synthesis and maintenance of cartilage, but exerts its function in the conversion (hypertrophy) and degradation. The expression of SGK-1 in osteoarthritic cartilage is thus a process that causes or promotes the pathology of OA. Due to its regulatory properties SGK-1 could be a key molecule for the induction of early pathological changes in cartilage as well as for the later degradative activities. Therefore, SGK-1 is a very relevant target for the pharmacological intervention in osteoarthritis.

To specifically study the function of SGK-1 during differentiation of cartilage, human SGK-1 was overexpressed in murine ATDC5 cells. In these experiments, it was clearly demonstrated that overexpression of SGK-1 causes inhibition of cartilage synthesis. Both the amount of Alcian blue stained proteoglycan as well as aggrecan mRNA was significantly reduced. A kinase deficient SGK-1 form, however, had no negative effect on these parameters. Regarding the effect of SGK-1 in OA diseased articular cartilage, several conclusions can be drawn from these experiments. On the one hand, SGK-1 expressing chondrocytes are no longer able to synthesize sufficient extracellular matrix such as proteoglycans, which are essential for the function of the tissue. On the other hand, the cartilage cells are inhibited to compensate for, or repair, degradation processes by increasing the expression of genes such as aggrecan. Therefore a function of SGK-1 as a potential cause and central factor of OA pathology is confirmed. SGK-1 thus represents a highly relevant target molecule for the development of novel drugs for the treatment of degenerative cartilage changes, especially osteoarthritis.

In view of the relevance of SGK-1 for various physiological processes outlined above, inhibitors of SGK-1 such as the compounds of the present invention can be used in the treatment, including therapy and prophylaxis, of various disease states in which SGK-1 activity plays a role or which are associated with an inappropriate SGK-1 activity, or in which an inhibition, regulation or modulation of signal transduction by SGK-1 is desired by the physician, for example degenerative joint disorders and degenerative cartilage changes including osteoarthritis, osteoarthrosis, rheumatoid arthritis, spondylosis, chondrolysis following joint trauma and prolonged joint immobilization after meniscus or patella injuries or ligament tears, connective tissue disorders such as collagenoses, periodontal disorders, wound-healing disturbances, diabetes including diabetes mellitus, diabetic nephropathy, diabetic neuropathy, diabetic angiopathy and microangiopathy, obesity, metabolic syndrome (dyslipidaemia), systemic and pulmonary hypertension, cerebral infarctions, cardiovascular diseases including cardiac fibrosis after myocardial infarction, cardiac hypertrophy and heart failure, arteriosclerosis, renal diseases including glomerulosclerosis, nephrosclerosis, nephritis, nephropathy and electrolyte excretion disorder, and any type of fibrosis and inflammatory processes including liver cirrhosis, lung fibrosis, fibrosing pancreatitis, rheumatism, arthritis, gout, Crohn's disease, chronic bronchitis, radiation fibrosis, sclerodermatitis, cystic fibrosis, scar formation and Alzheimer's disease. Inhibitors of SGK-1 such as the compounds of the present invention can also be used in the treatment of pain including acute pain like pain following injuries, post-operative pain, pain in association with an acute attack of gout and acute pain following jaw-bone surgery interventions, and chronic pain like pain associated with chronic musculoskeletal diseases, back pain, pain associated with osteoarthritis or rheumatoid arthritis, pain associated with inflammation, amputation pain, pain associated with multiple sclerosis, pain associated with neuritis, pain associated with carcinomas and sarcomas, pain associated with AIDS, pain associated with chemotherapy, trigeminus neuralgia, headache, migraine cephalalgia, neuropathic pains, post-herpes zoster neuralgia. Inhibitors of SGK-1 such as the compounds of the present invention can also be used in tumor therapy for inhibiting the growth of tumor cells and tumor metastases. Inhibitors of SGK-1 such as the compounds of the present invention can also be used for the treatment of chronic disorders of the locomotor system such as inflammatory, immunologically or metabolically related acute and chronic arthritides, arthropathies, myalgias and disturbances of bone metabolism. Further, inhibitors of SGK-1 such as the compounds of the present invention can be used in the treatment of peptic ulcers, especially in forms that are triggered by stress, in the treatment of tinnitus, in the treatment of bacterial infections and in anti-infective therapy, for increasing the learning ability and attention, for counteracting cellular aging and stress and thus increasing life expectancy and fitness in the elderly, in states of neuronal excitability including epilepsy, in the treatment of glaucoma or cataracts, and in the treatment of coagulopathies including dysfibrinogenaemia, hypoproconvertinaemia, haemophilia B, Stuart-Prower defect, prothrombin complex deficiency, consumption coagulopathy, fibrinolysis, immunokoagulopathy or complex coagulopathies.

Further details about the physiological role of SGK can be found, for example, in the mentioned literature articles, the particulars of which are as follows.

Akutsu, N., Lin. R., Bastien. Y., Bestawros, A., Enepekides, D. J., Black, M. J., and White, J. H. (2001). Regulation of gene Expression by 1alpha,25-dihydroxyvitamin D3 and Its analog EB1089 under growth-inhibitory conditions in squamous Carcinoma Cells. Mol Endocrinol, 15, 1127-1139.

Alliston, T. N., Maiyar, A. C., Buse, P., Firestone, G. L., and Richards, J. S. (1997). Follicle stimulating hormone-regulated expression of serum/glucocorticoid-inducible kinase in rat ovarian granulosa cells: a functional role for the Sp1 family in Promoter activity. Mol Endocrinol, 11, 1934-1949.

Alliston, T. N., Gonzalez-Robayna, J. J., Buse, P., Firestone, G. L., and Richards, J. S. (2000). Expression and localization of serum/glucocorticoid-induced kinase in the rat ovary: relation to follicular growth and differentiation. Endocrinology, 141, 385-395.

Alvarez, d. I. R., Zhang, P., Naray-Fejes-Toth, A., Fejes-Toth, G., and Canessa, C. M. (1999). The serum and glucocorticoid kinase sgk increases the abundance of epithelial sodium Channels in the plasma membrane of *Xenopus* oocytes. J Biol Chem, 274, 37834-37839.

Bartnik, E., Aigner, T., Dietz, U., and Brimmer, A., (2006). The use of a Serum/Glucocorticoid-regulated Kinase. WO 06/061130.

BelAiba, R. S., Djordjevic, T., Bonello, S., Artunc, F., Lang, F., Hess, J., and Görlach, A. (2006). The serum- and glucocorticoid-inducible kinase Sgk-1 is involved in pulmonary vascular remodeling: role in redox-sensitive regulation of tissue factor by thrombin. Circ Res 98(6), 828-836.

Klingel, K., Warntges, S., Bock, J., Wagner, C. A., Sauter, M., Waldegger, S., Kandolf, R., and Lang, F. (2000). Expression of cell volume-regulated kinase h-sgk in pancreatic tissue. Am J Physiol Gastrointest Liver Physiol, 279, G998-G1002.

Bhargava, A., Fullerton, M. J., Myles, K., Purdy, T. M., Funder, J. W., Pearce, D., and Cole, T. J. (2001). The serum and glucocorticoid-induced kinase is a physiological mediator of aldosterone action. Endocrinology, 142, 1587-1594.

Biondi, R. M., Kieloch, A., Currie, R. A., Deak, M., and Alessi, D. R. (2001). The PIF-binding pocket in PDK1 is essential for activation of S6K and SGK, but not PKB. EMBO J, 20, 4380-4390.

Boehmer, C., Okur, F., Setiawan, I., Broer, S., and Lang, F. (2003a). Properties and regulation of glutamine transporter SN1 by protein kinases SGK and PKB. Biochem Biophys Res Commun, 306, 156-162.

Boehmer, C., Wilhelm, V., Palmada, M., Wallisch, S., Henke, G., Brinkmeier, H., Cohen, P., Pieske, B., and Lang, F.

(2003b). Serum and glucocorticoid inducible kinases in the regulation of the cardiac sodium Channel SCN5A. Cardiovasc Res, 57, 1079-1084.

Boehmer, C, Wagner, C. A, Beck, S., Moschen, I., Melzig, J., Werner, A., Lin, J. T., Lang, F., and Wehner, F. (2000). The shrinkage-activated Na(+) conductance of rat hepatocytes and its possible correlation to rENaC. Cell Physiol Biochem, 10, 187-194.

Brennan, F. E. and Fuller, P. J. (2000). Rapid upregulation of serum and glucocorticoidregulated kinase (sgk) gene expression by corticosteroids in vivo. Mol Cell Endocrinol, 166, 129-136.

Cooper, M. S., Bujalska, I., Rabbitt, E., Walker, E. A, Bland, R., Sheppard, M. C, Hewison, M., and Stewart, P. M. (2001). Modulation of 11beta-hydroxysteroid dehydrogenase isozymes by proinflammatory cytokines in osteoblasts: an autocrine switch from glucocorticoid inactivation to activation. J Bone Miner Res, 16, 1037-1044.

Davies, S. P., Reddy, H., Caivano, M., and Cohen, P. (2000). Specificity and mechanism of action of some commonly used protein kinase inhibitors. Biochem J, 351, 95-105.

Debonneville, C, Flores, S. Y., Kamynina, E., Plant, P. J., Tauxe, C, Thomas, M. A., Munster, C., Chraibi, A., Pratt, J. H., Horisberger, J. D., Pearce, D., Loffing, J., and Staub, O. (2001). Phosphorylation of Nedd-4-2 by Sgk1 regulates epithelial Na(+) Channel cell surface expression. EMBO J, 20, 7052-7059.

Faletti, C. J., Perrotti, N., Taylor, S. L, and Blazer-Yost, B. L. (2002). sgk: an essential convergence point for peptide and Steroid hormone regulation of ENaC mediated Na+ transport. Am J Physiol Cell Physiol, 282, C494-C500.

Feng, Y., Wang, Q., Wang, Y., Yard, B., Lang, F. (2005). SGK1-mediated fibronectin formation in diabetic nephropathy. Cell Physiol Biochem, 16(4-6), 237-244.

Fillon, S., Klingel, K., Warntges, S., Sauter, M., Gabrysch, S., Pestel, S., Tanneur, V., Waldegger, S., Zipfel, A., Viebahn, R., Haussinger, D., Broer, S., Kandolf, R., and Lang, F. (2002). Expression of the serine/threonine kinase hSGK1 in chronic viral hepatitis. Cell Physiol Biochem, 12, 47-54.

Firestone, G. L., Giampaolo, J. R., and O'Keeffe, B. A. (2003). Stimulus-dependent regulation of serum and glucocortieoid inducible protein kinase (SGK) transcription, subcellular localization and enzymatic activity. Cell Physiol Biochem, 13, 1-12.

Friedrich, B., Feng, Y., Cohen, P., Risler, T., Vandewalle, A., Broer, S., Wang, J., Pearce, D., Lang, F. (2003). The serine/threonine kinases SGK2 and SGK3 are potent stimulators of the epithlial Na(+) Channel alpha, beta, gamma-EnaC. Pflugers Arch, 445(6), 693-696.

Funder, J. (2001). Mineralocorticoids and cardiac fibrosis: the decade in review. Clin Exp Pharmacol Physiol, 28, 1002-1006.

Gamper, N., Fillon, S., Huber, S. M., Feng, Y., Kobayashi, T., Cohen, P., and Lang, F. (2002). IGF-1 up-regulates K+ Channels via PI3-kinase, PDK1 and SGK1. Pflugers Arch, 443, 625-634.

Gonzalez-Robayna, I. J., Alliston, T. N., Buse, P., Firestone, G. L., and Richards, J. S. (1999). Functional and subcellular changes in the A-kinase-signaling pathway: relation to aromatase and Sgk expression during the transition of granulosa cells to luteal cells. Mol Endocrinol, 13, 1318-1337.

Gonzalez-Robayna, I. J., Falender, A. E., Ochsner, S., Firestone, G. L., and Richards, J. S. (2000). Follicle-Stimulating hormone (FSH) stimulates phosphorylation and activation of protein kinase B (PKB/Akt) and serum and glucocorticoid-Induced kinase (Sgk): evidence for A kinase-independent signaling by FSH in granulosa cells. Mol Endocrinol, 14, 1283-1300.

Hayashi, M., Tapping, R. I., Chao, T. H., Lo, J. F., King, C. C., Yang, Y., Lee, J. D. (2001). BMK1 mediates growth factor-induced cell proliferation through direct cellular activation of serum and glucocorticoid-inducible kinase. J Biol Chem 276(12), 8631-8634.

Henke, G., Maier, G., Wallisch, S., Boehmer, C., Lang, F. (2004). Regulation of the voltage gated K+ channel Kv1.3 by the ubiquitin ligase Nedd-4-2 and the serum and glucocorticoid inducible kinase SGK1. J Cell Physiol, 199(2), 194-199.

Imaizumi, K., Tsuda, M., Wanaka, A., Tohyama, M., and Takagi, T. (1994). Differential expression of sgk mRNA, a member of the Ser/Thr protein kinase gene family, in rat brain after CNS injury. Brain Res Mol Brain Res, 26, 189-196.

Kobayashi, T. and Cohen, P. (1999). Activation of serumand glucocorticoid-regulated protein kinase by agonists that activate phosphatidylinositide 3-kinase is mediated by 3-phosphoinositide-dependent protein kinase-1 (PDK1) and PDK2. Biochem J, 339(Pt2), 319-328.

Kobayashi, T., Deak, M., Morrice, N., and Cohen, P. (1999). Characterization of the structure and regulation of two novel isoforms of serumand glucocorticoid induced protein kinase. Biochem J, 344(Pt1), 189-197.

Kumar, J. M., Brooks, D. P., Olson, B. A., and Laping, N. J. (1999). Sgk, a putative serine/threonine kinase, is differentially expressed in the kidney of diabetic mice and humans. J Am Soc Nephral, 10, 2488-2494.

Lang, F., Henke, G., Embark, H. M., Waldegger, S., Palmada, M., Böhmer, C., Vallon, V. (2003). Regulation of channels by the serum and glucocorticoid-inducible kinase-implications for transport, excitability and cell proliferation. Cell Physiol Biochem, 13(1), 41-50.

Lang, F., Klingel, K., Wagner, C. A., Stegen, C., Warttges, S., Friedrich, B., Lanzendorfer, M., Melzig, J., Moschen, I., Steuer, S., Waldegger, S., Sauter, M., Paulmichl, M., Gerke, V., Risler, T., Gamba, G., Capasso, G., Kandolf, R., Hebert, S. C., Massry, S. G., and Broer, S. (2000). Deranged transcriptional regulation of cell-volume-sensitive kinase hSGK in diabetic nephropathy. Proc Natl Acad Sci U.S.A, 97, 8157-8162.

Lee, E., Lein, E. S., Firestone, G. L. (2001). Tissue-specific expression of the transcriptionally regulated serum and glucocorticoid-inducible preotein kinase (sgk) during embryogenesis. Mech Dev 103(1-2), 177-181.

Liu, D., Yang, X., and Songyang, Z. (2000). Identification of CISK, a new member of the SGK kinase family that promotes IL-3-dependent survival. Curr Biol, 10, 1233-1236.

Loffing, J., Flores, S. Y., Staub, O. (2006). Sgk kinases and their role in epithelial transport. Annu Rev Physiol, 68, 461-490.

Loffing, J., Zecevic, M., Feraille, E., Kaissling, B., Asher, C, Rossier, B. C., Firestone, G. L., Pearce, D., and Verrey, F. (2001). Aldosterone induces rapid apical translocation of ENaC in early portion of renal collecting System: possible role of SGK. Am J Physiol Renal Physiol, 280, F675-F682

McCormick, J. A., Bhalla, V., Pao, A. C., Pearce, D. (2005). SGK1: a rapid aldosterone-induced regulator of renal sodium reabsorption. Physiology (Bethesda), 20, 134-9.

Mizuno, H. and Nishida, E. (2001). The ERK MAP kinase pathway mediates induction of SGK (serumand glucocorticoid-inducible kinase) by growth factors. Genes Cells, 6, 261-268.

Park, J., Leong, M. L, Buse, P., Maiyar, A. C., Firestone, G. L, and Hemmings, B. A. (1999). Serum and glucocorticoid-inducible kinase (SGK) is a target of the PI 3-kinase stimulated signaling pathway. EMBO J, 18, 3024-3033.

Perrotti, N., He, R. A., Phillips, S. A., Haft, C. R., and Taylor, S. I. (2001). Activation of serumand glucocorticoid-induced protein kinase (Sgk) by cyclic AMP and insulin. Biol Chem, 276, 9406-9412.

Richards, J. S., Fitzpatrick, S. L., Clemens, J. W., Morris, J. K., Alliston, T., and Sirois, J. (1995). Ovarian cell differentiation: a cascade of multiple hormones, cellular Signals, and regulated genes. Recent Prag Horm Res, 50, 223-254.

Rozansky, D. J., Wang, J., Doan, N., Purdy, T., Faulk, T., Bhargava, A., Dawson, K., and Pearce, D. (2002). Hypotonie induction of SGK1 and Na+ transport in A6 cells. Am J Physiol Renal Physiol, 283, F105-F113.

Shenolikar, S, and Weinman, E. J. (2001). NHERF: targeting and trafficking membrane proteins. Am J Physiol Renal Physiol, 280, F389-F395.

Shigaev, A., Asher, C., Latter, H., Garty, H., and Reuveny, E. (2000). Regulation of sgk by aldosterone and its effects on the epithelial Na(+) Channel. Am J Physiol Renal Physiol, 278, F613-F619.

Snyder, P. M., Olson, D. R., and Thomas, B. C. (2002). Serum and glucocorticoid regulated kinase modulates Nedd-4-2-mediated inhibition of the epithelial Na+ Channel. J Biol Chem, 277, 5-8.

Staub, O., Gautschi, I., Ishikawa, T., Breitschopf, K., Ciechanover, A., Schild, L., and Rotin, D. (1997). Regulation of stability and function of the epithelial Na+ Channel (ENaC) by ubiquitination. EMBO J, 16, 6325-6336.

Vallon, V., Wulff, P., Huang, D. Y., Loffing, J., Voelkl, H., Kuhl, D., Lang, F. (2005). Role of Sgk1 in salt and potassium homeostasis. Am J Physiol Regul Integr Comp Physiol, 288(1), R4-R10.

Vallon, V., and Lang, F. (2005). New insights into the role of serum- and glucocorticoid-inducible kinase SGK1 in the regulation of renal function and blood pressure. Curr Opin Nephrol Hypertens, 14(1), 59-66.

Wagner, C. A., Broer, A., Albers, A., Gamper, N., Lang, F., and Broer, S. (2000). The heterodimeric amino acid transporter 4F2hc/LAT1 is associated in *Xenopus* oocytes with a non-selective cation Channel that is regulated by the serine/threonine kinase sgk-1. J Physiol, 526(Pt1), 35-46.

Wagner, C. A., Ott, M., Klingel, K., Beck, S., Melzig, J., Friedrich, B., Wild, K. N., Broer, S., Moschen, I., Albers, A., Waldegger, S., Tummler, B., Egan, M. E., Geibel, J. P., Kandolf, R., and Lang, F. (2001). Effects of the serine/threonine kinase SGK1 on the epithelial Na(+) Channel (ENaC) and CFTR: implications for cystic fibrosis. Cell Physiol Biochem, 11, 209-218.

Waldegger, S., Barth, P., Raber, G., and Lang, F. (1997). Cloning and characterization of a putative human serine/threonine protein kinase transcriptionally modified during anisotonic and isotonic alterations of cell volume. Proc Natl Acad Sci U.S.A, 94, 4440-4445.

Waldegger, S., Gabrysch, S., Barth., P., Fillon, S., and Lang, F. (2000). h-sgk serinethreonine protein kinas[theta] as transcriptional target of p38/MAP kinase pathway in HepG2 human hepatoma cells. Cell Physiol Biochem, 10, 203-208.

Waldegger, S., Klingel, K., Barth, P., Sauter, M., Rfer. M. L., Kandolf, R., and Lang, F. (1999). h-sgk serine-threonine protein kinase gene as transcriptional target of transforming growth factor beta in human intestine. Gastroenterology, 116, 1081-1088.

Wang, J., Barbry, P., Maiyar, A. C., Rozansky, D. J., Bhargava, A., Leong, M., Firestone, G. L., and Pearce, D. (2001). SGK integrates insulin and mineralocorticoid regulation of epithelial sodium transport. Am J Physiol Renal Physiol, 280, F303-F313.

Warntges, S., Friedrich, B., Henke, G., Duranton, C, Lang, P. A., Waldegger, S., Meyermann, R., Kuhl, D., Speckmann, E. J., Obermuller, N., Witzgall, R., Mack, A. F., Wagner, H. J., Wagner, A., Broer, S., and Lang, F. (2002a). Cerebral localization and regulation of the cell volume-sensitive serumand glucocorticoid-dependent kinase SGK1. Pflugers Arch, 443, 617-624.

Warntges, S., Klingel, K., Weigert, C, Fillon, S., Buck, M., Schleicher, E., Rodemann, H. P., Knabbe, C, Kandolf, R., and Lang, F. (2002b). Excessive transcription of the human serum and glucocorticoid dependent kinase hSGK1 in lung fibrosis. Cell Physiol Biochem, 12, 135-142.

Webster, M. K., Goya, L., and Firestone, G. L. (1993a). Immediate-early transcriptional regulation and rapid mRNA turnover of a putative serine/threonine protein kinase. J Biol Chem, 268, 11482-11485.

Webster, M. K., Goya, L, Ge, Y., Maiyar, A. C, and Firestone, G. L. (1993b). Characterization of sgk, a novel member of the serine/threonine protein kinase gene family which is transcriptionally induced by glucocorticoids and serum. Mol Cell Biol, 13, 2031-2040.

Yun, C. C. (2003). Concerted roles of SGK1 and the Na+/H+ exchanger regulatory factor 2 (NHERF2) in regulation of NHE3. Cell Physiol Biochem, 13, 29-40.

Yun, C. C., Chen. Y., and Lang, F. (2002). Glucocorticoid activation of Na(+)/H(+) exchanger isoform 3 revisited. The roles of SGK1 and NHERF2. J Biol Chem, 277, 7676-7683.

The identification of small compounds that specifically inhibit, regulate or modulate signal transduction by SGK, is therefore desirable and an object of the present invention. But besides being effective SGK inhibitors, it is desirable that such inhibitors also have further advantageous properties, for example high bioavailability, stability in plasma and liver, and selectivity versus other kinases or receptors whose inhibition or activation is not intended. Thus, it is an object of the present invention to provide SGK inhibitors which effectively inhibit an aberrant activity of SGK in a pathological context and which have further advantageous properties, for example high bioavailability, stability in plasma and liver, and selectivity versus other kinases and receptors which are not intended to be influenced in an agonistic or antagonistic manner. This object is achieved by providing the novel compounds of the formula I which exhibit excellent SGK-1 inhibitory activity and are favorable agents with high bioavailability and stability in plasma and liver.

Thus, a subject of the present invention are the compounds of the formula I, in any of their stereoisomeric forms or a mixture of stereoisomeric forms in any ratio, and the pharmaceutically acceptable salts thereof,

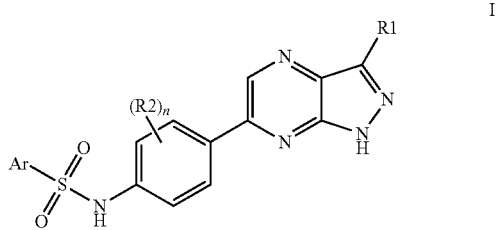

wherein

Ar is selected from the series consisting of phenyl and a 5-membered or 6-membered monocyclic aromatic heterocycle comprising 1, 2 or 3 identical or different ring heteroatoms selected from the series consisting of nitrogen, oxygen and sulfur and bonded via a ring carbon atom, which are all unsubstituted or substituted by one or more identical or different substituents R10;

n is selected from the series consisting of 0, 1 and 2;

R1 is selected from the series consisting of hydrogen, —N(R11)-R12, —N(R13)-C(O)—R14, —N(R13)-S(O)$_2$—R15, —N(R13)-C(O)—NH—R14, —C(O)—N(R16)-R17, —CN, ($C_1$-$C_4$)-alkyl and —($C_1$-$C_4$)-alkyl-O—R18;

R2 is selected from the series consisting of halogen, —($C_1$-$C_4$)-alkyl, —O—($C_1$-$C_4$)-alkyl and —CN;

R10 is selected from the series consisting of halogen, ($C_1$-$C_4$)-alkyl, ($C_3$-$C_7$)-cycloalkyl, —($C_1$-$C_4$)-alkyl-($C_3$-$C_7$)-cycloalkyl, —O—($C_1$-$C_4$)-alkyl, —O—($C_3$-$C_7$)-cycloalkyl, —O—($C_1$-$C_4$)-alkyl-($C_3$-$C_7$)-cycloalkyl-, —N(R19)-R20, —N(R21)-N(R19)-R20, —N(R21)-C(O)—R22, —NO$_2$, —C(O)—N(R23)-R24 and —CN, and two groups R10 bonded to adjacent ring carbon atoms in Ar, together with the carbon atoms carrying them, can form a 5-membered to 8-membered unsaturated ring which comprises 0, 1 or 2 identical or different ring heteroatoms selected from the series consisting of nitrogen, oxygen and sulfur, and which is unsubstituted or substituted by one or more identical or different substituents selected from the series consisting of halogen, —($C_1$-$C_4$)-alkyl, —O—($C_1$-$C_4$)-alkyl and —CN;

R11 and R12 are independently of one another selected from the series consisting of hydrogen, ($C_1$-$C_4$)-alkyl, ($C_3$-$C_7$)-cycloalkyl and —($C_1$-$C_4$)-alkyl-($C_3$-$C_7$)-cycloalkyl, or R11 and R12, together with the nitrogen atom carrying them, form a monocyclic, 4-membered to 7-membered, saturated heterocycle which, in addition to the nitrogen atom carrying R11 and R12, comprises 0 or 1 further ring heteroatom selected from the series consisting of nitrogen, oxygen and sulfur, and which is unsubstituted or substituted by one or more identical or different substituents selected from the series consisting of fluorine and ($C_1$-$C_4$)-alkyl;

R13 is selected from the series consisting of hydrogen, ($C_1$-$C_4$)-alkyl and ($C_3$-$C_7$)-cycloalkyl;

R14 and R15 are independently of one another selected from the series consisting of ($C_1$-$C_8$)-alkyl, ($C_3$-$C_7$)-cycloalkyl, —($C_1$-$C_4$)-alkyl-($C_3$-$C_7$)-cycloalkyl, phenyl, —($C_1$-$C_4$)-alkyl-phenyl, Het and —($C_1$-$C_4$)-alkyl-Het, wherein phenyl and Het all are unsubstituted or substituted by one or more identical or different substituents R30;

R16 is selected from the series consisting of hydrogen, ($C_1$-$C_4$)-alkyl and ($C_3$-$C_7$)-cycloalkyl;

R17 is selected from the series consisting of hydrogen, ($C_1$-$C_8$)-alkyl, ($C_3$-$C_7$)-cycloalkyl, —($C_1$-$C_4$)-alkyl-($C_3$-$C_7$)-cycloalkyl, phenyl, —($C_1$-$C_4$)-alkyl-phenyl, Het and —($C_1$-$C_4$)-alkyl-Het, wherein phenyl and Het all are unsubstituted or substituted by one or more identical or different substituents R30, or R16 and R17, together with the nitrogen atom carrying them, form a monocyclic, 4-membered to 7-membered, saturated heterocycle which, in addition to the nitrogen atom carrying R16 and R17, comprises 0 or 1 further ring heteroatom selected from the series consisting of nitrogen, oxygen and sulfur, and which is unsubstituted or substituted by one or more identical or different substituents selected from the series consisting of fluorine and ($C_1$-$C_4$)-alkyl;

R18 is selected from the series consisting of hydrogen and ($C_1$-$C_4$)-alkyl;

R19 is selected from the series consisting of hydrogen, ($C_1$-$C_4$)-alkyl and ($C_3$-$C_7$)-cycloalkyl;

R20 is selected from the series consisting of hydrogen, ($C_1$-$C_8$)-alkyl, ($C_3$-$C_7$)-cycloalkyl, —($C_1$-$C_4$)-alkyl-($C_3$-$C_7$)-cycloalkyl, phenyl, —($C_1$-$C_4$)-alkyl-phenyl, Het and —($C_1$-$C_4$)-alkyl-Het, wherein phenyl and Het all are unsubstituted or substituted by one or more identical or different substituents R30, or R19 and R20, together with the nitrogen atom carrying them, form a monocyclic, 4-membered to 7-membered, saturated heterocycle which, in addition to the nitrogen atom carrying R19 and R20, comprises 0 or 1 further ring heteroatom selected from the series consisting of nitrogen, oxygen and sulfur, and which is unsubstituted or substituted by one or more identical or different substituents selected from the series consisting of fluorine and ($C_1$-$C_4$)-alkyl;

R21 is selected from the series consisting of hydrogen, ($C_1$-$C_4$)-alkyl and ($C_3$-$C_7$)-cycloalkyl;

R22 is selected from the series consisting of ($C_1$-$C_4$)-alkyl, ($C_3$-$C_7$)-cycloalkyl and —($C_1$-$C_4$)-alkyl-($C_3$-$C_7$)-cycloalkyl;

R23 and R24 are independently of one another selected from the series consisting of hydrogen and ($C_1$-$C_4$)-alkyl;

R30 is selected from the series consisting of halogen, ($C_1$-$C_4$)-alkyl, —O—($C_1$-$C_4$)-alkyl and —CN;

Het is a monocyclic, 4-membered to 7-membered, saturated, partially unsaturated or aromatic heterocycle which comprises 1 or 2 identical or different ring heteroatoms selected from the series consisting of nitrogen, oxygen and sulfur, and which is bonded via a ring carbon atom;

wherein all cycloalkyl groups can be substituted by one or more identical substituents selected from the series consisting of fluorine and ($C_1$-$C_4$)-alkyl;

wherein all alkyl groups, independently of any other substituents which can be present on an alkyl group, can be substituted by one or more fluorine substituents.

If structural elements such as groups, substituents or numbers, for example, can occur several times in the compounds of the formula I, they are all independent of each other and can in each case have any of the indicated meanings, and they can in each case be identical to or different from any other such element. In a dialkylamino group, for example, the alkyl groups can be identical or different.

Alkyl groups, i.e. saturated hydrocarbon residues, can be linear (straight-chain) or branched. This also applies if these groups are substituted or are part of another group, for example an —O-alkyl group (alkyloxy group, alkoxy group) or an HO-substituted alkyl group (-alkyl-OH, hydroxyalkyl group). Depending on the respective definition, the number of carbon atoms in an alkyl group can be 1, 2, 3, 4, 5, 6, 7 or 8, 1, 2, 3, 4, 5 or 6, or 1, 2, 3 or 4, or 1, 2 or 3, or 1 or 2, or 1. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, hexyl including n-hexyl, 2,2,-dimethylhexyl, 3,3-dimethylbutyl, 2-methylpentyl, 3-methylpentyl and isohexyl, heptyl including n-heptyl, and octyl including n-octyl. Examples of —O-alkyl groups are methoxy, ethoxy, n-propoxy, isopropoxy, n-butoxy, isobutoxy, tert-butoxy, n-pentoxy.

A substituted alkyl group can be substituted in any positions, provided that the respective compound is sufficiently stable and is suitable as a pharmaceutical active compound. The prerequisite that a specific group and a compound of the formula I are sufficiently stable and suitable as a pharmaceutical active compound, applies in general with respect to the definitions of all groups in the compounds of the formula I. An alkyl group which, independently of any other substituents, can be substituted by one or more fluorine substituents, can be unsubstituted by fluorine substituents, i.e. not carry fluorine substituents, or substituted, for example by 1, 2, 3, 4, 5, 6, 7, 8, 9, 10 or 11 fluorine substituents, or by 1, 2, 3, 4 or 5 fluorine substituents, or by 1, 2 or 3 fluorine substituents, which can be located in any positions. For example, in a fluoro-substituted alkyl group one or more methyl groups can carry three fluorine substituents each and be present as trifluoromethyl groups, and/or one or more methylene groups ($CH_2$) can carry two fluorine substituents each and be present as difluoromethylene groups. The explanations with respect to the substitution of a group by fluorine also apply if the group additionally carries other substituents and/or is part of another group, for example of an —O-alkyl group. Examples of fluoro-substituted alkyl groups are —$CF_3$ (trifluoromethyl), —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$C_H2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$. Examples of fluoro-substituted —O-alkyl groups are trifluoromethoxy (—$OCF_3$), 2,2,2-trifluoroethoxy, pentafluoroethoxy and 3,3,3-trifluoropropoxy. With respect to all groups or substituents in the compounds of the formula I which can be an alkyl group which can generally contain one or more fluorine substituents, as an example of groups or substituents containing fluorine-substituted alkyl which may be included in the definition of the group or substituent, the group $CF_3$ (trifluoromethyl), or a respective group such as $CF_3$—O—, may be mentioned.

The above explanations with respect to alkyl groups apply correspondingly to alkyl groups which in the definition of a group in the compounds of the formula I are bonded to two adjacent groups, or linked to two groups, and may be regarded as divalent alkyl groups (alkanediyl groups), like in the case of the alkyl part of a substituted alkyl group. Thus, such groups can also be linear or branched, the bonds to the adjacent groups can be located in any positions and can start from the same carbon atom or from different carbon atoms, and they can be unsubstituted or substituted by fluorine substituents independently of any other substituents. Examples of such divalent alkyl groups are —$CH_2$—, —$CH_2$—$CH_2$—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, —CH($CH_3$)-, —C($CH_3$)$_2$-, —CH($CH_3$)-$CH_2$-, —$CH_2$—CH($CH_3$)-, —C($CH_3$)$_2$—$CH_2$—, —$CH_2$—C($CH_3$)$_2$—. Examples of fluoro-substituted alkanediyl groups, which can contain 1, 2, 3, 4, 5 or 6 fluorine substituents, or 1, 2, 3 or 4 fluorine substituents, or 1 or 2 fluorine substituents, for example, are —$CF_2$—, —CHF—, —CHF—$CHF_2$—, —CHF—CHF—, —$CH_2$—$CF_2$—, —$CH_2$—CHF—, —$CF_2$—$CF_2$—, —$CF_2$—CHF—, —$CH_2$—CHF—$CF_2$—, —$CH_2$—CHF—CHF—, —$CH_2$—$CH_2$—$CF_2$—, —$CH_2$—$CH_2$—CHF, —$CH_2$—$CF_2$—$CF_2$—, —$CH_2$—$CF_2$—CHF—, —CHF—CHF—$CF_2$—, —CHF—CHF—CHF—, —CHF—$CH_2$—$CF_2$—, —CHF—$CH_2$—CHF—, —CHF—$CF_2$—$CF_2$—, —CHF—$CF_2$—CHF—, —$CF_2$—CHF—$CF_2$—, —$CF_2$—CHF—CHF—, —$CF_2$—$CH_2$—$CF_2$—, —$CF_2$—$CH_2$—CHF—, —$CF_2$—$CF_2$—$CF_2$—, or —$CF_2$—$CF_2$—CHF.

The number of ring carbon atoms in a ($C_3$-$C_7$)-cycloalkyl group can be 3, 4, 5, 6 or 7. Examples of cycloalkyl are cyclopropyl, cyclobutyl, cyclopentyl, cyclohexyl and cycloheptyl. Cycloalkyl which, independently of any other substituents, can be substituted by one or more ($C_1$-$C_4$)-alkyl substituents, can be unsubstituted by alkyl substituents, i.e. not carry alkyl substituents, or substituted, for example by 1, 2, 3 or 4 identical or different ($C_1$-$C_4$)-alkyl substituents, for example by methyl groups, which substituents can be located in any positions. Examples of such alkyl-substituted cycloalkyl groups are 1-methylcyclopropyl, 2,2-dimethylcyclopropyl, 1-methylcyclopentyl, 2,3-dimethylcyclopentyl, 1-methylcyclohexyl, 4-methylcyclohexyl, 4-isopropylcyclohexyl, 4-tert-butylcyclohexyl, 3,3,5,5-tetramethylcyclohexyl. Cycloalkyl groups which, independently of any other substituents, can be substituted by one or more fluorine substituents, can be unsubstituted by fluorine substituents, i.e. not carry fluorine substituents, or substituted, for example by 1, 2, 3, 4, 5, 6, 7, 8, 9, 10 or 11 fluorine substituents, or by 1, 2, 3, 4, 5 or 6 fluorine substituents, or by 1, 2 or 3 fluorine substituents. The fluorine substituents can be located in any positions of the cycloalkyl group and can also be located in an alkyl substituent. Examples of fluoro-substituted cycloalkyl groups are 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl. Cycloalkyl groups can also be substituted simultaneously by fluorine and alkyl. Examples of the group —($C_1$-$C_4$)-alkyl-($C_3$-$C_7$)-cycloalkyl are cyclopropylmethyl-, cyclobutylmethyl-, cyclopentylmethyl-, cyclohexylmethyl-, cycloheptylmethyl-, 1-cyclopropylethyl-, 2-cyclopropylethyl-, 1-cyclobutylethyl-, 2-cyclobutylethyl-, 1-cyclopentylethyl-, 2-cyclopentylethyl-, 1-cyclohexylethyl-, 2-cyclohexylethyl-, 1-cycloheptylethyl-, 2-cycloheptylethyl-. In one embodiment of the invention, a —($C_1$-$C_4$)-alkyl-($C_3$-$C_7$)-cycloalkyl group in any one or more occurrences of such a group, independently of any other occurrences, is a —($C_1$-$C_2$)-alkyl-($C_3$-$C_7$)-cycloalkyl group, in another embodiment a —$CH_2$—($C_3$-$C_7$)-cycloalkyl group. In the group —($C_1$-$C_4$)-alkyl-($C_3$-$C_7$)-cycloalkyl, and likewise in all other groups, the terminal hyphen denotes the free bond via which the group is bonded, and thus indicates via which subgroup a group composed of subgroups is bonded.

In substituted phenyl groups, including phenyl groups representing Ar, the substituents can be located in any positions. In monosubstituted phenyl groups, the substituent can be located in position 2, in position 3 or in position 4. In disubstituted phenyl groups, the substituents can be located in positions 2 and 3, in positions 2 and 4, in positions 2 and 5, in positions 2 and 6, in positions 3 and 4, or in positions 3 and 5. In trisubstituted phenyl groups, the substituents can be located in positions 2, 3 and 4, in positions 2, 3 and 5, in positions 2, 3 and 6, in positions 2, 4 and 5, in positions 2, 4 and 6, or in positions 3, 4 and 5. If a phenyl group carries four substituents, some of which can be fluorine atoms, for example, the substituents can be located in positions 2, 3, 4 and 5, in positions 2, 3, 4 and 6, or in positions 2, 3, 5 and 6. If a polysubstituted phenyl group or any other polysubstituted group carries different substituents, each substituent can be located in any suitable position, and the present invention comprises all positional isomers. The number of substituents in a substituted phenyl group can be 1, 2, 3, 4 or 5. In one embodiment of the invention, the number of substituents in a substituted phenyl group, like the number of substituents in any other substituted group which can carry one or more substituents, for example the group Het, is 1, 2, 3 or 4, in another embodiment 1, 2 or 3, in another embodiment 1 or 2, in another embodiment 1, where the number of substituents in any occurrence of such a substituted group is independent of the number of substituents in other occurrences.

In heterocyclic groups, including the group Het, heterocycles representing Ar and other heterocyclic rings which can be present in the compounds of the formula I, such as rings formed by two group together with the atom or atoms carrying them, the hetero ring members can be present in any combination and located in any suitable ring positions, provided that the resulting group and the compound of the formula I are suitable and sufficiently stable as a pharmaceutical active compound. In one embodiment of the invention, two oxygen atoms in any heterocyclic ring in the compounds of the formula I cannot be present in adjacent ring positions. In another embodiment of the invention, two hetero ring members selected from the series consisting of oxygen atoms and sulfur atoms cannot be present in adjacent ring positions in any heterocyclic ring in the compounds of the formula I. In another embodiment of the invention, two hetero ring members selected from the series consisting of nitrogen atoms carrying an exocyclic group like a hydrogen atom or a substituent, sulfur atoms and oxygen atoms cannot be present in adjacent ring positions in any heterocyclic ring in the compounds of the formula I. The choice of hetero ring members in an aromatic heterocyclic ring is limited by the prerequisite that the ring is aromatic, i.e. it comprises a cyclic system of six delocalized pi electrons. Monocyclic aromatic heterocycles are 5-membered or 6-membered rings and, in the case of a 5-membered ring, comprise one ring heteroatom selected from the series consisting of oxygen, sulfur and nitrogen, wherein this ring nitrogen carries an exocyclic group like a hydrogen atom or a substituent, and optionally one or more further ring nitrogen atoms, and, in the case of a 6-membered ring, comprise one or more nitrogen atoms as ring heteroatoms, but no oxygen atoms and sulfur atoms as ring heteroatoms. Heterocyclic groups in the compounds of the formula I are bonded via a ring carbon atom or a ring nitrogen atom, as specified in the definition of the respective group, where a heterocyclic group can be bonded via any suitable carbon atom or nitrogen atom, respectively, in the ring. In substituted heterocyclic groups, the substituents can be located in any positions.

The number of ring heteroatoms which can be present in a heterocyclic group in the compounds of the formula I, the number of ring members which can be present, and the degree of saturation, i.e. whether the heterocyclic group is saturated and does not contain a double bond within the ring, or whether it is partially unsaturated and contains one or more, for example one or two, double bonds within the ring but is not aromatic, or whether it is aromatic and thus contains two double bonds within the ring in the case of a 5-membered monocyclic aromatic heterocycle and three double bonds within the ring in the case of a 6-membered monocyclic aromatic heterocycle, is specified in the definitions of the individual groups in the compounds of the formula I. As examples of heterocyclic ring systems, from which heterocyclic groups in the compounds of the formula I including the bicyclic heterocyclic ring system which can result in case two groups R10 bonded to adjacent ring carbon atoms in Ar together with the carbon atoms carrying them form a ring, can be derived, and from any one or more of which any of the heterocyclic groups in the compounds of the formula I is selected in one embodiment of the invention, provided that the ring system is comprised by the definition of the group, oxetane, thietane, azetidine, furan, tetrahydrofuran, thiophene, tetrahydrothiophene, pyrrole, pyrroline, pyrrolidine, 1,3-dioxole, 1,3-dioxolane, isoxazole ([1,2]oxazole), isoxazoline, isoxazolidine, oxazole ([1,3]oxazole), oxazoline, oxazolidine, isothiazole ([1,2]thiazole), isothiazoline, isothiazolidine, thiazole ([1,3]thiazole), thiazoline, thiazolidine, pyrazole, pyrazoline, pyrazolidine, imidazole, imidazoline, imidazolidine, [1,2,3]triazole, [1,2,4]triazole, [1,2,4]oxadiazole, [1,3,4]oxadiazole, 1,2,5-oxadiazole, [1,2,4]thiadiazole, pyran, tetrahydropyran, thiopyran, tetrahydrothiopyran, 2,3-dihydro[1,4]dioxine, 1,4-dioxane, pyridine, 1,2,5,6-tetrahydropyridine, piperidine, morpholine, thiomorpholine, piperazine, pyridazine, pyrimidine, pyrazine, [1,2,4]triazine, oxepane, thiepane, azepane, [1,3]diazepane, [1,4]diazepane, [1,4]oxazepane, [1,4]thiazepane, benzofuran, isobenzofuran, benzothiophene (benzo[b]thiophene), 1H-indole, 2,3-dihydro-1H-indole, 2H-isoindole, benzo[1,3]dioxole, benzoxazole, benzthiazole, 1H-benzimidazole, chroman, isochroman, thiochroman, benzo[1,4]dioxane, 3,4-dihydro-2H-benzo[1,4]oxazine, 3,4-dihydro-2H-benzo[1,4]thiazine, quinoline, 5,6,7,8-tetrahydroquinoline, isoquinoline, 5,6,7,8-tetrahydroisoquinoline, cinnoline, quinazoline, quinoxaline, phthalazine, [1,8]naphthyridine and 3,4-dihydro-2H-benzo[b][1,4]dioxepine, which latter ring system may also be named as 3,4-dihydro-2H-1,5-benzodioxepine, may be mentioned, which can all be unsubstituted or substituted in any suitable positions as specified in the definition of the respective group in the compounds of the formula I, wherein the given degree of unsaturation is by way of example only, and in the individual groups also ring systems with a higher or lower degree of saturation, or hydrogenation, or of unsaturation can be present as specified in the definition of the group. Ring sulfur atoms, in particular in saturated and partially unsaturated heterocycles, can generally carry one or two oxo groups, i.e. doubly bonded oxygen atoms, and in such heterocycles, besides a ring sulfur atom, also an S(O) group (S(=O)) and an S(O)$_2$ group (S(=O)$_2$) can be present as hetero ring member.

As mentioned, the heterocyclic groups can be bonded via any suitable ring atom as specified in the definition of the respective group in the compound of the formula I. For example, among others can an oxetane and a thietane ring be bonded via positions 2 and 3, an azetidine ring via positions 1, 2 and 3, a furan ring, a tetrahydrofuran ring, a thiophene ring and a tetrahydrothiophene via positions 2 and 3, a pyrrole ring and a pyrrolidine ring via positions 1, 2 and 3, an isoxazole ring and an isothiazole ring via positions 3, 4 and 5, a pyrazole ring via positions 1, 3, 4 and 5, an oxazole ring and a thiazole ring via positions 2, 4 and 5, an imidazole ring and an imidazolidine ring via positions 1, 2, 4 and 5, a tetrahydropyran and a tetrahydrothiopyran ring via positions 2, 3 and 4, a 1,4-dioxane ring via position 2, a pyridine ring via positions 2, 3 and 4, a piperidine ring via positions 1, 2, 3 and 4, a morpholine ring and a thiomorpholine ring via positions 2, 3 and 4, a piperazine ring via positions 1 and 2, a pyrimidine ring via positions 2, 4 and 5, a pyrazine ring via position 2, an azepane ring via positions 1, 2, 3 and 4, a benzofuran ring and a benzothiophene ring via positions 2, 3, 4, 5, 6 and 7, a 1H-indole ring and a 2,3-dihydro-1H-indole ring via positions 1, 2, 3, 4, 5, 6 and 7, a benzo[1,3]dioxole ring via positions 4, 5, 6 and 7, a benzoxazole ring and a benzthiazole ring via positions 2, 4, 5, 6 and 7, a 1H-benzimidazole ring via positions 1, 2, 4, 5, 6 and 7, a benzo[1,4]dioxane ring via positions 5, 6, 7 and 8, a quinoline ring via positions 2, 3, 4, 5, 6, 7 and 8, a 5,6,7,8-tetrahydroquinoline via positions 2, 3 and 4, an isoquinoline ring via positions 1, 3, 4, 5, 6, 7 and 8, a 5,6,7,8-tetrahydroisoquinoline ring via positions 1, 3 and 4, for example, wherein the resulting residues of the heterocyclic groups can all be unsubstituted or substituted in any suitable positions as specified in the definition of the respective group in the compounds of the formula I.

Halogen is fluorine, chlorine, bromine or iodine. In one embodiment of the invention, halogen is in any of its occurrences fluorine, chlorine or bromine, in another embodiment fluorine or chlorine, in another embodiment fluorine, in another embodiment chlorine, where all occurrences of halogen are independent of each other.

The present invention comprises all stereoisomeric forms of the compounds of the formula I, for example all enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formula I can all independently of each other have S configuration or R configuration. The invention relates to enantiomers, both the levorotatory and the dextrorotatory antipode, in enantiomerically pure form and essentially enantiomerically pure form, and in the form of their racemate, i.e. a mixture of the two enantiomers in molar ratio of 1:1, and in the form of mixtures of the two enantiomers in all ratios. The invention likewise relates to diastereomers in the form of pure and essentially pure diastereomers and in the form of mixtures of two or more diastereomers in all ratios. The invention also comprises all cis/trans isomers of the compounds of the formula I in pure form and essentially pure form, and in the form of mixtures of the cis isomer and the trans isomer in all ratios. Cis/trans isomerism can occur in substituted rings. The preparation of individual stereoisomers, if desired, can be carried out by resolution of a mixture according to customary methods, for example, by chromatography or crystallization, or by use of stereochemically uniform starting compounds in the synthesis, or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. For example, in the case of a compound of the formula I containing an asymmetric center the individual enantiomers can be prepared by preparing the racemate of the compound of the formula I and resolving it into the enantiomers by high pressure liquid chromatography on a chiral phase according to standard procedures, or resolving the racemate of any intermediate in the course of its synthesis by such chromatography or by crystallization of a salt thereof with an optically active amine or acid and converting the enantiomers of the intermediate into the enantiomeric forms of the final compound of the formula I, or by performing an enantioselective reaction in the course of the synthesis. The invention also comprises all tautomeric forms of the compounds of the formula I.

Besides the free compounds of the formula I, i.e. compounds in which acidic and basic groups are not present in the form of a salt, the present invention comprises also the physiologically or toxicologically acceptable salts of the compounds of the formula I, especially their pharmaceutically acceptable salts, which can be formed on one or more acidic or basic groups in the compounds of the formula I, for example on basic heterocyclic moieties. The compounds of the formula I may thus be deprotonated on an acidic group by an inorganic or organic base and be used, for example, in the form of the alkali metal salts. Compounds of the formula I comprising at least one basic group may also be prepared and used in the form of their acid addition salts, for example in the form of pharmaceutically acceptable salts with inorganic acids and organic acids, such as salts with hydrochloric acid and thus be present in the form of the hydrochlorides, for example. Salts can in general be prepared from acidic and basic compounds of the formula I by reaction with an acid or base in a solvent or diluent according to customary procedures. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange.

In one embodiment of the invention, an aromatic heterocycle representing the group Ar comprises 1 or 2 identical or different ring heteroatoms, in another embodiment 1 or 2 identical or different ring heteroatoms which are selected from the series consisting of nitrogen and sulfur. In another embodiment, an aromatic heterocycle representing Ar is a 5-membered heterocycle which comprises 1 or 2 identical or different ring heteroatoms which are selected from the series consisting of nitrogen and sulfur, or it is a 6-membered heterocycle which comprises 1 or 2 ring heteroatoms which are nitrogen atoms, in another embodiment it is a 5-membered heterocycle which comprises 1 or 2 identical or different ring heteroatoms which are selected from the series consisting of nitrogen and sulfur. In another embodiment, an aromatic heterocycle representing Ar is selected from the series consisting of thiophene, thiazole, pyrazole, imidazole, pyridine, pyridazine, pyrimidine and pyrazine, in another embodiment from the series consisting of thiophene, thiazole, pyrazole, imidazole and pyridine, in another embodiment from the series consisting of thiophene, thiazole, pyrazole and imidazole, in another embodiment from the series consisting of thiophene and pyrazole, in another embodiment it is thiophene, and in another embodiment it is pyrazole, which heterocycles are all unsubstituted or substituted by one or more substituents R10. In one embodiment of the invention, Ar is phenyl which is unsubstituted or substituted by one or more identical or different substituents R10, in another embodiment Ar is phenyl which is substituted by one or more identical or different substituents R10, in another embodiment Ar is a 5-membered or 6-membered aromatic heterocycle which is unsubstituted or substituted by one or more identical or different substituents R10, and in another embodiment Ar is a 5-membered or 6-membered aromatic heterocycle which is substituted by one or more identical or different substituents R10. In one embodiment of the invention, the number of identical or different substituents R10 which can be present in the group Ar is 1, 2, 3 or 4, in another embodiment it is 1, 2 or 3, in another embodiment it is 1 or 2, in another embodiment it is 1, in another embodiment it 2, 3 or 4, in another embodiment it is 2 or 3, in another embodiment it is 3, in another embodiment it is 2. In one embodiment, Ar is substituted by one or more identical or different substituents R10.

In one embodiment of the invention, the number n is selected from the series consisting of 0 and 1, in another embodiment from the series consisting of 1 and 2, in another embodiment it is 1, in another embodiment it is 0.

In one embodiment of the invention, R1 is selected from the series consisting of hydrogen, —N(R11)-R12, —N(R13)-C(O)—R14, —N(R13)-S(O)$_2$—R15, —N(R13)-C(O)—NH—R14, $(C_1-C_4)$-alkyl and —$(C_1-C_4)$-alkyl-O—R18, in another embodiment from the series consisting of hydrogen, —N(R11)-R12, —N(R13)-C(O)—R14, —N(R13)-S(O)$_2$—R15, —N(R13)-C(O)—NH—R14, —C(O)—N(R16)-R17, —CN and (C$_1$-C$_4$)-alkyl, in another embodiment from the series consisting of hydrogen, —N(R11)-R12, —N(R13)-C(O)—R14, —N(R13)-S(O)$_2$—R15, —N(R13)-C(O)—NH—R14 and (C$_1$-C$_4$)-alkyl, in another embodiment from the series consisting of hydrogen, —C(O)—N(R16)-R17, —CN, (C$_1$-C$_4$)-alkyl and —(C$_1$-C$_4$)-alkyl-O—R18, in another embodiment from the series consisting of hydrogen and (C$_1$-C$_4$)-alkyl, in another embodiment from the series consisting of —N(R11)-R12, —N(R13)-C(O)—R14, —N(R13)-S(O)$_2$—R15 and —N(R13)-C(O)—NH—R14, in another embodiment from the series consisting of —N(R11)-R12 and —N(R13)-C(O)—R14, in another embodiment it is —N(R11)-R12, and in another embodiment R1 is selected from the series consisting of —N(R11)-R12 and (C$_1$-C$_4$)-alkyl. In one embodiment, a (C$_1$-C$_4$)-alkyl group representing R1 is (C$_1$-C$_2$)-alkyl, in another embodiment it is methyl.

In one embodiment of the invention, R2 is selected from the series consisting of halogen, (C$_1$-C$_4$)-alkyl and —CN, in another embodiment from the series consisting of halogen and (C$_1$-C$_4$)-alkyl, in another embodiment from the series consisting of halogen and —CN, in another embodiment from the series consisting of halogen. In one embodiment, a (C$_1$-C$_4$)-alkyl group present in R2 is a methyl group. In one embodiment, halogen representing R2 is selected from the series consisting of fluorine and chlorine, in another embodiment it is fluorine. Ring carbon atoms in the divalent phenyl group depicted in formula I which have a free binding site, i.e. are not bonded to adjacent groups in formula I, and which do not carry a group R2, carry hydrogen atoms, as does likewise the carbon atom in position 5 of the pyrazolo[3,4-b]pyrazine ring system depicted in formula I. Thus, in case the number n is 0 and hence no group R2 is present, all four carbon atoms in the ring positions of the divalent phenyl group depicted in formula I which in formula I' are designated as positions 2', 3', 5' and 6', carry hydrogen atoms. In case the number n is 1 and hence one group R2 is present, one of the four carbon atoms in the ring positions of the divalent phenyl group depicted in formula I which in formula I' are designated as 2', 3', 5' and 6', carries the group R2 and the other three said carbon atoms carry hydrogen atoms. In case the number n is 2 and hence two groups R2 are present, two of the four carbon atoms in the ring positions of the divalent phenyl group depicted in formula I which in formula I' are designated as positions 2', 3', 5' and 6', carry the groups R2 and the other two said carbon atoms carry hydrogen atoms.

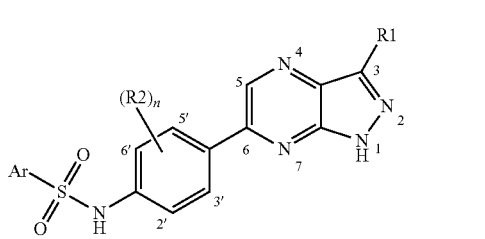

I'

Groups R2 can be present in any positions of the divalent phenyl group depicted in formula I which have a free binding site. If one group R2 is present, in one embodiment of the invention the group R2 is present in the position which is formula I' is designated as position 2', which is equivalent to position 6', and in another embodiment it is present in the position which in formula I' is designated as position 3', which is equivalent to position 5'. If two groups R2 are present, in one embodiment of the invention the groups R2 are present in the positions which in formula I' are designated as positions 2' and 3', in another embodiment in the positions which in formula I' are designated as positions 2' and 5', in another embodiment in the positions which in formula I' are designated as positions 2' and 6', in another embodiment in the positions which in formula I' are designated as positions 3' and 5'.

If two groups R10 bonded to adjacent ring carbon atoms in Ar together with the ring carbon atoms carrying them form a 5-membered to 8-membered ring, this ring is at least mono-unsaturated, i.e., the resulting ring contains at least one double bond within the ring, which double bond is present between the said two adjacent ring carbon in the aromatic ring Ar which are common to the ring Ar and the ring formed by the two groups R10, and because of the rules of nomenclature for fused rings is regarded as a double bond present in both rings. The ring formed by two groups R10 together with the carbon atoms carrying them can contain 1, 2 or 3 double bonds within the ring. In one embodiment, the formed ring contains 1 or 2 double bonds, in another embodiment 1 double bond within the ring. In the case of a 6-membered carbocyclic or heterocyclic ring or a 5-membered heterocyclic ring the formed ring can be aromatic and, together with the aromatic ring Ar, form a bicyclic aromatic ring system, for example a naphthalene ring system, a quinoline ring system, an isoquinoline ring system or a benzothiophene ring system. The case that two groups R10 bonded to adjacent ring carbon atoms in Ar together with the carbon atoms carrying them form a 5-membered to 8-membered unsaturated ring, can in other terms be regarded as two groups R10 together forming a divalent residue comprising a chain of 3 to 6 atoms of which 0, 1 or 2 are identical or different heteroatoms selected from the series consisting of nitrogen, oxygen and sulfur, the terminal atoms of which are bonded to the two adjacent ring carbon atoms in Ar. Examples of such divalent residues, from any one or more of which two groups R10 bonded to adjacent ring carbon atoms in Ar are selected in one embodiment of the invention, are the residues —CH$_2$—CH$_2$—CH$_2$—, —CH$_2$—CH$_2$—CH$_2$—CH$_2$—, —CH$_2$—CH$_2$—CH$_2$—CH$_2$—CH$_2$—, —CH=CH—CH=CH—, —N=CH—CH=CH—, —CH=CH—CH=N—, —CH=N—CH=CH—, —CH=CH—N=CH—, —O—CH$_2$—CH$_2$—, —CH$_2$—CH$_2$—O—, —O—CH$_2$—O—, —O—CH$_2$—CH$_2$—O—, —O—CH$_2$—CH$_2$—CH$_2$—O—, —O—CH$_2$—CH$_2$—CH$_2$—CH$_2$—O—, —S—CH=CH—, —CH=CH—S—, =CH—S—CH=, —N=CH—S—, —S—CH=N—, —N=CH—O—, —O—CH=N—, —NH—CH$_2$—CH$_2$—O—, —O—CH$_2$—CH$_2$—NH—, —S—CH$_2$—CH$_2$—NH— and —NH—CH$_2$—CH$_2$—S—, which can all be substituted by substituents selected from the series consisting of halogen, (C$_1$-C$_4$)-alkyl- —O—(C$_1$-C$_4$)-alkyl and —CN, and can thus also be present, for example, as the divalent residues —O—CF$_2$—O—, —O—C(CH$_3$)$_2$—O—, —S—C(Cl)=CH—, —CH=C(Cl)—S—, —N(CH$_3$)-CH$_2$—CH$_2$—O—, —O—CH$_2$—CH$_2$—N(CH$_3$)-, —S—CH$_2$—CH$_2$—N(CH$_3$)- and —N(CH$_3$)-CH$_2$—CH$_2$—S—. In one embodiment of the invention, the ring heteroatoms which are optionally present in a ring formed by two groups R10 bonded to adjacent ring carbon atoms in Ar together with the carbon atoms carrying them, are selected from the series consisting of nitrogen and oxygen, in another embodiment from the series consisting of oxygen and sulfur, and in another embodiment they are oxygen atoms. In one embodiment of the invention, the ring which can be formed by two groups R10 bonded to adjacent ring carbon atoms in Ar together with the ring carbon atoms carrying them, is a 5-membered to 7-membered, in another embodiment a 5-membered to 6-membered, in another embodiment a 6-membered to 7-membered, in another embodiment a 5-membered, in another embodiment a 6-membered ring, in another embodiment a 7-membered ring. In one embodiment of the invention, the ring which can be formed by two groups R10 bonded to adjacent carbon atoms in Ar together with the carbon atoms carrying them, comprises O ring heteroatoms, i.e. it is a carbocyclic ring, and in another embodiment it comprises 1 or 2 identical or different ring heteroatoms. In one embodiment of the invention, the number of substituents which can be present in a ring formed by two groups R10 bonded to adjacent ring carbon atoms in Ar together with the carbon atoms carrying them, is 1, 2, 3 or 4, in another embodiment 1, 2 or 3, in another embodiment 1 or 2, in another embodiment 1, in another embodiment it is 0. In one embodiment of the invention, substituents which can be present in a ring formed by two groups R10 bonded to adjacent ring carbon atoms in Ar together with the carbon atoms carrying them, are selected from the series consisting of halogen, $(C_1-C_4)$-alkyl and —CN, in another embodiment from the series consisting of halogen and $(C_1-C_4)$-alkyl, and in another embodiment are substituents in such a ring bonded to a ring nitrogen atom selected from the series consisting of $(C_1-C_4)$-alkyl.

In one embodiment of the invention, R10 is selected from the series consisting of halogen, $(C_1-C_4)$-alkyl, $(C_3-C_7)$-cycloalkyl, —$(C_1-C_4)$-alkyl-$(C_3-C_7)$-cycloalkyl, —O—$(C_1-C_4)$-alkyl, —O—$(C_3-C_7)$-cycloalkyl, —O—$(C_1-C_4)$-alkyl-$(C_3-C_7)$-cycloalkyl-, —N(R19)-R20, —N(R21)-N(R19)-R20, —N(R21)-C(O)—R22, —NO$_2$ and —CN, in another embodiment from the series consisting of halogen, $(C_1-C_4)$-alkyl, —O—$(C_1-C_4)$-alkyl, —N(R19)-R20, —N(R21)-N(R19)-R20, —N(R21)-C(O)—R22, —NO$_2$, —C(O)—N(R23)-R24 and —CN, in another embodiment from the series consisting of halogen, $(C_1-C_4)$-alkyl, —O—$(C_1-C_4)$-alkyl, —N(R19)-R20, —N(R21)-N(R19)-R20, —N(R21)-C(O)—R22, —NO$_2$ and —CN, in another embodiment from the series consisting of halogen, $(C_1-C_4)$-alkyl, —O—$(C_1-C_4)$-alkyl, —N(R19)-R20, —N(R21)-C(O)—R22, —NO$_2$ and —CN, in another embodiment from the series consisting of halogen, $(C_1-C_4)$-alkyl, —O—$(C_1-C_4)$-alkyl, —N(R19)-R20, —N(R21)-C(O)—R22 and —CN, in another embodiment from the series consisting of halogen, $(C_1-C_4)$-alkyl, —O—$(C_1-C_4)$-alkyl, —N(R21)-C(O)—R22, —NO$_2$ and —CN, in another embodiment from the series consisting of halogen, $(C_1-C_4)$-alkyl, —O—$(C_1-C_4)$-alkyl, —N(R21)-C(O)—R22 and —CN, in another embodiment from the series consisting of halogen, $(C_1-C_4)$-alkyl, —O—$(C_1-C_4)$-alkyl, —NO$_2$ and —CN, in another embodiment from the series consisting of halogen, $(C_1-C_4)$-alkyl, —O—$(C_1-C_4)$-alkyl and —CN, in another embodiment from the series consisting of halogen, $(C_1-C_4)$-alkyl and —CN, in another embodiment from the series consisting of halogen and $(C_1-C_4)$-alkyl, and in another embodiment from the series consisting of halogen.

In one embodiment, substituents R10 which are bonded to a ring nitrogen atom in Ar, such as in the case of a pyrrole, pyrazole or imidazole ring representing Ar, are selected from the series consisting of $(C_1-C_4)$-alkyl, $(C_3-C_7)$-cycloalkyl, —$(C_1-C_4)$-alkyl-$(C_3-C_7)$-cycloalkyl and —C(O)—N(R23)-R24, in another embodiment from the series consisting of $(C_1-C_4)$-alkyl, $(C_3-C_7)$-cycloalkyl and —$(C_1-C_4)$-alkyl-$(C_3-C_7)$-cycloalkyl, in another embodiment from the series consisting of $(C_1-C_4)$-alkyl.

In one embodiment of the invention, a $(C_1-C_4)$-alkyl group which represents R10 or is present in the group —O—$(C_1-C_4)$-alkyl representing R10, is a $(C_1-C_3)$-alkyl group, in another embodiment a $(C_1-C_2)$-alkyl group, in another embodiment a methyl group, where all these alkyl groups can optionally be substituted by fluorine substituents as applies to alkyl groups in general, and also occur as a trifluoromethyl group, for example. In one embodiment of the invention, a $(C_3-C_7)$-cycloalkyl group which represents R10 or is present in a group R10, is a $(C_3-C_6)$-cycloalkyl group, in another embodiment a $(C_3-C_4)$-cycloalkyl group, in another embodiment a cyclopropyl group. In on embodiment of the invention, the total number of —NO$_2$ (nitro) groups representing R10 in a compound of the formula I is not greater than 2, in another embodiment it is not greater than 1.

Examples of groups Ar including the optional substituents R10 on Ar, from any one or more of which Ar is selected in one embodiment of the invention, are 2,3-dichloro-phenyl, 2,5-dichloro-phenyl, 5-chloro-2-hydrazino-phenyl, 5-chloro-2-cyano-phenyl, 2-cyano-5-methyl-phenyl, 2-fluoro-5-methyl-phenyl, 2-chloro-5-methoxy-phenyl, 2,5-dichloro-thiophen-3-yl, 8-chloro-3,4-dihydro-2H-benzo[b][1,4]dioxepin-7-yl, 5-chloro-1,3-dimethyl-pyrazol-4-yl, naphthalen-1-yl, 2,4,6-trichloro-phenyl, 5-chloro-2-fluoro-phenyl, 2,4,5-trifluoro-phenyl), 2,4,5-trichloro-phenyl, 5-chloro-2,4-difluoro-phenyl, 2,3,4-trichloro-phenyl, 2,3,4-trifluoro-phenyl, 2-chloro-4-trifluoromethyl-phenyl, 5-cyano-2-fluoro-phenyl, 2-cyano-5-methoxy-phenyl, 2-cyano-5-fluoro-phenyl, 2-fluoro-5-methoxy-phenyl, 4-acetylamino-2-methyl-phenyl, 2-methyl-5-nitro-phenyl, and 2-nitro-4-trifluoromethyl-phenyl.

The monocyclic heterocycle which can be formed by the groups R11 and R12 together with the nitrogen atom carrying them, which heterocycle is thus bonded via a ring nitrogen atom, can be 4-membered, 5-membered, 6-membered or 7-membered. In one embodiment of the invention, the heterocycle formed by the groups R11 and R12 together with the nitrogen atom carrying them, is 4-membered to 6-membered, in another embodiment it is 5-membered or 6-membered, in another embodiment it is 6-membered. In one embodiment, the further ring heteroatom which is optionally present in a heterocycle formed by the groups R11 and R12 together with the nitrogen atom carrying them, is selected from the series consisting of nitrogen and oxygen, in another embodiment it is a nitrogen atom, and in another embodiment it is an oxygen atom, and in another embodiment no further ring heteroatom is present. In one embodiment of the invention, the number of substituents selected from the series consisting of fluorine and $(C_1-C_4)$-alkyl, which can be present in a ring formed by the groups R11 and R12 together with the nitrogen atom carrying them, is 1, 2 or 3, in another embodiment 1 or 2, in another embodiment 1. In one embodiment of the invention, substituents which can be present in a ring formed by the groups R11 and R12 together with the nitrogen atom carrying them, are fluorine substituents, and in another embodiment they are $(C_1-C_4)$-alkyl substituents, for example methyl substituents, and in another embodiment are substituents in such a ring bonded to a ring nitrogen atom selected from the series consisting of $(C_1-C_4)$-alkyl. Examples of heterocyclic groups, from any one or more of which the heterocyclic groups formed by the groups R11 and R12 together with the nitrogen atom carrying them is selected in one embodiment of the invention, are azetidin-1-yl, pyrrolidin-1-yl, piperidin-1-yl, morpholin-4-yl, thiomorpholin-4-yl, and 4-methylpiperazin-1-yl.

In one embodiment of the invention, one of the groups R11 and R12 is selected from the series consisting of hydrogen and $(C_1-C_4)$-alkyl, and the other is selected from the series consisting of hydrogen, $(C_1-C_4)$-alkyl, $(C_3-C_7)$-cycloalkyl and $—(C_1-C_4)$-alkyl-$(C_3-C_7)$-cycloalkyl, in another embodiment R11 and R12 are independently of one another selected from the series consisting of hydrogen, $(C_1-C_4)$-alkyl and $(C_3-C_7)$-cycloalkyl, in another embodiment from the series consisting of hydrogen and $(C_1-C_4)$-alkyl, in another embodiment from the series consisting of $(C_1-C_4)$-alkyl, and in another embodiment they are hydrogen, i.e., in this latter embodiment the group —N(R11)-R12 representing R1 is the group —NH$_2$ (amino), or in all these embodiments R11 and R12, together with the nitrogen atom carrying them, form a monocyclic, 4-membered to 7-membered, saturated heterocycle which, in addition to the nitrogen atom carrying R11 and R12, comprises 0 or 1 further ring heteroatom selected from the series consisting of nitrogen, oxygen and sulfur, and which is unsubstituted or substituted by one or more identical or different substituents selected from the series consisting of fluorine and $(C_1-C_4)$-alkyl.

In one embodiment of the invention, one of the groups R11 and R12 is selected from the series consisting of hydrogen and $(C_1-C_4)$-alkyl, and the other is selected from the series consisting of hydrogen, $(C_1-C_4)$-alkyl, $(C_3-C_7)$-cycloalkyl and $—(C_1-C_4)$-alkyl-$(C_3-C_7)$-cycloalkyl, In another embodiment, R11 and R12 are independently of one another selected from the series consisting of hydrogen, $(C_1-C_4)$-alkyl and $(C_3-C_7)$-cycloalkyl, in another embodiment from the series consisting of hydrogen and $(C_1-C_4)$-alkyl, in another embodiment from the series consisting of $(C_1-C_4)$-alkyl, and in another embodiment R11 and R12 are hydrogen.

In one embodiment of the invention, R13 is selected from the series consisting of hydrogen and $(C_1-C_4)$-alkyl, in another embodiment from the series consisting of hydrogen and $(C_1-C_3)$-alkyl, in another embodiment from the series consisting of hydrogen and methyl, and in another embodiment R13 is hydrogen.

In one embodiment of the invention, R14 and R15 are independently of one another selected from the series consisting of $(C_3-C_7)$-cycloalkyl, phenyl, $—(C_1-C_4)$-alkyl-phenyl, Het and $—(C_1-C_4)$-alkyl-Het, in another embodiment from the series consisting of $(C_3-C_7)$-cycloalkyl, phenyl, $—(C_1-C_4)$-alkyl-phenyl and Het, in another embodiment from the series consisting of $(C_1-C_8)$-alkyl, $(C_3-C_7)$-cycloalkyl, $—(C_1-C_4)$-alkyl-$(C_3-C_7)$-cycloalkyl, $—(C_1-C_4)$-alkyl-phenyl and $—(C_1-C_4)$-alkyl-Het, in another embodiment from the series consisting of phenyl and Het, and in another embodiment are one or both of R14 and R15 independently of one another selected from the series consisting of $(C_1-C_8)$-alkyl, in another embodiment from the series consisting of $(C_3-C_7)$-cycloalkyl, in another embodiment from the series consisting of $—(C_1-C_4)$-alkyl-$(C_3-C_7)$-cycloalkyl, in another embodiment from the series consisting of phenyl, in another embodiment from the series consisting of $—(C_1-C_4)$-alkyl-phenyl, in another embodiment from the series consisting of Het, and in another embodiment from the series consisting of $—(C_1-C_4)$-alkyl-Het, wherein in all these embodiments phenyl and Het all are unsubstituted or substituted by one or more identical or different substituents R30.

The explanations given above with respect to a monocyclic ring which can be formed by R11 and R12 together with the nitrogen atom carrying them, and the embodiments specified above with respect to this ring, apply correspondingly to the monocyclic ring which can be formed by R16 and R17 together with the nitrogen atom carrying them. For example, the ring which can be formed by the groups R16 and R17 together with the nitrogen atom carrying them, which heterocycle is thus bonded via a ring nitrogen atom, can be 4-membered, 5-membered, 6-membered or 7-membered. In one embodiment, the further ring heteroatom which is optionally present in a heterocycle formed by the groups R16 and R17 together with the nitrogen atom carrying them, is selected from the series consisting of nitrogen and oxygen, in another embodiment it is a nitrogen atom, and in another embodiment it is an oxygen atom, and in another embodiment no further ring heteroatom is present. In one embodiment of the invention, substituents in a ring formed by the groups R16 and R17 together with the nitrogen atom carrying them, which are bonded to a ring nitrogen atom, are, selected from the series consisting of $(C_1-C_4)$-alkyl. Examples of heterocyclic groups, from any one or more of which the heterocyclic groups formed by the groups R16 and R17 together with the nitrogen atom carrying them is selected in one embodiment of the invention, likewise are azetidin-1-yl, pyrrolidin-1-yl, piperidin-1-yl, morpholin-4-yl, thiomorpholin-4-yl, and 4-methylpiperazin-1-yl.

In one embodiment of the invention, R16 is selected from the series consisting of hydrogen and $(C_1-C_4)$-alkyl, in another embodiment from the series consisting of hydrogen and $(C_1-C_3)$-alkyl, in another embodiment from the series consisting of hydrogen and methyl, and in another embodiment R16 is hydrogen, and in one embodiment R17 is selected from the series consisting of hydrogen, $(C_1-C_8)$-alkyl, $(C_3-C_7)$-cycloalkyl, —$(C_1-C_4)$-alkyl-$(C_3-C_7)$-cycloalkyl, phenyl, —$(C_1-C_4)$-alkyl-phenyl, Het and —$(C_1-C_4)$-alkyl-Het, in another embodiment from the series consisting of hydrogen, $(C_1-C_8)$-alkyl, $(C_3-C_7)$-cycloalkyl, —$(C_1-C_4)$-alkyl-$(C_3-C_7)$-cycloalkyl, —$(C_1-C_4)$-alkyl-phenyl and —$(C_1-C_4)$-alkyl-Het, in another embodiment from the series consisting of hydrogen, $(C_1-C_8)$-alkyl, $(C_3-C_7)$-cycloalkyl, —$(C_1-C_4)$-alkyl-$(C_3-C_7)$-cycloalkyl, phenyl, —$(C_1-C_4)$-alkyl-phenyl and —$(C_1-C_4)$-alkyl-Het, in another embodiment from the series consisting of hydrogen, $(C_1-C_8)$-alkyl, $(C_3-C_7)$-cycloalkyl and —$(C_1-C_4)$-alkyl-$(C_3-C_7)$-cycloalkyl, in another embodiment from the series consisting of hydrogen, $(C_1-C_8)$-alkyl and $(C_3-C_7)$-cycloalkyl, in another embodiment from the series consisting of hydrogen and $(C_1-C_8)$-alkyl, in another embodiment from the series consisting of $(C_1-C_8)$-alkyl, and in another embodiment R17 is hydrogen, wherein phenyl and Het all are unsubstituted or substituted by one or more identical or different substituents R30, or R16 and R17, together with the nitrogen atom carrying them, form in these embodiments a monocyclic, 4-membered to 7-membered, saturated heterocycle which, in addition to the nitrogen atom carrying R16 and R17, comprises 0 or 1 further ring heteroatom selected from the series consisting of nitrogen, oxygen and sulfur, and which is unsubstituted or substituted by one or more identical or different substituents selected from the series consisting of fluorine and $(C_1-C_4)$-alkyl.

In another embodiment of the invention, R16 is selected from the series consisting of hydrogen and $(C_1-C_4)$-alkyl, in another embodiment from the series consisting of hydrogen and $(C_1-C_3)$-alkyl, in another embodiment from the series consisting of hydrogen and methyl, and in another embodiment R16 is hydrogen, and in one embodiment R17 is selected from the series consisting of hydrogen, $(C_1-C_8)$-alkyl, $(C_3-C_7)$-cycloalkyl, —$(C_1-C_4)$-alkyl-$(C_3-C_7)$-cycloalkyl, phenyl, —$(C_1-C_4)$-alkyl-phenyl, Het and —$(C_1-C_4)$-alkyl-Het, in another embodiment from the series consisting of hydrogen, $(C_1-C_8)$-alkyl, $(C_3-C_7)$-cycloalkyl, —$(C_1-C_4)$-alkyl-$(C_3-C_7)$-cycloalkyl, —$(C_1-C_4)$-alkyl-phenyl and —$(C_1-C_4)$-alkyl-Het, in another embodiment from the series consisting of hydrogen, $(C_1-C_8)$-alkyl, $(C_3-C_7)$-cycloalkyl, —$(C_1-C_4)$-alkyl-$(C_3-C_7)$-cycloalkyl, phenyl, —$(C_1-C_4)$-alkyl-phenyl and —$(C_1-C_4)$-alkyl-Het, in another embodiment from the series consisting of hydrogen, $(C_1-C_8)$-alkyl, $(C_3-C_7)$-cycloalkyl and —$(C_1-C_4)$-alkyl-$(C_3-C_7)$-cycloalkyl, in another embodiment from the series consisting of hydrogen, $(C_1-C_8)$-alkyl and $(C_3-C_7)$-cycloalkyl, in another embodiment from the series consisting of hydrogen and $(C_1-C_8)$-alkyl, in another embodiment from the series consisting of $(C_1-C_8)$-alkyl, and in another embodiment R17 is hydrogen, wherein phenyl and Het all are unsubstituted or substituted by one or more identical or different substituents R30.

In one embodiment of the invention, a $(C_1-C_8)$-alkyl group representing R17 is $(C_1-C_4)$-alkyl, in another embodiment $(C_1-C_3)$-alkyl, in another embodiment $(C_1-C_2)$-alkyl, in another embodiment methyl.

In one embodiment of the invention, R18 is selected from the series consisting of hydrogen and $(C_1-C_2)$-alkyl, in another embodiment from the series consisting of hydrogen and methyl, in another embodiment R18 is hydrogen, in another embodiment R18 is selected from the series consisting $(C_1-C_4)$-alkyl, in another embodiment from the series consisting of $(C_1-C_2)$-alkyl, and in another embodiment R18 is methyl.

The explanations given above with respect to a monocyclic ring which can be formed by R11 and R12 together with the nitrogen atom carrying them, and the embodiments specified above with respect to this ring, apply correspondingly to the monocyclic ring which can be formed by R19 and R20 together with the nitrogen atom carrying them. For example, the ring which can be formed by the groups R19 and R20 together with the nitrogen atom carrying them, which heterocycle is thus bonded via a ring nitrogen atom, can be 4-membered, 5-membered, 6-membered or 7-membered. In one embodiment, the further ring heteroatom which is optionally present in a heterocycle formed by the groups R19 and R20 together with the nitrogen atom carrying them, is selected from the series consisting of nitrogen and oxygen, in another embodiment it is a nitrogen atom, and in another embodiment it is an oxygen atom, and in another embodiment no further ring heteroatom is present. In one embodiment of the invention, substituents in a ring formed by the groups R19 and R20 together with the nitrogen atom carrying them, which are bonded to a ring nitrogen atom, are, selected from the series consisting of $(C_1-C_4)$-alkyl. Examples of heterocyclic groups, from any one or more of which the heterocyclic groups formed by the groups R19 and R20 together with the nitrogen atom carrying them is selected in one embodiment of the invention, likewise are azetidin-1-yl, pyrrolidin-1-yl, piperidin-1-yl, morpholin-4-yl, thiomorpholin-4-yl, and 4-methylpiperazin-1-yl.

In one embodiment of the invention, R19 is selected from the series consisting of hydrogen and $(C_1-C_4)$-alkyl, in another embodiment from the serious consisting of hydrogen and $(C_1-C_3)$-alkyl, in another embodiment from the series consisting of hydrogen and methyl, and in another embodiment R19 is hydrogen, and in one embodiment R20 is selected from the series consisting of hydrogen, $(C_1-C_8)$-alkyl, $(C_3-C_7)$-cycloalkyl, —$(C_1-C_4)$-alkyl-$(C_3-C_7)$-cycloalkyl, phenyl, —$(C_1-C_4)$-alkyl-phenyl, Het and —$(C_1-C_4)$-alkyl-Het, in another embodiment from the series consisting of hydrogen, $(C_1-C_8)$-alkyl, $(C_3-C_7)$-cycloalkyl, —$(C_1-C_4)$-alkyl-$(C_3-C_7)$-cycloalkyl, —$(C_1-C_4)$-alkyl-phenyl and —$(C_1-C_4)$-alkyl-Het, in another embodiment from the series consisting of hydrogen, $(C_1-C_8)$-alkyl, $(C_3-C_7)$-cycloalkyl, —$(C_1-C_4)$-alkyl-$(C_3-C_7)$-cycloalkyl, phenyl, —$(C_1-C_4)$-alkyl-phenyl and —$(C_1-C_4)$-alkyl-Het, in another embodiment from the series consisting of hydrogen, $(C_1-C_8)$-alkyl, $(C_3-C_7)$-cycloalkyl and —$(C_1-C_4)$-alkyl-$(C_3-C_7)$-cycloalkyl, in another embodiment from the series consisting of hydrogen, $(C_1-C_8)$-alkyl and $(C_3-C_7)$-cycloalkyl, in another embodiment from the series consisting of hydrogen and $(C_1-C_8)$-alkyl, in another embodiment from the series consisting of $(C_1-C_8)$-alkyl, and in another embodiment R20 is hydrogen, wherein phenyl and Het all are unsubstituted or substituted by one or more identical or different substituents R30, or R19 and R20, together with the nitrogen atom carrying them, form in these embodiment a monocyclic, 4-membered to 7-membered, saturated heterocycle which, in addition to the nitrogen atom carrying R19 and R20, comprises 0 or 1 further ring heteroatom selected from the series consisting of nitrogen, oxygen and sulfur, and which is unsubstituted or substituted by one or more identical or different substituents selected from the series consisting of fluorine and $(C_1-C_4)$-alkyl.

In another embodiment of the invention, R19 is selected from the series consisting of hydrogen and $(C_1-C_4)$-alkyl, in another embodiment from the serious consisting of hydrogen and $(C_1-C_3)$-alkyl, in another embodiment from the series consisting of hydrogen and methyl, and in another embodiment R19 is hydrogen, and in one embodiment R20 is selected from the series consisting of hydrogen, $(C_1-C_8)$-alkyl, $(C_3-C_7)$-cycloalkyl, —$(C_1-C_4)$-alkyl-$(C_3-C_7)$-cycloalkyl, phenyl, —$(C_1-C_4)$-alkyl-phenyl, Het and —$(C_1-C_4)$-alkyl-Het, in another embodiment from the series consisting of hydrogen, $(C_1-C_8)$-alkyl, $(C_3-C_7)$-cycloalkyl, —$(C_1-C_4)$-alkyl-$(C_3-C_7)$-cycloalkyl, —$(C_1-C_4)$-alkyl-phenyl and —$(C_1-C_4)$-alkyl-Het, in another embodiment from the series consisting of hydrogen, $(C_1-C_8)$-alkyl, $(C_3-C_7)$-cycloalkyl, —$(C_1-C_4)$-alkyl-$(C_3-C_7)$-cycloalkyl, phenyl, —$(C_1-C_4)$-alkyl-phenyl and —$(C_1-C_4)$-alkyl-Het, in another embodiment from the series consisting of hydrogen, $(C_1-C_8)$-alkyl, $(C_3-C_7)$-cycloalkyl and —$(C_1-C_4)$-alkyl-$(C_3-C_7)$-cycloalkyl, in another embodiment from the series consisting of hydrogen, $(C_1-C_8)$-alkyl and $(C_3-C_7)$-cycloalkyl, in another embodiment from the series consisting of hydrogen and $(C_1-C_8)$-alkyl, in another embodiment from the series consisting of $(C_1-C_8)$-alkyl, and in another embodiment R20 is hydrogen, wherein phenyl and Het all are unsubstituted or substituted by one or more identical or different substituents R30.

In one embodiment of the invention, a $(C_1-C_8)$-alkyl group representing R20 is $(C_1-C_4)$-alkyl, in another embodiment $(C_1-C_3)$-alkyl, in another embodiment $(C_1-C_2)$-alkyl, in another embodiment methyl.

In one embodiment of the invention, R21 is selected from the series consisting of hydrogen and $(C_1-C_4)$-alkyl, in another embodiment from the series consisting of hydrogen and $(C_1-C_3)$-alkyl, in another embodiment from the series consisting of hydrogen and methyl, in another embodiment R21 is hydrogen, and in another embodiment R21 is methyl.

In one embodiment of the invention R22 is selected from the series consisting of $(C_1-C_4)$-alkyl, $(C_3-C_6)$-cycloalkyl and —$(C_1-C_2)$-alkyl-$(C_3-C_6)$-cycloalkyl, in another embodiment from the series consisting of $(C_1-C_4)$-alkyl and $(C_3-C_6)$-cycloalkyl, in another embodiment from the series consisting of $(C_1-C_4)$-alkyl and —$(C_1-C_2)$-alkyl-$(C_3-C_6)$-cycloalkyl, in another embodiment from the series consisting of $(C_1-C_4)$-alkyl, in another embodiment from the series consisting of $(C_1-C_3)$-alkyl, and in another embodiment R22 is methyl.

In one embodiment of the invention, R23 and R24 are independently of one another selected from the series consisting of hydrogen and $(C_1-C_3)$-alkyl, in another embodiment from the series consisting of hydrogen and $(C_1-C_2)$-alkyl, in another embodiment from the series consisting of hydrogen and methyl, and in another embodiment R23 and R24 are hydrogen.

In one embodiment of the invention, R30 is in any of its occurrences, independently of its other occurrences, selected from the series consisting of halogen, $(C_1-C_4)$-alkyl and —CN; in another embodiment from the series consisting of halogen, $(C_1-C_4)$-alkyl and —O—$(C_1-C_4)$-alkyl, in another embodiment from the series consisting of halogen and $(C_1-C_4)$-alkyl, in another embodiment from the series consisting of halogen and —CN, in another embodiment from the series consisting of halogen. In one embodiment, a group R30 which is bonded to ring nitrogen atom in a group Het, is selected from the series consisting of $(C_1-C_4)$-alkyl. In one embodiment, a $(C_1-C_4)$-alkyl group representing R30 or occurring in R30 is in any occurrence of R30, independently of other occurrences, selected from $(C_1-C_3)$-alkyl, in another embodiment from $(C_1-C_2)$-alkyl, and in another embodiment it is methyl.

The monocyclic group Het can be 4-membered, 5-membered, 6-membered or 7-membered. In one embodiment of the invention, Het is in any of its occurrences, independently of its other occurrences, 4-membered, 5-membered or 6-membered, in another embodiment 5-membered or 6-membered, in another embodiment 5-membered, in another embodiment 6-membered, in another embodiment 5-membered, 6-membered or 7-membered. In one embodiment, Het is in any of its occurrences, independently of its other occurrences, a saturated or partially saturated heterocycle, in another embodiment a saturated heterocycle, in another embodiment a saturated or aromatic heterocycle, in another embodiment an aromatic heterocycle. In one embodiment, the ring heteroatoms in a heterocycle Het which is saturated or partially unsaturated, are selected from the series consisting of nitrogen and oxygen, in another embodiment from the series consisting of oxygen and sulfur. In one embodiment, the ring heteroatoms in a heterocycle Het which is aromatic, are selected from the series consisting of nitrogen and sulfur. In one embodiment, Het comprises in any of its occurrences, independently of its other occurrences, 1 ring heteroatom selected from the series consisting of nitrogen, oxygen and sulfur. Examples of groups, from any one or more which Het is in any of its occurrences, independently of any other occurrence, selected in one embodiment of the invention, are oxetanyl including oxetan-2-yl and oxetan-3-yl, tetrahydrofuranyl including tetrahydrofuran-2-yl and tetrahydrofuran-3-yl, tetrahydropyranyl including tetrahydropyran-2-yl, tetrahydropyran-3-yl and tetrahydropyran-4-yl, oxepanyl including oxepan-2-yl, oxepan-3-yl and oxepan-4-yl, azetidinyl including azetidin-2-yl and azetidin-3-yl, pyrrolidinyl including pyrrolidin-2-yl and pyrrolidin-3-yl, piperidinyl including piperidin-2-yl, piperidin-3-yl and piperidin-4-yl, azepanyl including azepan-2-yl, azepan-3-yl and azepan-4-yl, morpholinyl including morpholin-2-yl and morpholin-3-yl, thiomorpholinyl including thiomorpholin-2-yl and thiomorpholin-3-yl, piperazinyl including piperazin-2-yl, furanyl including furan-2-yl and furan-3-yl, thiophenyl (thienyl) including thiophen-2-yl and thiophen-3-yl, pyrrolyl including pyrrol-2-yl and pyrrol-3-yl, isoxazolyl including isoxazol-3-yl, isoxazol-4-yl and isoxazol-5-yl, oxazolyl including oxazol-2-yl, oxazol-4-yl and oxazol-5-yl, thiazolyl including thiazol-2-yl, thiazol-4-yl and thiazol-5-yl, pyrazolyl including pyrazol-3-yl, pyrazol-4-yl and pyrazol-5-yl, imidazolyl including imidazol-2-yl, imidazol-4-yl and imidazol-5-yl, pyridinyl (pyridyl) including pyridin-2-yl, pyridin-3-yl and pyridin-4-yl, pyrazinyl including pyrazin-2-yl.

A subject of the invention are all compounds of the formula I wherein any one or more structural elements such as groups, residues, substituents and numbers are defined as in any of the specified embodiments or definitions of the elements, or have one or more of the specific meanings which are mentioned herein as examples of elements, wherein all combinations of one or more definitions of compounds or elements and/or specified embodiments and/or specific meanings of elements are a subject of the present invention. Also with respect to all such compounds of the formula I, all their stereoisomeric forms and mixtures of stereoisomeric forms in any ratio, and their pharmaceutically acceptable salts are a subject of the present invention.

As an example of compounds of the invention which with respect to any structural elements are defined as in specified embodiments of the invention or definitions of such elements, compounds of the formula I may be mentioned, wherein Ar is selected from the series consisting of phenyl and a 5-membered or 6-membered monocyclic aromatic heterocycle comprising 1 or 2 identical or different ring heteroatoms selected from the series consisting of nitrogen, oxygen and sulfur and bonded via a ring carbon atom, which are all unsubstituted or substituted by one or more identical or different substituents R10;

n is selected from the series consisting of 0, 1 and 2;

R1 is selected from the series consisting of hydrogen, —N(R11)-R12, —N(R13)-C(O)—R14, —N(R13)-S(O)$_2$—R15, —N(R13)-C(O)—NH—R14, ($C_1$-$C_4$)-alkyl and —($C_1$-$C_4$)-alkyl-O—R18;

R2 is selected from the series consisting of halogen, —($C_1$-$C_4$)-alkyl and —CN;

R10 is selected from the series consisting of halogen, ($C_1$-$C_4$)-alkyl, —O—($C_1$-$C_4$)-alkyl, —N(R19)-R20, —N(R21)-N(R19)-R20, —N(R21)-C(O)—R22, —NO$_2$, —C(O)—N(R23)-R24 and —CN, and two groups R10 bonded to adjacent ring carbon atoms in Ar, together with the carbon atoms carrying them, can form a 5-membered to 7-membered unsaturated ring which comprises 0, 1 or 2 identical or different ring heteroatoms selected from the series consisting of nitrogen, oxygen and sulfur, and which is unsubstituted or substituted by one or more identical or different substituents selected from the series consisting of halogen, —($C_1$-$C_4$)-alkyl and —CN;

R11 and R12 are independently of one another selected from the series consisting of hydrogen and ($C_1$-$C_4$)-alkyl, or R11 and R12, together with the nitrogen atom carrying them, form a monocyclic, 4-membered to 6-membered, saturated heterocycle which, in addition to the nitrogen atom carrying R11 and R12, comprises 0 or 1 further ring heteroatom selected from the series consisting of nitrogen, oxygen and sulfur, and which is unsubstituted or substituted by one or more identical or different substituents selected from the series consisting of fluorine and ($C_1$-$C_4$)-alkyl;

R13 is selected from the series consisting of hydrogen and ($C_1$-$C_4$)-alkyl;

R14 and R15 are independently of one another selected from the series consisting of ($C_3$-$C_7$)-cycloalkyl, phenyl, —($C_1$-$C_4$)-alkyl-phenyl, Het and —($C_1$-$C_4$)-alkyl-Het, wherein phenyl and Het all are unsubstituted or substituted by one or more identical or different substituents R30;

R18 is selected from the series consisting of hydrogen and ($C_1$-$C_4$)-alkyl;

R19 is selected from the series consisting of hydrogen and ($C_1$-$C_4$)-alkyl;

R20 is selected from the series consisting of hydrogen, ($C_1$-$C_8$)-alkyl, ($C_3$-$C_7$)-cycloalkyl and —($C_1$-$C_4$)-alkyl-($C_3$-$C_7$)-cycloalkyl;

or R19 and R20, together with the nitrogen atom carrying them, form a monocyclic, 4-membered to 6-membered, saturated heterocycle which, in addition to the nitrogen atom carrying R19 and R20, comprises 0 or 1 further ring heteroatom selected from the series consisting of nitrogen, oxygen and sulfur, and which is unsubstituted or substituted by one or more identical or different substituents selected from the series consisting of fluorine and ($C_1$-$C_4$)-alkyl;

R21 is selected from the series consisting of hydrogen and ($C_1$-$C_4$)-alkyl;

R22 is selected from the series consisting of ($C_1$-$C_4$)-alkyl and ($C_3$-$C_7$)-cycloalkyl;

R23 and R24 are independently of one another selected from the series consisting of hydrogen and ($C_1$-$C_4$)-alkyl;

R30 is selected from the series consisting of halogen, ($C_1$-$C_4$)-alkyl and —CN;

Het is a monocyclic, 4-membered to 7-membered, saturated, partially unsaturated or aromatic heterocycle which comprises 1 or 2 identical or different ring heteroatoms selected from the series consisting of nitrogen, oxygen and sulfur, and which is bonded via a ring carbon atom;

wherein all cycloalkyl groups can be substituted by one or more identical substituents selected from the series consisting of fluorine and ($C_1$-$C_4$)-alkyl;

wherein all alkyl groups, independently of any other substituents which can be present on an alkyl group, can be substituted by one or more fluorine substituents;

in any of their stereoisomeric forms or a mixture of stereoisomeric forms in any ratio, and the pharmaceutically acceptable salt thereof.

As another such example, compounds of the formula I may be mentioned, wherein

Ar is selected from the series consisting of phenyl and a 5-membered or 6-membered monocyclic aromatic heterocycle comprising 1 or 2 identical or different ring heteroatoms selected from the series consisting of nitrogen, oxygen and sulfur and bonded via a ring carbon atom, which are all unsubstituted or substituted by one or more identical or different substituents R10;

n is selected from the series consisting of 0 and 1;

R1 is selected from the series consisting of hydrogen, —N(R11)-R12, —N(R13)-C(O)—R14, —N(R13)-S(O)$_2$—R15, —N(R13)-C(O)—NH—R14 and ($C_1$-$C_4$)-alkyl;

R2 is selected from the series consisting of halogen and —($C_1$-$C_4$)-alkyl;

R10 is selected from the series consisting of halogen, ($C_1$-$C_4$)-alkyl, —O—($C_1$-$C_4$)-alkyl, —N(R19)-R20, —N(R21)-N(R19)-R20, —N(R21)-C(O)—R22, —NO$_2$ and —CN, and two groups R10 bonded to adjacent ring carbon atoms in Ar, together with the carbon atoms carrying them, can form a 5-membered to 7-membered unsaturated ring which comprises 0, 1 or 2 identical or different ring heteroatoms selected from the series consisting of nitrogen, oxygen and sulfur, and which is unsubstituted or substituted by one or more identical or different substituents selected from the series consisting of halogen and —($C_1$-$C_4$)-alkyl;

R11 and R12 are independently of one another selected from the series consisting of hydrogen and ($C_1$-$C_4$)-alkyl, or R11 and R12, together with the nitrogen atom carrying them, form a monocyclic, 5-membered or 6-membered, saturated heterocycle which, in addition to the nitrogen atom carrying R11 and R12, comprises 0 or 1 further ring heteroatom selected from the series consisting of nitrogen, oxygen and sulfur, and which is unsubstituted or substituted by one or more identical or different substituents selected from the series consisting of fluorine and ($C_1$-$C_4$)-alkyl;

R13 is selected from the series consisting of hydrogen and ($C_1$-$C_4$)-alkyl;

R14 and R15 are independently of one another selected from the series consisting of ($C_3$-$C_7$)-cycloalkyl, phenyl, —($C_1$-$C_4$)-alkyl-phenyl, Het and —($C_1$-$C_4$)-alkyl-Het, wherein phenyl and Het all are unsubstituted or substituted by one or more identical or different substituents R30;

R19 is selected from the series consisting of hydrogen and ($C_1$-$C_4$)-alkyl;

R20 is selected from the series consisting of hydrogen and ($C_1$-$C_4$)-alkyl;

or R19 and R20, together with the nitrogen atom carrying them, form a monocyclic, 4-membered to 6-membered, saturated heterocycle which, in addition to the nitrogen atom carrying R19 and R20, comprises 0 or 1 further ring heteroatom selected from the series consisting of nitrogen, oxygen and sulfur, and which is unsubstituted or substituted by one or more identical or different substituents selected from the series consisting of fluorine and ($C_1$-$C_4$)-alkyl;

R21 is selected from the series consisting of hydrogen and ($C_1$-$C_4$)-alkyl;

R22 is selected from the series consisting of ($C_1$-$C_4$)-alkyl;

R30 is selected from the series consisting of halogen, (C$_1$-C$_4$)-alkyl and —CN;

Het is a monocyclic, 5-membered or 6-membered, saturated, partially unsaturated or aromatic heterocycle which comprises 1 or 2 identical or different ring heteroatoms selected from the series consisting of nitrogen, oxygen and sulfur, and which is bonded via a ring carbon atom;

wherein all cycloalkyl groups can be substituted by one or more identical substituents selected from the series consisting of fluorine and (C$_1$-C$_4$)-alkyl;

wherein all alkyl groups, independently of any other substituents which can be present on an alkyl group, can be substituted by one or more fluorine substituents;

in any of their stereoisomeric forms or a mixture of stereoisomeric forms in any ratio, and the pharmaceutically acceptable salt thereof.

As another such example, compounds of the formula I may be mentioned, wherein

Ar is phenyl which is unsubstituted or substituted by one or more identical or different substituents R10;

n is selected from the series consisting of 0 and 1;

R1 is selected from the series consisting of hydrogen, —N(R11)-R12, —N(R13)-C(O)—R14, —N(R13)-S(O)$_2$—R15, —N(R13)-C(O)—NH—R14 and (C$_1$-C$_4$)-alkyl;

R2 is selected from the series consisting of halogen and —(C$_1$-C$_4$)-alkyl;

R10 is selected from the series consisting of halogen, (C$_1$-C$_4$)-alkyl, —O—(C$_1$-C$_4$)-alkyl, —N(R19)-R20, —N(R21)-N(R19)-R20, —N(R21)-C(O)—R22, —NO$_2$ and —CN, and two groups R10 bonded to adjacent ring carbon atoms in Ar, together with the carbon atoms carrying them, can form a 5-membered to 7-membered unsaturated ring which comprises 0, 1 or 2 oxygen atoms as ring heteroatoms, and which is unsubstituted or substituted by one or more identical or different substituents selected from the series consisting of halogen and —(C$_1$-C$_4$)-alkyl;

R11 and R12 are independently of one another selected from the series consisting of hydrogen and (C$_1$-C$_4$)-alkyl;

R13 is selected from the series consisting of hydrogen and (C$_1$-C$_4$)-alkyl;

R14 and R15 are independently of one another selected from the series consisting of (C$_3$-C$_7$)-cycloalkyl, phenyl, —(C$_1$-C$_4$)-alkyl-phenyl, Het and —(C$_1$-C$_4$)-alkyl-Het, wherein phenyl and Het all are unsubstituted or substituted by one or more identical or different substituents R30;

R19 is selected from the series consisting of hydrogen and (C$_1$-C$_4$)-alkyl;

R20 is selected from the series consisting of hydrogen and (C$_1$-C$_4$)-alkyl;

R21 is selected from the series consisting of hydrogen and (C$_1$-C$_4$)-alkyl;

R22 is selected from the series consisting of (C$_1$-C$_4$)-alkyl;

R30 is selected from the series consisting of halogen and (C$_1$-C$_4$)-alkyl;

Het is a monocyclic, 5-membered or 6-membered, saturated, partially unsaturated or aromatic heterocycle which comprises 1 ring heteroatom selected from the series consisting of nitrogen, oxygen and sulfur, and which is bonded via a ring carbon atom;

wherein all cycloalkyl groups can be substituted by one or more identical substituents selected from the series consisting of fluorine and (C$_1$-C$_4$)-alkyl;

wherein all alkyl groups, independently of any other substituents which can be present on an alkyl group, can be substituted by one or more fluorine substituents;

in any of their stereoisomeric forms or a mixture of stereoisomeric forms in any ratio, and the pharmaceutically acceptable salt thereof.

As another such example, compounds of the formula I may be mentioned, wherein

Ar is selected from the series consisting of 2,3-dichloro-phenyl, 2,5-dichloro-phenyl, 5-chloro-2-hydrazino-phenyl, 5-chloro-2-cyano-phenyl, 2-cyano-5-methyl-phenyl, 2-fluoro-5-methyl-phenyl, 2-chloro-5-methoxy-phenyl, 2,5-dichloro-thiophen-3-yl, 8-chloro-3,4-dihydro-2H-benzo[b][1,4]dioxepin-7-yl, 5-chloro-1,3-dimethyl-pyrazol-4-yl, naphthalen-1-yl, 2,4,6-trichloro-phenyl, 5-chloro-2-fluoro-phenyl, 2,4,5-trifluoro-phenyl, 2,4,5-trichloro-phenyl, 5-chloro-2,4-difluoro-phenyl, 2,3,4-trichloro-phenyl, 2,3,4-trifluoro-phenyl, 2-chloro-4-trifluoromethyl-phenyl, 5-cyano-2-fluoro-phenyl, 2-cyano-5-methoxy-phenyl, 2-cyano-5-fluoro-phenyl, 2-fluoro-5-methoxy-phenyl, 4-acetylamino-2-methyl-phenyl, 2-methyl-5-nitro-phenyl, and 2-nitro-4-trifluoromethyl-phenyl;

n is selected from the series consisting of 0 and 1;

R1 is selected from the series consisting of hydrogen, —N(R11)-R12, —N(R13)-C(O)—R14, —N(R13)-S(O)$_2$—R15, —N(R13)-C(O)—NH—R14 and (C$_1$-C$_4$)-alkyl;

R2 is selected from the series consisting of halogen and —(C$_1$-C$_4$)-alkyl;

R11 and R12 are independently of one another selected from the series consisting of hydrogen and (C$_1$-C$_4$)-alkyl;

R13 is selected from the series consisting of hydrogen and (C$_1$-C$_4$)-alkyl;

R14 and R15 are independently of one another selected from the series consisting of (C$_3$-C$_7$)-cycloalkyl, phenyl, —(C$_1$-C$_4$)-alkyl-phenyl, Het and —(C$_1$-C$_4$)-alkyl-Het, wherein phenyl and Het all are unsubstituted or substituted by one or more identical or different substituents R30;

R30 is selected from the series consisting of halogen and (C$_1$-C$_4$)-alkyl;

Het is a monocyclic, 5-membered or 6-membered, saturated, partially unsaturated or aromatic heterocycle which comprises 1 ring heteroatom selected from the series consisting of nitrogen, oxygen and sulfur, and which is bonded via a ring carbon atom;

wherein all cycloalkyl groups can be substituted by one or more identical substituents selected from the series consisting of fluorine and (C$_1$-C$_4$)-alkyl;

wherein all alkyl groups, independently of any other substituents which can be present on an alkyl group, can be substituted by one or more fluorine substituents;

in any of their stereoisomeric forms or a mixture of stereoisomeric forms in any ratio, and the pharmaceutically acceptable salt thereof.

As another such example, compounds of the formula I may be mentioned, wherein

Ar is selected from the series consisting of 2,3-dichloro-phenyl, 2,5-dichloro-phenyl, 5-chloro-2-hydrazino-phenyl, 5-chloro-2-cyano-phenyl, 2-cyano-5-methyl-phenyl, 2-fluoro-5-methyl-phenyl, 2-chloro-5-methoxy-phenyl, 2,5-dichloro-thiophen-3-yl, 8-chloro-3,4-dihydro-2H-benzo[b][1,4]dioxepin-7-yl, 5-chloro-1,3-dimethyl-pyrazol-4-yl, naphthalen-1-yl, 5-cyano-2-fluoro-phenyl, 2-cyano-5-methoxy-phenyl, 2-cyano-5-fluoro-phenyl, 2-fluoro-5-methoxy-phenyl, 4-acetylamino-2-methyl-phenyl, 2-methyl-5-nitro-phenyl, and 2-nitro-4-trifluoromethyl-phenyl;

n is selected from the series consisting of 0 and 1;

R1 is selected from the series consisting of hydrogen, —N(R11)-R12, —N(R13)-C(O)—R14, —N(R13)-S(O)$_2$—R15, —N(R13)-C(O)—NH—R14 and (C$_1$-C$_4$)-alkyl;

R2 is selected from the series consisting of halogen and —(C$_1$-C$_4$)-alkyl;

R11 and R12 are independently of one another selected from the series consisting of hydrogen and (C$_1$-C$_4$)-alkyl;

R13 is selected from the series consisting of hydrogen and (C$_1$-C$_4$)-alkyl;

R14 and R15 are independently of one another selected from the series consisting of (C$_3$-C$_7$)-cycloalkyl, phenyl, —(C$_1$-C$_4$)-alkyl-phenyl, Het and —(C$_1$-C$_4$)-alkyl-Het, wherein phenyl and Het all are unsubstituted or substituted by one or more identical or different substituents R30;

R30 is selected from the series consisting of halogen and (C$_1$-C$_4$)-alkyl;

Het is a monocyclic, 5-membered or 6-membered, saturated, partially unsaturated or aromatic heterocycle which comprises 1 ring heteroatom selected from the series consisting of nitrogen, oxygen and sulfur, and which is bonded via a ring carbon atom;

wherein all cycloalkyl groups can be substituted by one or more identical substituents selected from the series consisting of fluorine and (C$_1$-C$_4$)-alkyl;

wherein all alkyl groups, independently of any other substituents which can be present on an alkyl group, can be substituted by one or more fluorine substituents;

in any of their stereoisomeric forms or a mixture of stereoisomeric forms in any ratio, and the pharmaceutically acceptable salt thereof.

A subject of the invention also is a compound of the formula I which is selected from any of the specific compounds of the formula I which are disclosed herein, or is any one of the specific compounds of the formula I which are disclosed herein, irrespective thereof whether they are disclosed as a free compound and/or as a specific salt, or a pharmaceutically acceptable salt thereof, wherein the compound of the formula I is a subject of the invention in any of its stereoisomeric forms or a mixture of stereoisomeric forms in any ratio. For example, a subject of the invention is a compound of the formula I which is selected from the series consisting of:

N-[4-(3-amino-1H-pyrazolo[3,4-b]pyrazin-6-yl)phenyl]-2,3-dichloro-benzenesulfonamide,
2,5-dichloro-N-[4-(1H-pyrazolo[3,4-b]pyrazin-6-yl)phenyl]benzenesulfonamide,
2,5-dichloro-N-[2-fluoro-4-(1H-pyrazolo[3,4-b]pyrazin-6-yl)phenyl]benzenesulfonamide,
2,3-dichloro-N-[2-fluoro-4-(1H-pyrazolo[3,4-b]pyrazin-6-yl)-phenyl]-benzenesulfonamide,
N-[4-(3-amino-1H-pyrazolo[3,4-b]pyrazin-6-yl)phenyl]-2,5-dichloro-benzenesulfonamide,
N-[4-(3-amino-1H-pyrazolo[3,4-b]pyrazin-6-yl)phenyl]-5-chloro-2-hydrazino-benzenesulfonamide,
N-[4-(3-amino-1H-pyrazolo[3,4-b]pyrazin-6-yl)-2-fluoro-phenyl]-5-chloro-2-fluoro-benzenesulfonamide,
N-[4-(3-amino-1H-pyrazolo[3,4-b]pyrazin-6-yl)-2-fluoro-phenyl]-2,5-dichloro-benzenesulfonamide,
N-[4-(3-amino-1H-pyrazolo[3,4-b]pyrazin-6-yl)-2-fluoro-phenyl]-2,3-dichloro-benzenesulfonamide,
2,5-dichloro-N-[4-(3-methyl-1H-pyrazolo[3,4-b]pyrazin-6-yl)phenyl]benzenesulfonamide,
2,3-dichloro-N-[4-(3-methyl-1H-pyrazolo[3,4-b]pyrazin-6-yl)phenyl]benzenesulfonamide,
5-chloro-2-fluoro-N-[4-(3-methyl-1H-pyrazolo[3,4-b]pyrazin-6-yl)phenyl]benzenesulfonamide,
5-chloro-2-cyano-N-[4-(3-methyl-1H-pyrazolo[3,4-b]pyrazin-6-yl)phenyl]benzenesulfonamide,
2-cyano-5-methyl-N-[4-(3-methyl-1H-pyrazolo[3,4-b]pyrazin-6-yl)phenyl]benzenesulfonamide,
2-fluoro-5-methyl-N-[4-(3-methyl-1H-pyrazolo[3,4-b]pyrazin-6-yl)phenyl]benzenesulfonamide,
2-chloro-5-methoxy-N-[4-(3-methyl-1H-pyrazolo[3,4-b]pyrazin-6-yl)phenyl]benzenesulfonamide,
N-[4-(3-amino-1H-pyrazolo[3,4-b]pyrazin-6-yl)phenyl]-2-cyano-5-methyl-benzenesulfonamide,
N-[4-(3-amino-1H-pyrazolo[3,4-b]pyrazin-6-yl)phenyl]-2-chloro-5-methoxy-benzenesulfonamide,
N-[4-(3-amino-1H-pyrazolo[3,4-b]pyrazin-6-yl)phenyl]-2-fluoro-5-methyl-benzenesulfonamide,
N-[4-(3-amino-1H-pyrazolo[3,4-b]pyrazin-6-yl)-phenyl]-5-chloro-2-cyano-benzenesulfonamide,
N-[4-(3-amino-1H-pyrazolo[3,4-b]pyrazin-6-yl)phenyl]-2,5-dichloro-thiophene-3-sulfonamide,
N-[4-(3-amino-1H-pyrazolo[3,4-b]pyrazin-6-yl)phenyl]-8-chloro-3,4-dihydro-2H-benzo[b][1,4]dioxepine-7-sulfonamide,
N-[4-(3-amino-1H-pyrazolo[3,4-b]pyrazin-6-yl)phenyl]-5-chloro-1,3-dimethyl-pyrazole-4-sulfonamide,
N-[6-[4-[(2-fluoro-5-methyl-phenyl)sulfonylamino]phenyl]-1H-pyrazolo[3,4-b]pyrazin-3-yl]cyclopropanecarboxamide,
N-[6-[4-[(2-fluoro-5-methyl-phenyl)sulfonylamino]phenyl]-1H-pyrazolo[3,4-b]pyrazin-3-yl]tetrahydropyran-4-carboxamide,
N-[6-[4-[(2-fluoro-5-methyl-phenyl)sulfonylamino]phenyl]-1H-pyrazolo[3,4-b]pyrazin-3-yl]piperidine-4-carboxamide,
N-[6-[4-[(2-fluoro-5-methyl-phenyl)sulfonylamino]phenyl]-1H-pyrazolo[3,4-b]pyrazin-3-yl]cyclopentanecarboxamide,
2,3-dichloro-N-[6-[4-[(2-fluoro-5-methyl-phenyl)sulfonylamino]phenyl]-1H-pyrazolo[3,4-b]pyrazin-3-yl]benzamide,
N-[6-[4-[(2-fluoro-5-methyl-phenyl)sulfonylamino]phenyl]-1H-pyrazolo[3,4-b]pyrazin-3-yl]cyclohexanecarboxamide,
N-[6-[4-[(2-fluoro-5-methyl-phenyl)sulfonylamino]phenyl]-1H-pyrazolo[3,4-b]pyrazin-3-yl]-2-phenyl-acetamide,
N-[6-[4-[(2-fluoro-5-methyl-phenyl)sulfonylamino]phenyl]-1H-pyrazolo[3,4-b]pyrazin-3-yl]thiophene-3-carboxamide,
4-chloro-N-[6-[4-[(2-fluoro-5-methyl-phenyl)sulfonylamino]phenyl]-1H-pyrazolo[3,4-b]pyrazin-3-yl]benzamide,
N-[4-(3-amino-1H-pyrazolo[3,4-b]pyrazin-6-yl)phenyl]naphthalene-1-sulfonamide,
N-[4-(3-amino-1H-pyrazolo[3,4-b]pyrazin-6-yl)phenyl]-2,4,6-trichloro-benzenesulfonamide,
N-[4-(3-amino-1H-pyrazolo[3,4-b]pyrazin-6-yl)phenyl]-5-chloro-2-fluoro-benzenesulfonamide,
N-[4-(3-amino-1H-pyrazolo[3,4-b]pyrazin-6-yl)phenyl]-2,4,5-trifluoro-benzenesulfonamide,
N-[4-(3-amino-1H-pyrazolo[3,4-b]pyrazin-6-yl)phenyl]-2,4,5-trichloro-benzenesulfonamide,
N-[4-(3-amino-1H-pyrazolo[3,4-b]pyrazin-6-yl)phenyl]-5-chloro-2,4-difluoro-benzenesulfonamide,
N-[4-(3-amino-1H-pyrazolo[3,4-b]pyrazin-6-yl)phenyl]-2,3,4-trichloro-benzenesulfonamide,
N-[4-(3-amino-1H-pyrazolo[3,4-b]pyrazin-6-yl)phenyl]-2,3,4-trifluoro-benzenesulfonamide),
N-[4-(3-amino-1H-pyrazolo[3,4-b]pyrazin-6-yl)phenyl]-2-chloro-4-trifluoromethyl-benzenesulfonamide,
5-chloro-N-[4-[3-[(5-chloro-2,4-difluoro-phenyl)sulfonylamino]-1H-pyrazolo[3,4-b]pyrazin-6-yl]phenyl]-2,4-difluoro-benzenesulfonamide, 5-chloro-N-[4-[3-[(5-chloro-1,3-dimethyl-pyrazol-4-yl)sulfonylamino]-1H-pyrazolo[3,4-b]pyrazin-6-yl]phenyl]-1,3-dimethyl-pyrazole-4-sulfonamide,
2,4,5-trifluoro-N-[4-[3-[(2,4,5-trifluorophenyl)sulfonylamino]-1H-pyrazolo[3,4-b]pyrazin-6-yl]phenyl]benzenesulfonamide,
N-[4-(3-amino-1H-pyrazolo[3,4-b]pyrazin-6-yl)-phenyl]-5-cyano-2-fluoro-benzenesulfonamide,
N-[4-(3-amino-1H-pyrazolo[3,4-b]pyrazin-6-yl)-phenyl]-2-cyano-5-methoxy-benzenesulfonamide,
N-[4-(3-amino-1H-pyrazolo[3,4-b]pyrazin-6-yl)-phenyl]-2-cyano-5-fluoro-benzenesulfonamide,
N-[4-(3-amino-1H-pyrazolo[3,4-b]pyrazin-6-yl)-phenyl]-2-fluoro-5-methoxy-benzenesulfonamide,
1-[6-[4-[(2-fluoro-5-methyl-phenyl)sulfonylamino]phenyl]-1H-pyrazolo[3,4-b]pyrazin-3-yl]-3-(3-pyridyl)urea,
1-(4-chlorophenyl)-3-[6-[4-[(2-fluoro-5-methyl-phenyl)sulfonylamino]phenyl]-1H-pyrazolo[3,4-b]pyrazin-3-yl]urea,
2-chloro-N-[4-[3-[[2-chloro-4-trifluoromethyl-phenyl]sulfonylamino]-1H-pyrazolo[3,4-b]pyrazin-6-yl]phenyl]-4-trifluoromethyl-benzenesulfonamide,
N-[6-[4-(1-naphthylsulfonylamino)phenyl]-1H-pyrazolo[3,4-b]pyrazin-3-yl]naphthalene-1-sulfonamide,
2,4,6-trichloro-N-[4-[3-[(2,4,6-trichlorophenyl)sulfonylamino]-1H-pyrazolo[3,4-b]pyrazin-6-yl]phenyl]benzenesulfonamide,
N[3-methyl-4-[[4-(3-methyl-1H-pyrazolo[3,4-b]pyrazin-6-yl)phenyl]sulfamoyl]phenyl]acetamide,
2-methyl-N-[4-(3-methyl-1H-pyrazolo[3,4-b]pyrazin-6-yl)phenyl]-5-nitro-benzenesulfonamide, and
N-[4-(3-methyl-1H-pyrazolo[3,4-b]pyrazin-6-yl)phenyl]-2-nitro-4-trifluoromethyl-benzenesulfonamide,
or which is any one of these compounds, and its pharmaceutically acceptable salts.

Another subject of the invention is a compound of the formula I which is selected from the series consisting of:
N-[4-(3-amino-1H-pyrazolo[3,4-b]pyrazin-6-yl)phenyl]-2,3-dichloro-benzenesulfonamide,
2,5-dichloro-N-[4-(1H-pyrazolo[3,4-b]pyrazin-6-yl)phenyl]benzenesulfonamide,
2,5-dichloro-N-[2-fluoro-4-(1H-pyrazolo[3,4-b]pyrazin-6-yl)phenyl]benzenesulfonamide,
2,3-dichloro-N-[2-fluoro-4-(1H-pyrazolo[3,4-b]pyrazin-6-yl)-phenyl]-benzenesulfonamide,
N-[4-(3-amino-1H-pyrazolo[3,4-b]pyrazin-6-yl)phenyl]-2,5-dichloro-benzenesulfonamide,
N-[4-(3-amino-1H-pyrazolo[3,4-b]pyrazin-6-yl)phenyl]-5-chloro-2-hydrazino-benzenesulfonamide,
N-[4-(3-amino-1H-pyrazolo[3,4-b]pyrazin-6-yl)-2-fluoro-phenyl]-5-chloro-2-fluoro-benzenesulfonamide,
N-[4-(3-amino-1H-pyrazolo[3,4-b]pyrazin-6-yl)-2-fluoro-phenyl]-2,5-dichloro-benzenesulfonamide,
N-[4-(3-amino-1H-pyrazolo[3,4-b]pyrazin-6-yl)-2-fluoro-phenyl]-2,3-dichloro-benzenesulfonamide,
2,5-dichloro-N-[4-(3-methyl-1H-pyrazolo[3,4-b]pyrazin-6-yl)phenyl]benzenesulfonamide,
2,3-dichloro-N-[4-(3-methyl-1H-pyrazolo[3,4-b]pyrazin-6-yl)phenyl]benzenesulfonamide,
5-chloro-2-fluoro-N-[4-(3-methyl-1H-pyrazolo[3,4-b]pyrazin-6-yl)phenyl]benzenesulfonamide,
5-chloro-2-cyano-N-[4-(3-methyl-1H-pyrazolo[3,4-b]pyrazin-6-yl)phenyl]benzenesulfonamide,
2-cyano-5-methyl-N-[4-(3-methyl-1H-pyrazolo[3,4-b]pyrazin-6-yl)phenyl]benzenesulfonamide,
2-fluoro-5-methyl-N-[4-(3-methyl-1H-pyrazolo[3,4-b]pyrazin-6-yl)phenyl]benzenesulfonamide,
2-chloro-5-methoxy-N-[4-(3-methyl-1H-pyrazolo[3,4-b]pyrazin-6-yl)phenyl]benzenesulfonamide,
N-[4-(3-amino-1H-pyrazolo[3,4-b]pyrazin-6-yl)phenyl]-2-cyano-5-methyl-benzenesulfonamide,
N-[4-(3-amino-1H-pyrazolo[3,4-b]pyrazin-6-yl)phenyl]-2-chloro-5-methoxy-benzenesulfonamide,
N-[4-(3-amino-1H-pyrazolo[3,4-b]pyrazin-6-yl)phenyl]-2-fluoro-5-methyl-benzenesulfonamide,
N-[4-(3-amino-1H-pyrazolo[3,4-b]pyrazin-6-yl)-phenyl]-5-chloro-2-cyano-benzenesulfonamide,
N-[4-(3-amino-1H-pyrazolo[3,4-b]pyrazin-6-yl)phenyl]-2,5-dichloro-thiophene-3-sulfonamide,
N-[4-(3-amino-1H-pyrazolo[3,4-b]pyrazin-6-yl)phenyl]-8-chloro-3,4-dihydro-2H-benzo[b][1,4]dioxepine-7-sulfonamide,
N-[4-(3-amino-1H-pyrazolo[3,4-b]pyrazin-6-yl)phenyl]-5-chloro-1,3-dimethyl-pyrazole-4-sulfonamide,
N-[6-[4-[(2-fluoro-5-methyl-phenyl)sulfonylamino]phenyl]-1H-pyrazolo[3,4-b]pyrazin-3-yl]cyclopropanecarboxamide,
N-[6-[4-[(2-fluoro-5-methyl-phenyl)sulfonylamino]phenyl]-1H-pyrazolo[3,4-b]pyrazin-3-yl]tetrahydropyran-4-carboxamide,
N-[6-[4-[(2-fluoro-5-methyl-phenyl)sulfonylamino]phenyl]-1H-pyrazolo[3,4-b]pyrazin-3-yl]piperidine-4-carboxamide,
N-[6-[4-[(2-fluoro-5-methyl-phenyl)sulfonylamino]phenyl]-1H-pyrazolo[3,4-b]pyrazin-3-yl]cyclopentanecarboxamide,
2,3-dichloro-N-[6-[4-[(2-fluoro-5-methyl-phenyl)sulfonylamino]phenyl]-1H-pyrazolo[3,4-b]pyrazin-3-yl]benzamide,
N-[6-[4-[(2-fluoro-5-methyl-phenyl)sulfonylamino]phenyl]-1H-pyrazolo[3,4-b]pyrazin-3-yl]cyclohexanecarboxamide,
N-[6-[4-[(2-fluoro-5-methyl-phenyl)sulfonylamino]phenyl]-1H-pyrazolo[3,4-b]pyrazin-3-yl]-2-phenyl-acetamide,
N-[6-[4-[(2-fluoro-5-methyl-phenyl)sulfonylamino]phenyl]-1H-pyrazolo[3,4-b]pyrazin-3-yl]thiophene-3-carboxamide,
4-chloro-N-[6-[4-[(2-fluoro-5-methyl-phenyl)sulfonylamino]phenyl]-1H-pyrazolo[3,4-b]pyrazin-3-yl]benzamide,
N-[4-(3-amino-1H-pyrazolo[3,4-b]pyrazin-6-yl)phenyl]naphthalene-1-sulfonamide,
5-chloro-N-[4-[3-[(5-chloro-2,4-difluoro-phenyl)sulfonylamino]-1H-pyrazolo[3,4-b]pyrazin-6-yl]phenyl]-2,4-difluoro-benzenesulfonamide,
5-chloro-N-[4-[3-[(5-chloro-1,3-dimethyl-pyrazol-4-yl)sulfonylamino]-1H-pyrazolo[3,4-b]pyrazin-6-yl]phenyl]-1,3-dimethyl-pyrazole-4-sulfonamide,
2,4,5-trifluoro-N-[4-[3-[(2,4,5-trifluorophenyl)sulfonylamino]-1H-pyrazolo[3,4-b]pyrazin-6-yl]phenyl]benzenesulfonamide,
N-[4-(3-amino-1H-pyrazolo[3,4-b]pyrazin-6-yl)-phenyl]-5-cyano-2-fluoro-benzenesulfonamide,
N-[4-(3-amino-1H-pyrazolo[3,4-b]pyrazin-6-yl)-phenyl]-2-cyano-5-methoxy-benzenesulfonamide,
N-[4-(3-amino-1H-pyrazolo[3,4-b]pyrazin-6-yl)-phenyl]-2-cyano-5-fluoro-benzenesulfonamide,
N-[4-(3-amino-1H-pyrazolo[3,4-b]pyrazin-6-yl)-phenyl]-2-fluoro-5-methoxy-benzenesulfonamide,
1-[6-[4-[(2-fluoro-5-methyl-phenyl)sulfonylamino]phenyl]-1H-pyrazolo[3,4-b]pyrazin-3-yl]-3-(3-pyridyl)urea, 1-(4-chlorophenyl)-3-[6-[4-[(2-fluoro-5-methyl-phenyl)sulfonylamino]phenyl]-1H-pyrazolo[3,4-b]pyrazin-3-yl]urea,
2-chloro-N-[4-[3-[[2-chloro-4-trifluoromethyl-phenyl]sulfonylamino]-1H-pyrazolo[3,4-b]pyrazin-6-yl]phenyl]-4-trifluoromethyl-benzenesulfonamide,
N-[6-[4-(1-naphthylsulfonylamino)phenyl]-1H-pyrazolo[3,4-b]pyrazin-3-yl]naphthalene-1-sulfonamide,
2,4,6-trichloro-N-[4-[3-[(2,4,6-trichlorophenyl)sulfonylamino]-1H-pyrazolo[3,4-b]pyrazin-6-yl]phenyl]benzenesulfonamide,
N-[3-methyl-4-[[4-(3-methyl-1H-pyrazolo[3,4-b]pyrazin-6-yl)phenyl]sulfamoyl]phenyl]acetamide,
2-methyl-N-[4-(3-methyl-1H-pyrazolo[3,4-b]pyrazin-6-yl)phenyl]-5-nitro-benzenesulfonamide, and
N-[4-(3-methyl-1H-pyrazolo[3,4-b]pyrazin-6-yl)phenyl]-2-nitro-4-trifluoromethyl-benzenesulfonamide,
or which is any one of these compounds, and its pharmaceutically acceptable salts.

In one embodiment of the invention, the compounds of the formula I are defined as above in their generic definition or in any of the more specific definitions or embodiments, with the proviso that the compound of the formula I is not one of the following compounds:
N-[4-(3-amino-1H-pyrazolo[3,4-b]pyrazin-6-yl)phenyl]-2,4,6-trichloro-benzenesulfonamide,
N-[4-(3-amino-1H-pyrazolo[3,4-b]pyrazin-6-yl)phenyl]-5-chloro-2-fluoro-benzenesulfonamide,
N-[4-(3-amino-1H-pyrazolo[3,4-b]pyrazin-6-yl)phenyl]-2,4,5-trifluoro-benzenesulfonamide,
N-[4-(3-amino-1H-pyrazolo[3,4-b]pyrazin-6-yl)phenyl]-2,4,5-trichloro-benzenesulfonamide,
N-[4-(3-amino-1H-pyrazolo[3,4-b]pyrazin-6-yl)phenyl]-5-chloro-2,4-difluoro-benzenesulfonamide,
N-[4-(3-amino-1H-pyrazolo[3,4-b]pyrazin-6-yl)phenyl]-2,3,4-trichloro-benzenesulfonamide,
N-[4-(3-amino-1H-pyrazolo[3,4-b]pyrazin-6-yl)phenyl]-2,3,4-trifluoro-benzenesulfonamide, and
N-[4-(3-amino-1H-pyrazolo[3,4-b]pyrazin-6-yl)phenyl]-2-chloro-4-trifluoromethyl-benzenesulfonamide,
and in another embodiment the excluded compounds are excluded as the free compounds, i.e. they are not excluded in the form of a salt with an acid or base.

In another embodiment of the invention, the compounds of the formula I are defined as above in their generic definition or in any of the more specific definitions or embodiments, with the proviso that the compound of the formula I is not a compound in which simultaneously the group Ar is a phenyl group which is substituted by three identical or different halogen substituents, n is 0, and R1 is the group —NH$_2$ (amino), and the proviso that the compound of the formula I is not one of the following compounds:
N-[4-(3-amino-1H-pyrazolo[3,4-b]pyrazin-6-yl)phenyl]-5-chloro-2-fluoro-benzenesulfonamide, and
N-[4-(3-amino-1H-pyrazolo[3,4-b]pyrazin-6-yl)phenyl]-2-chloro-4-trifluoromethyl-benzenesulfonamide,
and in another embodiment the excluded compounds are excluded as the free compounds, i.e. they are not excluded in the form of a salt with an acid or base.

In another embodiment of the invention, the compounds of the formula I are defined as above in their generic definition or in any of the more specific definitions or embodiments, with the proviso that the compound of the formula I is not a compound in which simultaneously the group Ar is selected from the series consisting of 2,4,6-trichloro-phenyl, 5-chloro-2-fluoro-phenyl, 2,4,5-trichloro-phenyl, 2,4,5-trifluoro-phenyl, 5-chloro-2,4-difluoro-phenyl, 2,3,4-trichloro-phenyl, 2,3,4-trifluoro-phenyl and 2-chloro-4-trifluoromethyl-phenyl, n is 0, and R1 is the group —NH$_2$ (amino), and in another embodiment the excluded compounds are excluded as the free compounds, i.e. they are not excluded in the form of a salt with an acid or base.

Another subject of the present invention are processes for the preparation of the compounds of the formula I which are outlined below and by which the compounds of the formula I and intermediates and occurring in the course of their synthesis, and salts thereof, are obtainable. The compounds of the formula I can be prepared by utilizing procedures and techniques which per se are known to a person skilled in the art. In general, 1H-pyrazolo[3,4-b]pyrazine compounds of the formula I can be prepared, for example, in the course of a convergent synthesis, by linking two or more fragments which can be derived retrosynthetically from the formula I. More specifically, suitably substituted starting 1H-pyrazolo[3,4-b]pyrazine derivatives can be employed as building blocks in the preparation of the compounds of formula I, which can be synthesized from suitable precursor compounds, which allow the introduction of a variety of substituents into the various positions of the 1H-pyrazolo[3,4-b]pyrazine system and which can be chemically modified further in order to finally arrive at the compound of the formula I having the desired substituent pattern. For the synthesis of 1H-pyrazolo[3,4-b]pyrazines, use can also be made of procedures and transformations which are described in the literature with respect to indazoles. As reviews in which numerous details and literature references on the chemistry of indazoles and on synthetic procedures for their preparation can be found, J. Eiguero in Comprehensive Heterocyclic Chemistry II, Eds. A. Katritzky, Ch. Rees, E. Scriven, Elsevier 1996, Vol. 3; W. Stadlbauer in Houben-Weyl, Methoden der Organischen Chemie (Methods of Organic Chemistry), Georg Thieme Verlag, Stuttgart, Germany 1994, Vol. Ebb, Hetarene; W. Stadlbauer in Houben-Weyl, Science of Synthesis, Georg Thieme Verlag, Stuttgart, Germany 2002, Vol. 12.2, 227-324, may be mentioned. The starting materials employed in the synthesis of the compounds of the formula I are commercially available or can be prepared according to procedures, or in analogy to procedures, described in the literature or herein. As examples of literature articles relating to synthetic procedures and transformations which can be used in the synthesis of the compounds of the formula I, the following may be mentioned:

Brown et al., Bioorg. Med. Chem. Lett. 2010, 20, 679; Knochel et al., Chem. Commun. 2009, 37, 5615; which relate to the formation of 1H-pyrazolo[3,4-b]pyrazines from 2-acyl-3-chloro-pyrazines and hydrazine US 2010/0029653; which relates to the formation of 1H-pyrazolo[3,4-b]pyrazines from 2-alkynyl-3-chloro-pyrazines and hydrazine Hajos et al., J. Org. Chem. 2008, 73, 3900; Maitte et al., J. Heterocycl. Chem. 1983, 20, 1645; which relate to the formation of 1H-pyrazolo[3,4-b]pyrazines from 2-acyl-pyrazines and hydrazines Stanovnik et al., Heterocycles 1982, 19, 339; Tisler et al., Monatshefte für Chemie, 1982, 113, 731; which relate to the formation of 3-acylamino-1H-pyrazolo[3,4-b]pyrazines from 3-amino-2-[1,2,4]oxadiazol-2-yl-pyrazines in the presence of a base Stanovnik et al., Heterocycles 1982, 19, 339; Tisler et al. Monatshefte für Chemie 1982, 113, 731; Augustynowicz-Kopec et al., Farmaco 2005, 60, 513; Otomasu et al., Chem. Pharm. Bull. 1984, 32, 3361; which relate to the formation 3-amino-1H-pyrazolo[3,4-b]pyrazines from 2-cyano-3-chloro-pyrazines and hydrazines Guarneri et al., J. Heterocycl. Chem. 1986, 23, 585, which relates to the transformation of 1H-6-oxa-1,2,4,7-tetraaza-inden-5-ones into 1H-pyrazolo[3,4-b]pyrazines US 2005/0070542; Sio et al., Farmaco Sci. 1982, 37, 116; Andaluz et al., J. Heterocycl. Chem. 1989, 26, 949; Hofmann et al., Journal fuer Praktische Chemie 1990, 332, 584; Townsend et al., Tetrahedron Lett. 2004, 45, 4105; which relate to the formation of 1H-pyrazolo[3,4-b]pyrazines by reaction of diamino-pyrazoles and amino-nitro-pyrazoles with 2-keto-carboxylic acids and 1,2-dicarbonyl compounds.

In one synthetic approach for the preparation of compounds of the formula I, a compound of the formula II and a compound of the formula III are reacted to give a compound of the formula IV, which can already be the final compound of the formula I, or which is converted into the desired final compound of the formula I.

In an alternative approach, a compound of the formula IV can be obtained by first reacting a compound of the formula V with a compound of the formula III to give a compound of the formula VII, and then reacting the compound of the formula VII with a hydrazine of the formula VI.

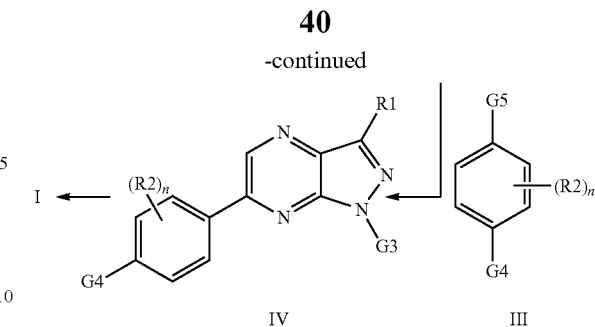

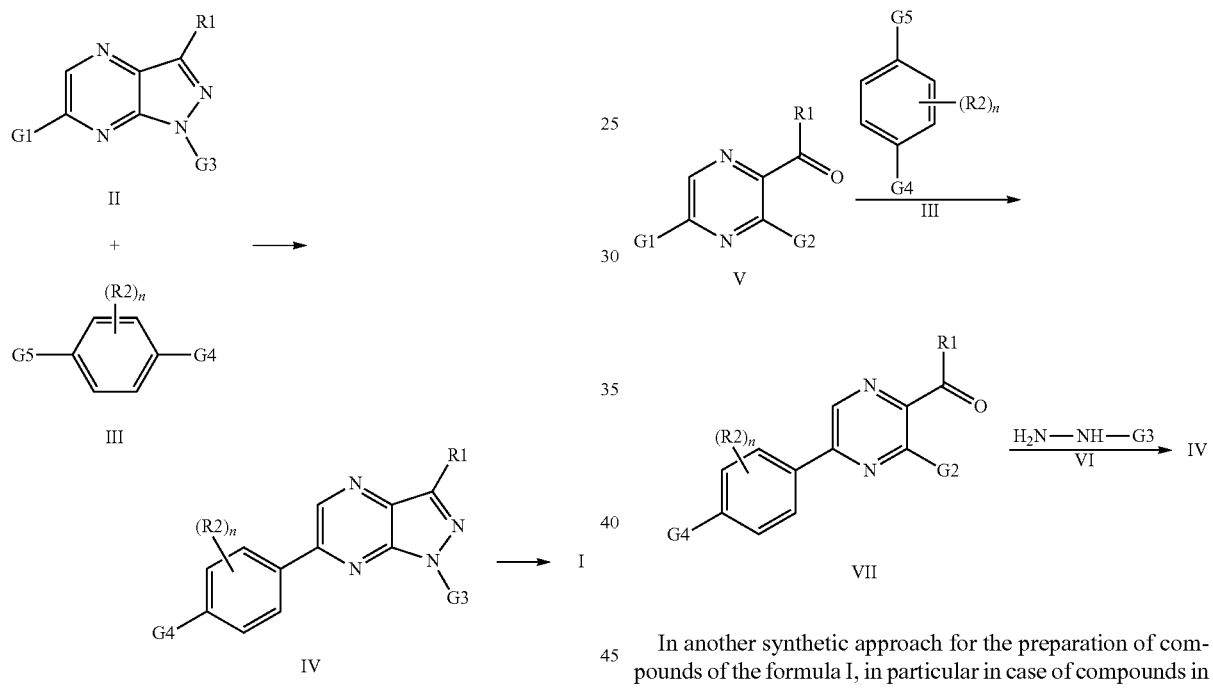

More specifically, in particular in case the group R1 in the compound of the formula I is hydrogen or an optionally substituted alkyl group, according to this approach a compound of the formula II is obtained by reacting a compound of the formula V with a hydrazine of the formula VI, the obained compound of the formula II and a compound of the formula III are reacted to give a compound of the formula IV, and the compound of the formula IV converted into the compound of the formula I.

In another synthetic approach for the preparation of compounds of the formula I, in particular in case of compounds in which the group R1 is bonded via a nitrogen atom to the 1H-pyrazolo[3,4-b]pyrazine ring system, specifically in case of the preparation of compounds in which R1 is an amino group, a compound of the formula X is obtained by reacting a compound of the formula VIII with a hydrazine of the formula VI, and the obtained compound of the formula IX and a compound of the formula III are reacted to give a compound of the formula X, which can already be the final compound of the formula I, or which is converted into the desired final compound of the formula I.

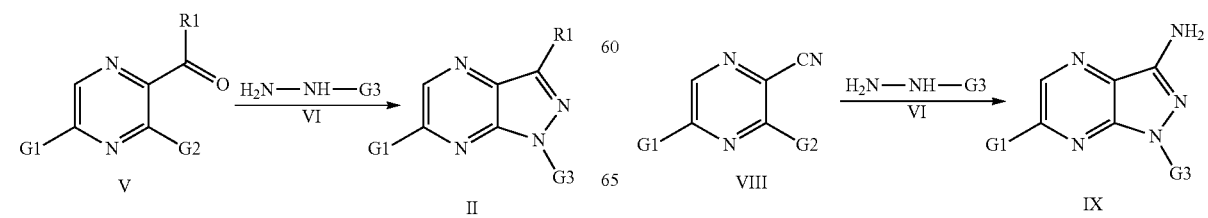

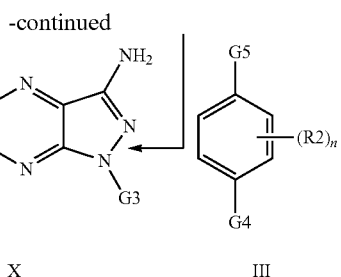

In an alternative approach, a compound of the formula X can be obtained by first reacting a compound of the formula VIII with a compound of the formula III to give a compound of the formula XI, and then reacting the compound of the formula XI with a hydrazine of the formula VI.

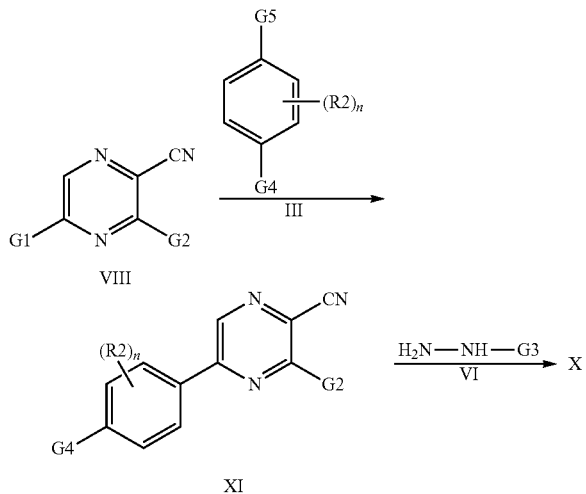

The groups R1 and R2 and the number n in the compounds of the formulae II, III, IV, V, VII, X and XI are defined as in the compounds of the formula I, and additionally can functional groups be present in protected form or in the form of a precursor group which is subsequently converted into the final group. The group G1 in the compounds of the formulae II, V, VIII and IX is a leaving group which can be replaced in a Suzuki-type reaction or Stille-type reaction, such as a halogen atom, in particular bromine or chlorine, or a sulfonyloxy group, in particular trifluoromethanesulfonyloxy, methanesulfonyloxy, benzenesulfonyloxy or tosyloxy (4-methylbenzenesulfonyloxy).

The group G2 in the compounds of formulae V, VII, VIII and XI can be identical to or different from the group G1 and is a leaving group, such as a halogen atom, in particular bromine or chlorine, or a sulfonyloxy group, in particular trifluoromethanesulfonyloxy, methanesulfonyloxy, benzenesulfonyloxy or tosyloxy. The group G3 in the compounds of formulae II, IV, VI, IX and X can be hydrogen, and in this case the compound of the formula VI thus be hydrazine, or it can be a protecting group which is suitable for protecting a ring nitrogen atom in the 1H-pyrazolo[3,4-b]pyrazine ring system or similar ring systems such as the pyrazole ring system, for example, like a tetrahydropyran-2-yl group, a tert-butoxycarbonyl group, an ethoxycarbonyl group, a benzyl group or a substituted benzyl group like a 4-methoxybenzyl group or a 2,5-dimethoxybenzyl group. The group G4 in the compounds of formulae III, IV, VII, X and XI can already be the desired final sulfonamide group of the formula Ar—S(O)$_2$—NH—, in which Ar is defined as in the compounds of the formula I and additionally can functional groups be present in protected form or in the form of a precursor group which is subsequently converted into the final group. G4 can also be a group which can be converted into the desired final sulfonamide group of the formula Ar—S(O)$_2$—NH— at an appropriate stage of the synthesis, for example in the compounds of the formulae IV and X, such as a precursor group like a nitro group which can be reduced to an amino group, or a protected amino group like a tert-butoxycarbonylamino group or a benzyloxycarbonylamino group which can be deprotected to an amino group, or a free amino group, and the amino group then be converted into the group Ar—S(O)$_2$—NH— by reaction with a sulfonyl chloride under standard conditions. The group G5 in the compounds of formula III is a trialkylstannyl group, for example a tri((C$_1$-C$_4$)-alkyl)stannyl group, or a boronic acid group (—B(OH)$_2$) or a boronic acid ester group or cyclic boronic acid ester group, for example a —B(O—(C$_1$-C$_4$)-alkyl)$_2$ group or a 4,4,5,5-tetramethyl-[1,3,2]dioxaborolan-2-yl group, in particular a boronic acid group or a boronic acid ester group or cyclic boronic acid ester group, which allows performing a Suzuki-type reaction or Stille-type reaction for coupling the compounds of the formulae II, V, VIII and IX with the compounds of the formula III. The starting compounds in the synthesis of the compounds of the formula I can also be employed, and the intermediates obtained and/or employed, in the form of salts, for example acid addition salts in case of basic compounds. The intermediates can also be present in another tautomeric form, for example in the case of the compounds of the formulae II or IX in which G3 is hydrogen, which can be present in the form of the respective 2H-pyrazolo[3,4-b]pyrazine derivatives in which the mobile hydrogen atom, which in the compound of the formula II is bonded to the ring nitrogen atom in position 1 of the pyrazolo [3,4-b]pyrazine ring system, is bonded to the ring nitrogen atom in position 2 of the pyrazolo[3,4-b]pyrazine ring system.

The reaction of compounds of the formulae V, VII, VIII and XI with a hydrazine of the formula VI is generally carried out in a protic or aprotic solvent such as water, an alcohol like methanol, ethanol, trifluoroethanol, n-propanol, isopropanol, butanol, isobutanol, tert-butanol, 2-methylbutan-2-ol, 3-methyl-3-pentanol, 3-ethyl-3-pentanol, a hydrocarbon like benzene, toluene, xylene, mesitylene, a nitrile like acetonitrile, an ether like tetrahydrofuran or diglyme (di(2-methoxyethyl) ether), an amide like dimethylformamide, N-methylpyrrolidinone, dimethylacetamide, a sulfoxide like dimethylsulfoxide, or an amine like pyridine, or in a mixture of solvents, at temperatures from about 20° C. to about 200° C., for example at temperatures from about 80° C. to about 120° C. The reaction time generally is from about 30 minutes to about 48 hours, for example from about 5 hours to about 16 hours, depending on the particulars of the specific case and the chosen temperature range. Instead of using conventional heating, the reaction can also be carried out in a microwave oven utilizing microwave radiation at temperatures from about 60° C. to about 200° C., for example at temperatures from about 80° C. to about 120° C. In such case, the reaction time generally is from about 5 minutes to about 12 hours, for example from about 10 minutes to about 3 hours, depending on the particulars of the specific case and the chosen temperature range. The compound of the formula VI can be employed in free form, i.e., not in the form of a salt, for example in the form of a solution in a solvent like ethanol or isopropanol, or in the form of an acid addition salt, for example in the form of a salt with hydrochloric acid. In case a salt is employed, it can be transformed into the free form prior to the reaction or in situ with an organic or inorganic base such as an amine like triethylamine, ethyldiisopropylamine, N-methylmorpholine or 1,8-diazabicyclo[5.4.0]unde-7-ene, an alkoxide like sodium methoxide, sodium ethoxide, potassium methoxide, potassium tert-butoxide, an amide like lithium diisopropylamide or sodium amide, or an alkali metal carbonate like sodium carbonate, potassium carbonate or cesium carbonate, for example.

The reaction of compounds of the formulae II, V, VIII and IX with a compound of the formula III in which G5 is a boronic acid group or a boronic acidester group or cyclic boronic acid ester group, is a Suzuki-type reaction, and is generally carried out in the presence of catalytic palladium compound, for example a palladium(II) salt like palladium (II) acetate or palladium(II) chloride, which can be employed in the presence of a phosphine such as 1,1'-bis(diphenylphosphino)ferrocene, tricyclohexylphosphine or triphenylphosphine, or a palladium complex such as tetrakis(triphenylphosphine)palladium(O), 1,1'-bis(diphenylphosphino)ferrocene-palladium(II)dichloride, palladium(O) bis(tri-tert-butylphosphin) or bis(triphenylphosphine)palladium(II) chloride, and favorably in the presence of a base, for example an alkali metal carbonate or alkali metal phosphate like cesium carbonate, sodium carbonate or tripotassium phosphate, in an inert solvent, such as a hydrocarbon like benzene, toluene or xylene, or an ether like tetrahydrofuran (THF), dioxane or 1,2-dimethoxyethane (DME), or water, or a mixture of solvents, at temperatures from about 20° C. to about 200° C., for example at temperatures from about 80° C. to about 120° C. The reaction time generally is from about 30 minutes to about 48 hours, for example from 30 minutes to about 16 hours, depending on particulars of the specific case and the chosen temperature range. Except for the use of water as solvent, these explanations on the Suzuki-type reactions substantially apply also to reactions with compounds of the formula III in which G5 is a trialkylstannyl group, i.e. Stille-type reactions.

Further, in order to obtain the desired 1H-pyrazolo[3,4-b] pyrazine compound of the formula I, the functional groups introduced into the ring system during the 1H-pyrazolo[3,4-b]pyrazine synthesis can be chemically modified by a variety of reactions and thus the desired groups obtained. For example, a 1H-pyrazolo[3,4-b]pyrazine carrying a hydrogen atom in position 3 can also be obtained by saponification and subsequent decarboxylation of 1H-pyrazolo[3,4-b]pyrazines carrying an ester group in this position. Halogen atoms can be introduced, for example, according to well-known procedures described in the literature. A fluorination of the aromatic substructures of compounds of the formula I can be carried out using a variety of reagents including, for example, N-fluoro-2,4,6-trimethylpyridinium triflate. A chlorination, bromination, or iodination can be accomplished by reaction with the elemental halogens or, for example, by use of N-bromosuccinimide, N-chlorosuccinimide or N-iodosuccinimide and many other reagents well known to the person skilled in the art. By selective halogen/metal exchange, or metalation by selective hydrogen/metal exchange, and subsequent reaction with a wide range of electrophiles, various substituents can be introduced using procedures which are know per se. Among others, halogen atoms, hydroxy groups after conversion into the triflate or nonaflate, for example, or primary amino groups after conversion into the diazonium salt, can directly, or after conversion to the corresponding stannane or boronic acid or boronic acid ester, converted into a variety of other groups like, for example, —CN, —CF$_3$, —C$_2$F$_5$ and ether, acid, amide, amine, alkyl or aryl groups. For such conversions, favorably use can also be made of reactions mediated by transition metals, such as palladium or nickel catalysts or copper salts, as are described in F. Diederich, P. Stang, Metal-catalyzed Cross-coupling Reactions, Wiley-VCH, 1998; M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; T. Sakamoto, K. Ohsawa, J. Chem. Soc. Perkin Trans I, 1999, 2323; D. Nichols, S. Frescas, D. Marona-Lewicka, X. Huang, B. Roth, G. Gudelsky, J. Nash, J. Med. Chem, 1994, 37, 4347; P. Lam, C. Clark, S. Saubern, J. Adams, M. Winters, D. Chan, A. Combs, Tetrahedron Lett., 1998, 39, 2941; D. Chan, K. Monaco, R. Wang, M. Winters, Tetrahedron Lett. 1998, 39, 2933; V. Farina, V. Krishnamurthy, W. Scott, The Stille Reaction, Wiley, 1994; F. Qing et al., J. Chem. Soc. Perkin Trans. I 1997, 3053; S. Buchwald et al. J. Am. Chem. Soc. 2001, 123, 7727; S. Kang et al. Synlett 2002, 3, 427; S. Buchwald et al., Organic Lett. 2002, 4, 581; T. Fuchikami et al., Tetrahedron Lett. 1991, 32, 91; Q. Chen et al., Tetrahedron Lett. 1991, 32, 7689; M. R. Netherton, G. C. Fu, Topics in Organometallic Chemistry 2005, 14, 85-108; A. F. Littke, G. F. Fu, Angew. Chem. Int. Ed. 2002, 41, 4176-4211; A. R. Muci, S. L. Buchwald, Topics in Current Chemistry 2002, 219, 131-209, for example. Nitro groups can be reduced to amino groups with various reducing agents, such as sulfides, dithionites, complex hydrides or by catalytic hydrogenation. A reduction of a nitro group may also be carried out simultaneously with a reaction performed on another functional group, for example when reacting a group like a cyano group with hydrogen sulfide or when hydrogenating a group. Amino groups can then be modified according to standard procedures, for example alkylated by reaction with optionally substituted alkyl halogenides like chlorides, bromides or iodides or sulfonyloxy compounds like tosyloxy, mesyloxy or trifluoromethylsulfonyloxy compounds, preferably in the presence of a base like potassium carbonate, cesium carbonate, sodium hydride or potassium tert-butoxide, or by reductive amination of carbonyl compounds, or acylated by reaction with activated carboxylic acid derivatives such as acid chlorides, anhydrides, activated esters or others or by reaction with carboxylic acids in the presence of an activating agent, or sulfonylated by reaction with sulfonyl chlorides. Ester groups can be hydrolyzed to the corresponding carboxylic acids which after activation can then be reacted with amines under standard conditions. Furthermore, ester or acid groups can be reduced to the corresponding alcohols by many standard procedures, and the resulting hydroxy compounds alkylated. Ether groups, for example benzyloxy groups or other easily cleavable ether groups, can be cleaved to give hydroxy groups which can then be reacted with a variety of agents, for example etherification agents or activating agents allowing replacement of the hydroxy group by other groups. A hydroxy group can also be converted into a leaving group and reacted with various reaction partners under the well-known conditions of the Mitsunobu reaction (O. Mitsunobu, Synthesis 1981, 1), or by further procedures (cf. A. Tunoori, D. Dutta, G. Gunda, Tetrahedron Lett. 39 (1998) 8751; J. Pelletier, S. Kincaid, Tetrahedron Lett. 41 (2000) 797; D. L. Hughes, R. A. Reamer, J. J. Bergan, E. J. J. Grabowski, J. Am. Chem. Soc. 110 (1998) 6487; D. J. Camp, I. D. Jenkins, J. Org. Chem. 54 (1989) 3045; D. Crich, H. Dyker, R. J. Harris, J. Org. Chem. 54 (1989) 257).

The mentioned reactions for the conversion of functional groups are, in general, extensively described in textbooks of organic chemistry like M. Smith, J. March, March's Advanced Organic Chemistry, Wiley-VCH, 2001, and in Houben-Weyl, "Methoden der Organischen Chemie" (Methods of Organic Chemistry), Georg Thieme Verlag, Stuttgart, Germany; "Organic Reactions", John Wiley & Sons, New York; R. C. Larock, "Comprehensive Organic Transformations", Wiley-VCH, $2^{nd}$ ed (1999); B. Trost, I. Fleming (eds.) Comprehensive Organic Synthesis, Pergamon, 1991; A. Katritzky, C. Rees, E. Scriven Comprehensive Heterocyclic Chemistry II, Elsevier Science, 1996; for example, in which details on the reactions and primary source literature can be found. Due to the fact that in the present case the functional groups occur in 1H-pyrazolo[3,4-b]pyrazine compounds, it may in certain cases become necessary to specifically adapt reaction conditions or choose specific reagents from a variety of reagents that can in principle be employed in a conversion reaction, or otherwise take specific measures for achieving a desired conversion, for example to use protection group techniques, as applies in general and is known to the person skilled in the art.

In the course of the preparation of the compounds of the formula I it can generally be advantageous or necessary in order to reduce or prevent undesired reactions or side reactions in the respective synthesis steps, to block functional groups temporarily by protecting groups suited to the specific synthesis problem, or to have them present, or introduce them, in the form of precursor groups, and later convert them into the desired functional groups. Such strategies are well known to a person skilled in the art and are described, for example, in Greene and Wuts, Protective Groups in Organic Synthesis, Wiley, 1991, or P. Kocienski, Protecting Groups, Thieme 1994. Examples of precursor groups are cyano groups and nitro groups. The cyano group can, in a later step, be transformed by hydrolysis into carboxylic acid derivatives or by reduction into aminomethyl groups. Nitro groups can be transformed by reduction like catalytic hydrogenation into amino groups. Examples of protective groups which may be mentioned, are benzyl protective groups, for example benzyl ethers of hydroxy compounds and benzyl esters of carboxylic acids, from which the benzyl group can be removed by catalytic hydrogenation in the presence of a palladium catalyst, tert-butyl protective groups, for example tert-butyl esters of carboxylic acids, from which the tert-butyl group can be removed by treatment with trifluoroacetic acid, acyl protective groups, for example ester and amides of hydroxy compounds and amino compounds, which can be cleaved again by acidic or basic hydrolysis, or alkoxycarbonyl protective groups, for example tert-butoxycarbonyl derivatives of amino compounds, which can be cleaved again by treatment with trifluoroacetic acid. Compounds of the formula I can also be prepared by solid phase techniques. In such a synthetic approach, the solid phase may also be regarded as having the meaning of a protecting group, and cleavage from the solid phase as removal of the protective group. The use of such techniques is known to a person skilled in the art (cf. Burgess K (Ed.), Solid Phase Organic Synthesis, New York, Wiley, 2000). For example, a phenolic hydroxy group can be attached to a trityl-polystyrene resin, which serves as a protecting group, and the molecule cleaved from the resin by treatment with trifluoroacetic acid or another acid at a later stage of the synthesis.

As is usual and applies to all reactions performed in the course of the synthesis of a compound of the formula I, appropriate details of the conditions applied in a specific preparation process, including the solvent, a base or acid, the temperature, the order of addition, the molar ratios and other parameters, are routinely chosen by the skilled person in view of the characteristics of the starting compounds and the target compound and the other particularities of the specific case. As is also known by the skilled person, not all processes described herein will in the same way be suitable for the preparation of all compounds of the formula I and their intermediates, and adaptations have to be made. In all processes for the preparation of the compounds of the formula I, workup of the reaction mixture and the purification of the product is performed according to customary methods known to the skilled person which include, for example, quenching of a reaction mixture with water, adjustment of a certain pH, precipitation, extraction, drying, concentration, crystallization, distillation and chromatography. As further examples of methods applicable in the synthesis of the compounds of the formula I, microwave assistance for speeding-up, facilitating or enabling reactions, as described by P. Lidstrom, J. Tierney, B. Wathey, J. Westman, Tetrahedron, 57 (2001), 9225, for example, may be mentioned, and modern separation techniques like preparative high pressure liquid chromatography (HPLC), which can be used for separating mixtures of positional isomers which may occur in any reactions. Also for the characterization of the products customary methods are used such as NMR, IR and mass spectroscopy.

Another subject of the present invention are the novel starting compounds and intermediates occurring in the synthesis of the compounds of the formula I, including the compounds of the formulae II, III, IV, V, VII, VIII, IX, X and XI, wherein the groups R1, R2, G1, G2, G3, G4 and G5 and the number n are defined as above, in any of their stereoisomeric forms or a mixture of stereoisomeric forms in any ratio, and their salts, and their use as synthetic intermediates or starting compounds. All general explanations, specifications of embodiments and definitions of numbers and groups given above with respect to the compounds of the formula I apply correspondingly to the said intermediates and starting compounds. A subject of the invention are in particular the novel specific starting compounds and intermediates described herein. Independently thereof whether they are described as a free compound and/or as a specific salt, they are a subject of the invention both in the form of the free compounds and in the form of their salts, and if a specific salt is described, additionally in the form of this specific salt.

The compounds of the present invention are SGK inhibitors, which are capable of inhibiting an exaggerated, or inappropriate, activity of SGK in pathological conditions and are therefore suitable for the prophylaxis and therapy of the diseases mentioned above and below. In particular, they are highly active inhibitors of the SGK-1 enzyme. They are selective SGK-1 inhibitors inasmuch as they do not substantially inhibit or promote the activity of other enzymes and receptors whose activation or inhibition is not desired. The activity of the compounds of the formula I can be determined, for example, in the assays described below or in other in vitro, ex vivo or in vivo assays known to the person skilled in the art. For example, the ability of the compounds to inhibit the SGK enzyme may be measured by methods similar to those described in D. Perrin et al., Expert Opin. Drug Discov. (2010) 5, 51-63, and by the assay described below. With respect to SGK-1 inhibitory activity, one embodiment of the invention comprises compounds which have an $IC_{50}$ value of <1 µM, in another embodiment of <0.1 µM, in another embodiment of <0.01 µM, for SGK-1 inhibition as determined in the assay described below, and which in a further embodiment do not substantially influence the activity of other enzymes and receptors whose inhibition or activation is not desired. The ability of the compounds to inhibit the SGK-1 mediated glycogen synthase kinase 3beta (GSK3beta) phosphorylation in a cellular setting may be measured by methods similar to those described by H. Sakoda et al. J. Biol. Chem. 2003, 278, 25802-25807, and by the method described below. The ability of the compounds to inhibit SGK1 dependent activation of epithelial Na$^+$ channel (ENaC) currents in cell monolayers may be measured by methods similar to those described by D. Alvarez de la Rosa et al., Am. J. Physiol. Cell Physiol. 284:404-414, 2003, D. Alvarez de la Rosa et al.; J. Gen. Physiol. 2004 October; 124(4):395-407, and by the assay described below. The inappropriate SGK-1 activity referred to herein is any SGK-1 activity that deviates from the expected normal SGK-1 activity. Inappropriate SGK-1 activity may take the form of, for example, an abnormal increase in activity, or an aberration in the timing and/or control of SGK-1 activity. Such inappropriate activity may result then, for example, from overexpression or mutation of the protein kinase leading to inappropriate or uncontrolled activation. As SGK-1 inhibitors, the compounds of the formula I and their pharmaceutically acceptable salts are generally suitable for the prophylaxis and/or therapy of conditions in which the inappropriate activity of SGK-1 enzyme plays a role or has an undesired extent, or which can favorably be influenced by inhibiting the SGK-1 enzyme or decreasing the activity, or for the prevention, alleviation or cure of which an inhibition of SGK-1 or a decrease in the activity is desired by the physician.

Because of their pharmacological properties, the compounds of the present invention are suitable for the treatment of all disorders in the progression of which an enhanced activity of SGK enzyme is involved. These include the indications described in the introduction. The invention relates in particular to the use of a compound of the formula I or a pharmaceutically acceptable salt thereof for the treatment of degenerative joint disorders and degenerative cartilage changes including osteoarthritis, osteoarthrosis, rheumatoid arthritis, spondylosis, chondrolysis following joint trauma and prolonged joint immobilization after meniscus or patella injuries or ligament tears, connective tissue disorders such as collagenoses, periodontal disorders, wound-healing disturbances, diabetes including diabetes mellitus, diabetic nephropathy, diabetic neuropathy, diabetic angiopathy and microangiopathy, obesity, metabolic syndrome (dyslipidaemia), systemic and pulmonary hypertension, cerebral infarctions, cardiovascular diseases including cardiac fibrosis after myocardial infarction, cardiac hypertrophy and heart failure, arteriosclerosis, renal diseases including glomerulosclerosis, nephrosclerosis, nephritis, nephropathy and electrolyte excretion disorder, any type of fibrosis and inflammatory processes including liver cirrhosis, lung fibrosis, fibrosing pancreatitis, rheumatism, arthritis, gout, Crohn's disease, chronic bronchitis, radiation fibrosis, sclerodermatitis, cystic fibrosis, scar formation, Alzheimer's disease, pain including acute pain like pain following injuries, post-operative pain, pain in association with an acute attack of gout and acute pain following jaw-bone surgery interventions, and chronic pain like pain associated with chronic musculoskeletal diseases, back pain, pain associated with osteoarthritis or rheumatoid arthritis, pain associated with inflammation, amputation pain, pain associated with multiple sclerosis, pain associated with neuritis, pain associated with carcinomas and sarcomas, pain associated with AIDS, pain associated with chemotherapy, trigeminus neuralgia, headache, migraine cephalalgia, neuropathic pains, post-herpes zoster neuralgia, chronic disorders of the locomotor system such as inflammatory, immunologically or metabolically related acute and chronic arthritides, arthropathies, myalgias and disturbances of bone metabolism, peptic ulcers, especially in forms that are triggered by stress, tinnitus, bacterial infections, glaucoma, cataracts, coagulopathies including dysfibrinogenaemia, hypoproconvertinaemia, haemophilia B, Stuart-Prower defect, prothrombin complex deficiency, consumption coagulopathy, fibrinolysis, immunokoagulopathy or complex coagulopathies, and to the use in tumor therapy including inhibition of tumor growth and tumor metastases, the use in anti-infective therapy, the use for increasing the learning ability and attention, the use for counteracting cellular aging and stress and thus increasing life expectancy and fitness in the elderly, and the use in states of neuronal excitability including epilepsy. The treatment of diseases is to be understood herein as generally meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence. For example, in patients who on account of their disease history are susceptible to myocardial infarction, by means of the prophylactic or preventive medicinal treatment the occurrence or re-occurrence of a myocardial infarct can be prevented or its extent and sequelae decreased. The treatment of diseases can occur both in acute cases and in chronic cases.

The compounds of the formula I and their pharmaceutically acceptable salts can therefore be used in animals, in particular in mammals and specifically in humans, as a pharmaceutical or medicament on their own, in mixtures with one another, or in the form of pharmaceutical compositions. A subject of the present invention also are the compounds of the formula I and their pharmaceutically acceptable salts for use as a pharmaceutical. A subject of the present invention also are pharmaceutical compositions and medicaments which comprise at least one compound of the formula I and/or a pharmaceutically acceptable salt thereof as an active ingredient, in an effective dose for the desired use, and a pharmaceutically acceptable carrier, i.e. one or more pharmaceutically innocuous, or nonhazardous, vehicles and/or excipients, and optionally one or more other pharmaceutical active compounds.

A subject of the present invention also are the compounds of the formula I and their pharmaceutically acceptable salts for use in the treatment of the diseases mentioned above or below, including the treatment of any one of the mentioned diseases, for example the treatment of degenerative joint disorders, degenerative cartilage changes, diabetes, cardiovascular diseases, fibrosis, inflammatory processes, pain, tumors or cerebral infarctions, wherein treatment of diseases comprises their therapy and prophylaxis as mentioned above, or for use as an inhibitor of serum and glucocorticoid regulated kinase (SGK). A subject of the present invention also are the use of the compounds of the formula I and their pharmaceutically acceptable salts for the manufacture of a medicament for the treatment of the diseases mentioned above or below, including the treatment of any one of the mentioned diseases, for example inhibitor the treatment of degenerative joint disorders, degenerative cartilage changes, diabetes, cardiovascular diseases, fibrosis, inflammatory processes, pain, tumors or cerebral infarctions, wherein treatment of diseases comprises their therapy and prophylaxis as mentioned above, or a medicament for inhibition of serum and glucocorticoid regulated kinase (SGK). A subject of the present invention also are methods for the treatment of the diseases mentioned above or below, including the treatment of any one of the mentioned diseases, for example the treatment of degenerative joint disorders, degenerative cartilage changes, diabetes, cardiovascular diseases, fibrosis, inflammatory processes, pain, tumors or cerebral infarctions, wherein treatment of diseases comprises their therapy and prophylaxis as mentioned above, and a method for inhibiting serum and glucocorticoid regulated kinase (SGK), which comprise administering an efficacious amount of at least one compound of the formula I and/or a pharmaceutically acceptable salt thereof to a human or an animal which is in need thereof.

The compounds of the formula I and their pharmaceutically acceptable salts, and pharmaceutical compositions and medicaments comprising them, can be administered enterally, for example by oral or rectal administration in the form of pills, tablets, lacquered tablets, coated tablets, granules, hard and soft gelatin capsules, solutions, syrups, emulsions, suspensions, aerosol mixtures or suppositories, or parenterally. Parenteral administration can be carried out, for example, intravenously, intraarticularly, intraperitoneally, intramuscularly or subcutaneously, in the form of injection solutions or infusion solutions, microcapsules, implants or rods, or percutaneously, transdermally or topically, for example in the form of ointments, solutions or tinctures, or in other ways, for example in the form of aerosols or nasal sprays. The preferred form of administration depends on the particulars of the specific case.

Pharmaceutical formulations adapted for transdermal administration can be administered as plasters for extended, close contact with the epidermis of the recipient. For topical administration, formulations such as ointments, creams, suspensions, lotions, powders, solutions, pastes, gels, sprays, aerosols or oils can be used. For the treatment of the eye or other external tissue, for example mouth and skin, suitable formulations are topical ointments or creams, for example. In the case of ointments, the active ingredient can be employed either with a paraffinic or a water-miscible cream base. Alternatively, the active ingredient can be formulated to give a cream with an oil-in-water cream base or a water-in-oil base. Pharmaceutical formulations adapted for topical application to the eye include eye drops, in which the active ingredient is dissolved or suspended in a suitable carrier, in particular an aqueous solvent.

The pharmaceutical compositions according to the invention are prepared in a manner known per se and familiar to the person skilled in the art by admixing one or more pharmaceutically acceptable inert inorganic and/or organic vehicles and excipients with one or more compounds of the formula I and/or pharmaceutically acceptable salts thereof, and bringing them into a suitable form for dosage and administration, which can then be used in human medicine or veterinary medicine. For the production of pills, tablets, coated tablets and hard gelatin capsules it is possible to use, for example, lactose, cornstarch or derivatives thereof, talc, stearic acid or its salts. For the production of gelatin capsules and suppositories fats, waxes, semisolid and liquid polyols, natural or hardened oils, for example, can be used. For the production of solutions, for example injection solutions, or of emulsions or syrups water, saline, alcohols, glycerol, polyols, sucrose, invert sugar, glucose, vegetable oils, for example, can be used, and for the production of microcapsules, implants or rods copolymers of glycolic acid and lactic acid, for example, can be used. The pharmaceutical compositions normally contain from about 0.5% to 90% by weight of the compounds of the formula I and/or their pharmaceutically acceptable salts. The amount of the active ingredient of the formula I and/or its pharmaceutically acceptable salts in the pharmaceutical compositions normally is from about 0.5 mg to about 1000 mg, preferably from about 1 mg to about 500 mg per unit dose. Depending on the kind of the pharmaceutical composition and other particulars of the specific case, the amount may deviate from the indicated ones In addition to the active ingredients of the formula I and/or their pharmaceutically acceptable salts and to vehicles, or carrier substances, the pharmaceutical compositions can contain excipients, or auxiliaries or additives, such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their pharmaceutically acceptable salts. In case a pharmaceutical composition contains two or more compounds of the formula I, the selection of the individual compounds can aim at a specific overall pharmacological profile of the pharmaceutical composition. For example, a highly potent compound with a shorter duration of action may be combined with a long-acting compound of lower potency. The flexibility permitted with respect to the choice of substituents in the compounds of the formula I allows a great deal of control over the biological and physicochemical properties of the compounds and thus allows the selection of such desired compounds.

When using the compounds of the formula I, the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches known to the person skilled in the art. In general, the daily dose for achieving the desired results in an adult weighing about 75 kg is from about 0.01 mg/kg to about 100 mg/kg, preferably from about 0.1 mg/kg to about 50 mg/kg, in particular from about 0.1 mg/kg to about 10 mg/kg, in each case in mg per kg of body weight. The daily dose can be divided, in particular in the case of the administration of relatively large amounts, into several, for example 2, 3 or 4, part administrations. As usual, depending on individual behavior it may be necessary to deviate upwards or downwards from the daily dose indicated.

The compounds of the present invention are also useful as standard or reference compounds, for example as a quality standard or control, in tests or assays involving the inhibition of the SGK enzyme. For such use, for example in pharmaceutical research involving the SGK enzyme, the compounds may be provided in a commercial kit. For example, a compound of the present invention can be used as a reference in an assay to compare its known activity to a compound with an unknown activity. Furthermore, the compounds of the formula I can be used as synthesis intermediates for the preparation of other compounds, in particular of other pharmaceutical active compounds, which may be obtained from the compounds of the formula I by introduction of substituents or modification of functional groups, for example.

The following examples illustrate the present invention.

EXAMPLES

When in the final step of the synthesis of an example compound an acid such as trifluoroacetic acid or acetic acid was used, for example when trifluoroacetic acid was employed to remove an acid-labile protecting group containing a tert-butyl group, or when a compound was purified by chromatography using an eluent which contained such an acid, in some cases, depending on the work-up procedure, for example the details of a freeze-drying process, the compound was obtained partially or completely in the form of a salt of the acid used, for example in the form of the salt with acetic acid salt or trifluoroacetic acid salt. In the names of the example compounds and the structural formulae such contained trifluoroacetic acid or acetic acid is not specified.

The prepared compounds were in general characterized by spectroscopic data and chromatographic data, in particular mass spectra (MS) and/or nuclear magnetic resonance (NMR) spectra. In the NMR characterization, the chemical shift δ (in ppm), the number of hydrogen atoms (H), the coupling constant J (in Hz) and the multiplicity (s: singlet, d: doublet, dd: double doublet, t: triplet, m: multiplet; br: broad) of the peaks are given. In the MS characterization, the mass number (m/e) of the peak of the molecular ion (M) or of a related ion such as the ion (M+1), i.e. the protonated molecular ion (M+H), or the ion (M−1), which was formed depending on the ionization method used, is given. Generally, the ionization method was electrospray ionization (ESI+ or ES−).

Abbreviations
DCM Dichloromethane
dioxane [1,4]Dioxane
DMF N,N-Dimethylformamide
DMSO Dimethylsulfoxide
EtOAc Ethyl acetate
iPrOH Isopropanol
MeCN Acetonitrile
RT Room temperature (20° C. to 25° C.)
TFA Trifluoroacetic acid Example 1

N-[4-(3-Amino-1H-pyrazolo[3,4-b]pyrazin-6-yl) phenyl]-2,3-dichloro-benzenesulfonamide

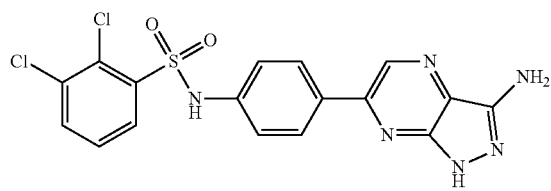 [SMILES: Nc1n[nH]c2nc(-c3ccc(NS(=O)(=O)c4cccc(Cl)c4Cl)cc3)cnc12]

(i) 2,3-Dichloro-N-[4-(4,4,5,5-tetramethyl-[1,3,2] dioxaborolan-2-yl)-phenyl]-benzenesulfonamide The title compound was prepared by adding 2,3-dichlorobenzenesulfonyl chloride (11.2 g) and 4-(4,4,5,5-tetramethyl-[1,3,2]dioxaborolan-2-yl)-phenylamine (10.0 g) to a reaction vessel containing a magnetic stirring bar, followed by 200 ml dry DCM and 4.1 ml pyridine. The reaction mixture was stirred at RT for 20 h before being cooled on an ice-bath and quenched with 1M aqueous sodium hydroxide solution. The organic phase was separated and the aqueous phase acidified with 2M aqueous hydrochloric acid and extracted three times with EtOAc. The combined organic phases were washed with brine and dried over sodium sulfate and evaporated to afford the crude product. Purification by flash chromatography on silica gel using a mixture of EtOAc and heptane as the eluent afforded 2,3-dichloro-N-[4-(4,4,5,5-tetramethyl-[1,3,2]dioxaborolan-2-yl)-phenyl]-benzenesulfonamide as a colorless solid after evaporation of the solvents under reduced pressure. Yield: 15.11 g (77%).

MS (ES−): m/e=426.1 (M−H).

(ii) 2,3-Dichloro-N-[4-(6-chloro-5-cyano-pyrazin-2-yl)phenyl]benzenesulfonamide 2,3-Dichloro-N-[4-(4,4,5,5-tetramethyl-[1,3,2]dioxaborolan-2-yl)-phenyl]-benzenesulfonamide (5.78 g) was added to a reaction vessel containing a magnetic stirring bar together with 3,5-dichloro-pyrazine-2-carbonitrile (2.35 g), 1,1'-bis(diphenylphosphino)ferrocene-palladium(II) dichloride (Pd(dppf)$_2$Cl$_2$) (791 mg) and cesium carbonate (13.2 g), followed by 100 ml dioxane and 10 ml water, and the mixture heated to 100° C. under stirring. After 3 h the reaction mixture was cooled to RT and quenched with a saturated aqueous sodium bicarbonate solution (100 ml) and extracted with EtOAc (3×200 ml). The combined aqueous phases were dried over sodium sulfate, filtered and evaporated to afford the crude product as a brown oil. Purification by flash chromatography on silica gel using a mixture of EtOAc and heptane as the eluent afforded 2,3-dichloro-N-[4-(6-chloro-5-cyano-pyrazin-2-yl)-phenyl]-benzenesulfonamide as a light brown foam after evaporation of the solvents under reduced pressure. Yield: 4.32 g (73%).

MS (ES−): m/e=436.0 (M−H).

(iii) N-[4-(3-Amino-1H-pyrazolo[3,4-b]pyrazin-6-yl) phenyl]-2,3-dichloro-benzenesulfonamide 2,3-Dichloro-N-[4-(6-chloro-5-cyano-pyrazin-2yl)-phenyl]-benzenesulfonamide (1.0 g) was suspended in a mixture of 5 ml iPrOH and 5 ml 35% hydrazine in water at RT and heated to 120° C. by microwave irradiation for 20 min under stirring in a sealed vessel. The reaction mixture was left to cool to RT. The precipitate was filtered off and washed with water to give the title compound as a yellow solid after drying under vacuum. Yield: 536 mg (54%).

$^1$H-NMR (DMSO-d$_6$): δ (ppm)=5.67 (br s, 2H), 7.26 (d, J=8.8 Hz, 2H), 7.58 (t, J=8.0 Hz, 1H), 7.93 (dd, J=1.4, 8.0 Hz, 1H), 8.06 (d, J=8.8 Hz, 2H), 8.11 (dd, J=1.5, 8.0 Hz, 1H), 8.86 (s, 1H), 12.30 (s, 1H).

MS (ES+): m/e=435.2 (M+H), chloro pattern.

Example 2

2,5-Dichloro-N-[4-(1H-pyrazolo[3,4-b]pyrazin-6-yl) phenyl]benzenesulfonamide hydrochloride

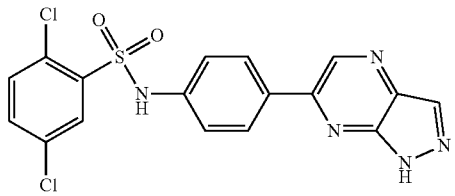 [SMILES: O=S(=O)(Nc1ccc(-c2cnc3cn[nH]c3n2)cc1)c1cc(Cl)ccc1Cl]

(i) 2,5-Dichloro-N-[4-(4,4,5,5-tetramethyl-[1,3,2] dioxaborolan-2-yl)-phenyl]-benzenesulfonamide To a solution of 10 g of 4-(4,4,5,5-tetramethyl-[1,3,2]dioxaborolan-2-yl)-phenylamine in 100 ml DCM and 4 ml pyridine, 11.6 g of 2,5-dichloro-benzenesulfonyl chloride were added, and the reaction mixture was stirred for 16 h at RT. Then, the solvents were removed under reduced pressure and the crude product was purified by chromatography on silica gel eluting with a gradient of n-heptane/EtOAc. The fractions containing the product were combined and the solvent evaporated under reduced pressure. Yield: 17.9 g.

(ii) 2,5-Dichloro-N-[4-(6-chloro-5-formyl-pyrazin-2-yl)-phenyl]-benzenesulfonamide A solution of 100 mg of 3,5-dichloro-pyrazine-2-carbaldehyde, 241 mg 2,5-dichloro-N-[4-(4,4,5,5-tetramethyl-[1,3,2]dioxaborolan-2-yl)-phenyl]-benzenesulfonamide and 552 mg of cesium carbonate in 3.4 ml of dioxane and 0.6 ml of water was purged with argon. Then, 33 mg of 1,1'-bis(diphenylphosphino)ferrocene-palladium(II) dichloride were added and the reaction mixture was heated to 100° C. After 40 min, the reaction mixture was cooled to RT and diluted with water. After filtration through a chem Elut® cartridge by eluting with EtOAc, the solvents were removed under reduced pressure. The crude product was purified by chromatography on silica gel eluting with a gradient of n-heptane/EtOAc and finally methanol. The fractions containing the product were combined and the solvent evaporated under reduced pressure. Yield: 90 mg.

(iii) 2,5-Dichloro-N-[4-(1H-pyrazolo[3,4-b]pyrazin-6-yl)phenyl]benzenesulfonamide To a solution of 90 mg of 2,5-dichloro-N-[4-(6-chloro-5-formyl-pyrazin-2-yl)-phenyl]benzenesulfonamide in 0.7 ml isopropanol 0.7 ml of a hydrazine solution (35% in isopropanol) were added and the reaction mixture was heated for 20 min to 120° C. by using microwave irradiation (Biotage Initiator™ apparatus). The reaction mixture was cooled to RT and diluted with acetic acid (20%). The precipitated product was collected by filtration and purified by preparative HPLC (C18 reversed phase column, elution with a water/MeCN gradient with 0.1% TFA). The fractions containing the product were lyophilized to yield the title compound in the form of its salt with trifluoroacetic acid as a solid, which was dissolved in 1 ml of a water/acetonitrile mixture. 0.5 ml of a 1 M aqueous hydrochloric acid was added and the solution was again lyophilized to yield the title compound in the form of 2,5-dichloro-N-[4-(1H-pyrazolo[3,4-b]pyrazin-6-yl)phenyl]benzenesulfonamide hydrochloride. Yield: 5.2 mg.

MS (ES+): m/e=420.2 (M+H), chloro pattern.

Example 3

2,5-Dichloro-N-[2-fluoro-4-(1H-pyrazolo[3,4-b]pyrazin-6-yl)phenyl]benzenesulfonamide hydrochloride

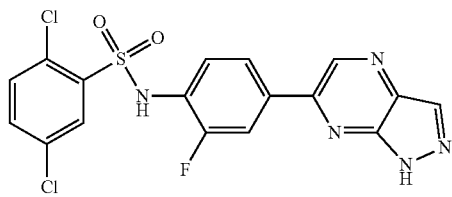 [SMILES: O=S(=O)(Nc1ccc(-c2cnc3cn[nH]c3n2)cc1F)c1cc(Cl)ccc1Cl]

(i) 2,5-Dichloro-N-[2-fluoro-4-(4,4,5,5-tetramethyl-1,3,2-dioxaborolan-2-yl)phenyl]benzenesulfonamide To a solution of 1.5 g of 2-fluoro-4-(4,4,5,5-tetramethyl-1,3,2-dioxaborolan-2-yl)aniline in 17 ml DCM and 0.5 ml pyridine, 1.5 g of 2,5-dichloro-benzenesulfonyl chloride were added, and the reaction mixture was stirred for 16 h at RT. Then the solvents were removed under reduced pressure and the crude product was purified by chromatography on silica gel eluting with a gradient of n-heptane/EtOAc. The fractions containing the product were combined and the solvent evaporated under reduced pressure. Yield: 2.2 g.

(ii) 2,5-Dichloro-N-[4-(6-chloro-5-formyl-pyrazin-2-yl)-2-fluoro-phenyl]benzenesulfonamide A solution of 100 mg of 3,5-dichloro-pyrazine-2-carbaldehyde, 252 mg 2,5-dichloro-N-[2-fluoro-4-(4,4,5,5-tetramethyl-1,3,2-dioxaborolan-2-yl)phenyl]benzenesulfonamide and 552 mg of cesium carbonate in 3.4 ml of dioxane and 0.6 ml of water was purged with argon. Then, 33 mg of 1,1'-bis(diphenylphosphino)ferrocene-palladium(II)dichloride were added and the reaction mixture was heated to 100° C. After 6 h the reaction mixture was cooled to RT and diluted with water. After filtration through a chem Elut® cartridge by eluting with EtOAc the solvents were removed under reduced pressure. The crude product was purified by chromatography on silica gel eluting with a gradient of n-heptane/EtOAc and finally methanol. The fractions containing the product were combined and the solvent evaporated under reduced pressure. Yield: 180 mg.

(iii) 2,5-Dichloro-N-[2-fluoro-4-(1H-pyrazolo[3,4-b]pyrazin-6-yl)phenyl]benzenesulfonamide To a solution of 120 mg of 2,5-dichloro-N-[4-(6-chloro-5-formyl-pyrazin-2-yl)-2-fluoro-phenyl]benzenesulfonamide in 0.9 ml isopropanol 0.9 ml of a hydrazine solution (35% in isopropanol) were added and the reaction mixture was heated for 20 min to 120° C. by using microwave irradiation (Biotage Initiator™ apparatus). The reaction mixture was cooled to RT and diluted with acetic acid (20%). The precipitated product was collected by filtration. The crude product was purified by preparative HPLC (C18 reversed phase column, elution with a water/MeCN gradient with 0.1% TFA). The fractions containing the product were lyophilized to yield the pure product in the form of its salt with trifluoroacetic acid as a solid, which was dissolved in 1 ml of a water/acetonitrile mixture. 0.5 ml of a 1 M aqueous hydrochloric acid was added and the solution was again lyophilized to yield the title compound in the form of 2,5-dichloro-N-[2-fluoro-4-(1H-pyrazolo[3,4-b]pyrazin-6-yl)phenyl]benzenesulfonamide hydrochloride. Yield: 2.2 mg.

MS (ES+): m/e=438.2 (M+H), chloro pattern.

Example 4

2,3-Dichloro-N-[2-fluoro-4-(1H-pyrazolo[3,4-b]pyrazin-6-yl)-phenyl]-benzenesulfonamide

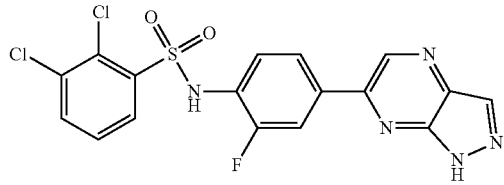 [SMILES: O=S(=O)(Nc1ccc(-c2cnc3cn[nH]c3n2)cc1F)c1cccc(Cl)c1Cl]

The title compound was prepared by adapting the procedures described in example 3, employing 2,3-dichlorobenzenesulfonyl chloride used instead of 2,5-dichloro-benzenesulfonyl chloride.

MS (ES+): m/e=438.1 (M+H), chloro pattern.

Example 5

N-[4-(3-Amino-1H-pyrazolo[3,4-b]pyrazin-6-yl)phenyl]-2,5-dichloro-benzenesulfonamide

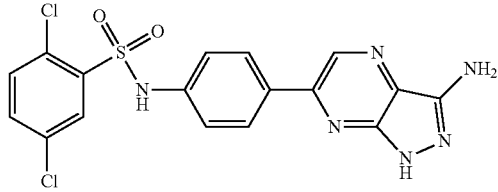

The title compound was prepared in 22% yield according to the procedure described in example 1, employing 2,5-dichloro-benzenesulfonyl chloride instead of 2,3-dichloro-benzenesulfonyl chloride as starting material. The following modification was made. The crude reaction mixture was evaporated to dryness, redissolved in DMF and purified by preparative HPLC (C18 reversed phase column, elution with a water/MeCN gradient with 0.1% TFA). The fractions containing the product were lyophilized to yield the title compound in the form of its salt with trifluoroacetic acid.

$^1$H-NMR (DMSO-$d_5$): δ (ppm)=7.28 (d, J=8.8 Hz, 2H), 7.70 (d, J=8.6 Hz, 1H), 7.75 (dd, J=2.5, 8.6 Hz, 1H), 8.08 (d, J=2.5 Hz, 1H), 8.09 (d, J=8.8 Hz, 2H), 8.89 (s, 1H), 11.13 (s, 1H).

MS (ES+): m/e=434.9 (M+H), chloro pattern.

Example 6

N-[4-(3-Amino-1H-pyrazolo[3,4-b]pyrazin-6-yl)-2-fluoro-phenyl]-5-chloro-2-fluoro-benzenesulfonamide

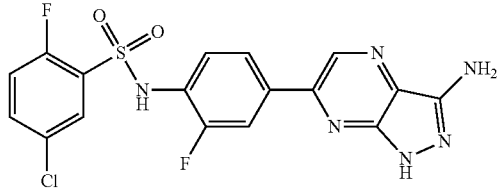

The title compound was prepared in 6% yield according to the procedure described in example 1, employing 5-chloro-2-fluoro-benzenesulfonyl chloride instead of 2,3-dichloro-benzenesulfonyl chloride and 2-fluoro-4-(4,4,5,5-tetramethyl-[1,3,2]dioxaborolan-2-yl)-phenylamine instead of 4-(4,4,5,5-tetramethyl-[1,3,2]dioxaborolan-2-yl)-phenylamine as starting material. The following modification was made. The crude reaction mixture was evaporated to dryness, redissolved in DMF and purified by preparative HPLC (C18 reversed phase column, elution with a water/MeCN gradient with 0.1% TFA). The fractions containing the product were lyophilized to yield the title compound in the form of its salt with trifluoroacetic acid.

MS (ES+): m/e=437.0 (M+H), chloro pattern.

Example 7

N-[4-(3-Amino-1H-pyrazolo[3,4-b]pyrazin-6-yl)-2-fluoro-phenyl]-2,5-dichloro-benzenesulfonamide

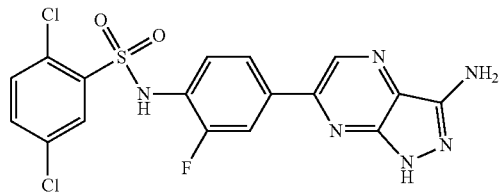 [SMILES: Nc1n[nH]c2nc(-c3ccc(NS(=O)(=O)c4cc(Cl)ccc4F)c(F)c3)cnc12]

The title compound was prepared in 5% yield according to the procedures described in example 1, employing 2,5-dichloro-benzenesulfonyl chloride instead of 2,3-dichloro-benzenesulfonyl chloride and 2-fluoro-4-(4,4,5,5-tetramethyl-[1,3,2]dioxaborolan-2-yl)-phenylamine instead of 4-(4,4,5,5-tetramethyl-[1,3,2]dioxaborolan-2-yl)-phenylamine as starting material. The following modification was made. The crude reaction mixture was evaporated to dryness, redissolved in DMF and purified by preparative HPLC (C18 reversed phase column, elution with a water/MeCN gradient with 0.1% TFA). The fractions containing the product were lyophilized to yield the title compound in the form of its salt with trifluoroacetic acid.

MS (ES+): m/e=452.9 (M+H), chloro pattern.

Example 8

N-[4-(3-Amino-1H-pyrazolo[3,4-b]pyrazin-6-yl)phenyl]-5-chloro-2-hydrazino-benzenesulfonamide

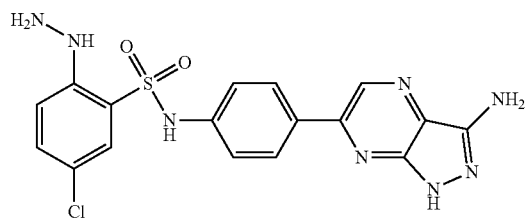 [SMILES: NNc1ccc(Cl)cc1S(=O)(=O)Nc1ccc(-c2cnc3c(N)n[nH]c3n2)cc1]

The title product was isolated as a by-product in the synthesis of N-[4-(3-amino-1H-pyrazolo[3,4-b]pyrazin-6-yl)phenyl]-5-chloro-2-fluoro-benzenesulfonamide.

MS (ES+): m/e=431.0 (M+H), chloro pattern.

Example 9

N-[4-(3-Amino-1H-pyrazolo[3,4-b]pyrazin-6-yl)-2-fluoro-phenyl]-2,3-dichloro-benzenesulfonamide

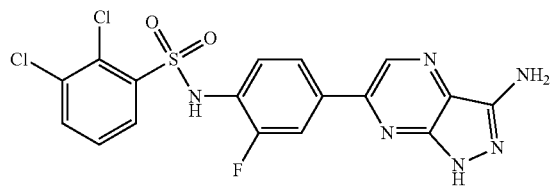 [SMILES: Nc1n[nH]c2nc(-c3ccc(NS(=O)(=O)c4cccc(Cl)c4Cl)c(F)c3)cnc12]

The title compound was prepared in 4% yield according to the procedure described in example 1, employing 2-fluoro-4-(4,4,5,5-tetramethyl-[1,3,2]dioxaborolan-2-yl)-phenylamine instead of 4-(4,4,5,5-tetramethyl-[1,3,2]dioxaborolan-2-yl)-phenylamine as starting material. The following modification was made. The crude reaction mixture was evaporated to dryness, redissolved in DMF and purified by preparative HPLC (C18 reversed phase column, elution with a water/MeCN gradient with 0.1% TFA). The fractions containing the product were lyophilized to yield the title compound in the form of its salt with trifluoroacetic acid.

MS (ES+): m/e=452.9 (M+H), chloro pattern.

Example 10

2,3-Dichloro-N-[4-(3-methyl-1H-pyrazolo[3,4-b]pyrazin-6-yl)phenyl]benzenesulfonamide

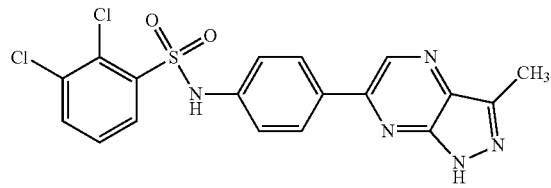 [SMILES: Cc1n[nH]c2nc(-c3ccc(NS(=O)(=O)c4cccc(Cl)c4Cl)cc3)cnc12]

(i) 1-(3,5-Dichloro-pyrazin-2-yl)-ethanol 3,5-Dichloro-pyrazine-2-carbaldehyde (5.0 g) was dissolved in dry tetrahydrofuran (100 ml) in a reaction vessel equipped with a magnetic stirring bar under an argon atmosphere. The solution was cooled on an ice-bath before slow addition of 10.3 ml methylmagnesium bromide solution (3M in tetrahydrofuran), keeping the internal temperature in the reaction vessel below 5° C. After the addition the cooling bath was removed and the reaction mixture stirred for another 10 min. Then the reaction mixture was quenched with a saturated aqueous sodium bicarbonate solution (100 ml) and extracted with EtOAc (3×200 ml). The combined aqueous phases were dried over sodium sulfate, filtered and evaporated to afford 1-(3,5-dichloro-pyrazin-2-yl)-ethanol as a dark brown oil. Yield: 5.23 g (96%).

(ii) 1-(3,5-Dichloro-pyrazin-2-yl)-ethanone 5 g of 1-(3,5-dichloro-pyrazin-2-yl)-ethanol obtained in step (i) were dissolved in dry DCM (100 ml) at RT in a reaction vessel containing a magnetic stirring bar and 80.7 ml Dess-Martin periodinane (1,1,1-tris(acetyloxy)-1,1-dihydro-1,2-benziodoxol-3-(1H)-one) solution (15% in DCM), and the mixture stirred for 30 min before the reaction was quenched with a saturated aqueous sodium bicarbonate solution (100 ml) and extracted with EtOAc (3×200 ml). The combined organic phases were dried over sodium sulfate, filtered and evaporated to afford the crude product as a brown oil. Purification by flash chromatography on silica gel using a mixture of EtOAc and heptane as the eluent afforded 1-(3,5-dichloro-pyrazin-2-yl)-ethanone as a colorless oil after evaporation of the solvents under reduced pressure. Yield: 1.9 g (38%).

(iii) N-[4-(5-Acetyl-6-chloro-pyrazin-2-yl)-phenyl]-2,3-dichloro-benzenesulfonamide 1-(3,5-Dichloro-pyrazin-2-yl)-ethanone (200 mg) and 2,3-dichloro-N-[4-(4,4,5,5-tetramethyl-[1,3,2]dioxaborolan-2-yl)-phenyl]-benzenesulfonamide (448.3 mg), prepared as in example 1, was added to a reaction vessel containing a magnetic stirring bar together with 1,1'-bis(diphenylphosphino) ferrocene-palladium(II)dichloride (61 mg) and cesium carbonate (1.0 g), followed by 9 ml dioxane and 1 ml water, and the mixture heated to 100° C. under stirring. After 2 h the reaction mixture was cooled to RT and quenched with a saturated aqueous sodium bicarbonate solution (30 ml) and extracted with EtOAc (3×30 ml). The combined organic phases were dried over sodium sulfate, filtered and evaporated to afford the crude product as a brown oil—Purification by flash chromatography on silica gel using a mixture of EtOAc and heptane as the eluent afforded N-[4-(5-acetyl-6-chloro-pyrazin-2-yl)-phenyl]-2,3-dichloro-benzenesulfonamide as a colorless solid after evaporation of the solvents under reduced pressure. Yield: 230 mg (48%).

(iv) 2,3-Dichloro-N-[4-(3-methyl-1H-pyrazolo[3,4-b]pyrazin-6-yl)phenyl]benzenesulfonamide N-[4-(5-acetyl-6-chloro-pyrazin-2-yl)-phenyl]-2,3-dichloro-benzenesulfonamide (230 mg) was suspended in a mixture of 2 ml iPrOH and 2 ml 35% hydrazine in water at RT and heated to 120° C. by microwave irradiation (Biotage Initiator™ apparatus) for 20 min under stirring in a sealed vessel. The reaction mixture was left to cool to RT, quenched with a saturated aqueous sodium bicarbonate solution (10 ml) and extracted with EtOAc (3×30 ml). The combined organic phases were dried over sodium sulfate, filtered and evaporated to afford the crude product. Purification by recrystallisation from an acetone-water mixture afforded the title compound as a pale yellow solid after drying under vacuum. Yield: 81.6 mg (38%).

$^1$H-NMR (DMSO-d$_6$): δ (ppm)=2.54 (s, 3H), 7.28 (d, J=8.8 Hz, 2H), 7.59 (t, J=8.0 Hz, 1H), 7.94 (dd, J=1.5, 8.1 Hz, 1H), 8.10 (d, J=8.8 Hz, 2H), 8.13 (dd, J=1.5, 8.0 Hz, 1H), 9.07 (s, 1H), 11.18 (s, 1H), 13.57 (s, 1H).

MS (ES+): m/e=434.0 (M+H), chloro pattern.

Example 11

2,5-Dichloro-N-[4-(3-methyl-1H-pyrazolo[3,4-b]pyrazin-6-yl)phenyl]benzenesulfonamide

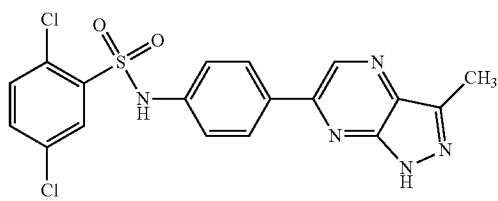 [SMILES: Cc1n[nH]c2nc(-c3ccc(NS(=O)(=O)c4cc(Cl)ccc4Cl)cc3)cnc12]

The title compound was prepared in 5% yield according to the procedure described in example 10, employing 2,5-dichloro-benzenesulfonyl chloride instead of 2,3-dichloro-benzenesulfonyl chloride as starting material. The following modification was made. The crude reaction mixture was evaporated to dryness, redissolved in DMF and purified by preparative HPLC (C18 reversed phase column, elution with a water/MeCN gradient with 0.1% TFA). The fractions containing the product were lyophilized to yield the title compound in the form of its salt with trifluoroacetic acid.

$^1$H-NMR (DMSO-d$_6$): δ (ppm)=2.55 (s, 3H), 7.29 (d, J=8.8 Hz, 2H), 7.70 (d, J=8.5 Hz, 1H), 7.76 (dd, J=2.5, 8.5 Hz, 1H), 8.09 (d, J=2.5 Hz, 1H), 8.12 (d, J=8.8 Hz, 2H), 9.08 (s, 1H), 11.17 (s, 1H), 13.57 (br, 1H).

MS (ES+): m/e=434.1 (M+H), chloro pattern.

Example 12

5-Chloro-2-fluoro-N-[4-(3-methyl-1H-pyrazolo[3,4-b]pyrazin-6-yl)phenyl]benzenesulfonamide

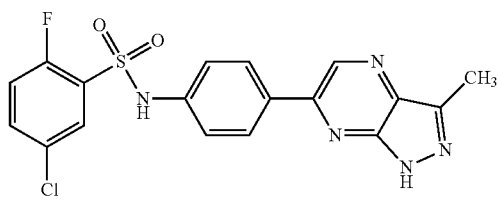 [SMILES: Cc1n[nH]c2nc(-c3ccc(NS(=O)(=O)c4cc(Cl)ccc4F)cc3)cnc12]

The title compound was prepared in 9% yield according to the procedure described in example 10, employing 5-chloro-2-fluoro-benzenesulfonyl chloride instead of 2,3-dichloro-benzenesulfonyl chloride as starting material. The following modification was made. The crude reaction mixture was evaporated to dryness, redissolved in DMF and purified by preparative HPLC (C18 reversed phase column, elution with a water/MeCN gradient with 0.1% TFA). The fractions containing the product were lyophilized to yield the title compound in the form of its salt with trifluoroacetic acid.

$^1$H-NMR (DMSO-d$_6$): δ (ppm)=2.55 (s, 3H), 7.31 (d, J=8.6 Hz, 2H), 7.53 (dd, J=8.6, 9.2 Hz, 1H), 7.80 (m, 1H), 7.89 (dd, J=2.7, 6.0 Hz, 1H), 8.14 (d, J=8.6 Hz, 2H), 9.09 (s, 1H), 11.15 (s, 1H), 13.58 (br, 1H).

MS (ES+): m/e=418.1 (M+H), chloro pattern.

Example 13

5-Chloro-2-cyano-N-[4-(3-methyl-1H-pyrazolo[3,4-b]pyrazin-6-yl)phenyl]benzenesulfonamide

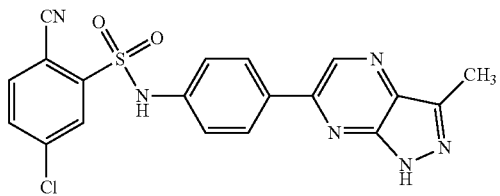

(i) [4-(5-Acetyl-6-chloro-pyrazin-2-yl)-phenyl]carbamic acid tert-butyl ester 1-(3,5-Dichloro-pyrazin-2-yl)-ethanone (2.2 g), prepared as described in example 10, and (4-tert-butoxycarbonyl-aminophenyl)boronic acid (2.7 g), was added to a reaction vessel containing a magnetic stirring bar together with 1,1'-bis(diphenylphosphino)ferrocene-palladium(II) dichloride (674 mg) and cesium carbonate (11.2 g), followed by 100 ml dioxane and 10 ml water, and the mixture heated to 100° C. under stirring. After 1 h the reaction mixture was cooled to RT and quenched with a saturated aqueous sodium bicarbonate solution (50 ml) and extracted with EtOAc (3×100 ml). The combined organic phases were dried over sodium sulfate, filtered and evaporated to afford the crude product as a dark brown oil. Purification by flash chromatography on silica gel using a mixture of EtOAc and heptane as the eluent afforded [4-(5-acetyl-6-chloro-pyrazin-2-yl)-phenyl]-carbamic acid tert-butyl ester as a colorless solid after evaporation of the solvents under reduced pressure. Yield: 2.44 g (61%) mg.

(ii) [4-(3-Methyl-1H-pyrazolo[3,4-b]pyrazin-6-yl)-phenyl]-carbamic acid tert-butyl ester

[4-(5-Acetyl-6-chloro-pyrazin-2-yl)-phenyl]-carbamic acid tert-butyl ester (2.18 g) was suspended in a mixture of 21 ml iPrOH and 21 ml 35% hydrazine in water at RT and heated to 120° C. by microwave irradiation for 20 min under stirring in a sealed vessel. The reaction mixture was left to cool to RT, quenched with a saturated aqueous sodium bicarbonate solution (10 ml) and extracted with EtOAc (3×30 ml). The combined organic phases were dried over sodium sulfate, filtered and evaporated to afford the crude product. Purification by trituration in boiling EtOAc and subsequent filtration afforded [4-(3-methyl-1H-pyrazolo[3,4-b]pyrazin-6-yl)-phenyl]-carbamic acid tert-butyl ester as a yellow solid. Yield: 1.42 g (70%).

(iii) 5-Chloro-2-cyano-N-[4(3-methyl-1H-pyrazolo[3,4-b]pyrazin-6-yl)phenyl]benzenesulfonamide To a reaction vessel containing a magnetic stirring bar and 179 mg [4-(3-methyl-1H-pyrazolo[3,4-b]pyrazin-6-yl)-phenyl]-carbamic acid tert-butyl ester was added 3 ml 4N hydrogen chloride in dioxane solution, and the mixture stirred at RT. After 2 h the reaction mixture was evaporated to dryness under reduced pressure and the residue redissolved in 3 ml pyridine, and 131 mg 5-chloro-2-cyano-benzenesulfonyl chloride was added and the mixture heated to 100° C. in a sealed vessel. After 30 min the reaction mixture was cooled and evaporated to dryness, redissolved in DMF and purified by preparative HPLC (C18 reversed phase column, elution with a water/MeCN gradient with 0.1% TFA). The fractions containing the product were lyophilized to yield the title compound in the form of its salt with trifluoroacetic acid. Yield: 24 mg (10%).

$^1$H-NMR (DMSO-$d_6$): δ (ppm)=2.55 (s, 3H), 7.31 (d, J=8.8 Hz, 2H), 7.97 (dd, J=2.2, 8.3 Hz, 1H), 8.11 (d, J=2.2 Hz, 1H), 8.14 (d, J=8.3 Hz, 1H), 8.16 (d, J=8.8 Hz, 2H), 9.10 (s, 1H), 11.25 (s, 1H), 13.58 (br, 1H).

MS (ES+): m/e=425.2 (M+H), chloro pattern.

Example 14

2-Cyano-5-methyl-N-[4-(3-methyl-1H-pyrazolo[3,4-b]pyrazin-6-yl)phenyl]benzenesulfonamide

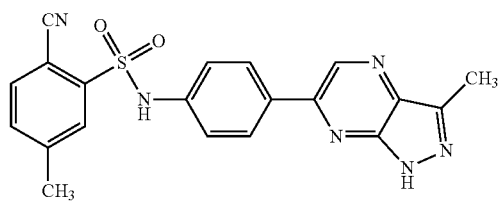 [SMILES: Cc1ccc(C#N)c(S(=O)(=O)Nc2ccc(-c3cnc4c(C)n[nH]c4n3)cc2)c1]

The title compound was prepared in 21% yield according to the procedure described in example 13, employing 2-cyano-5-methyl-benzenesulfonyl chloride instead of 5-chloro-2-cyano-benzenesulfonyl chloride as starting material.

$^1$H-NMR (DMSO-$d_6$): δ (ppm)=2.47 (s, 3H), 2.55 (s, 3H), 7.29 (d, J=8.7 Hz, 2H), 7.32 (d, J=8.6 Hz, 1H), 7.46-7.51 (m, 1H), 7.72 (dd, J=2.1, 7.1 Hz, 1H), 8.10 (d, J=8.7 Hz, 2H), 9.07 (s, 1H), 10.93 (s, 1H), 13.55 (br, 1H).

MS (ES+): m/e=405.3 (M+H).

Example 15

2-Fluoro-5-methyl-N-[4-(3-methyl-1H-pyrazolo[3,4-b]pyrazin-6-yl)phenyl]benzenesulfonamide

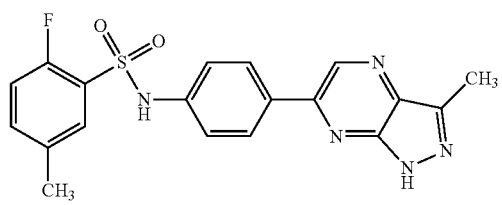 [SMILES: Cc1ccc(F)c(S(=O)(=O)Nc2ccc(-c3cnc4c(C)n[nH]c4n3)cc2)c1]

The title compound was prepared in 14% yield according to the procedure described in example 13, employing 2-fluoro-5-methyl-benzenesulfonyl chloride instead of 5-chloro-2-cyano-benzenesulfonyl chloride as starting material.

$^1$H-NMR (DMSO-$d_6$): δ (ppm)=2.34 (s, 3H), 2.55 (s, 3H), 7.31 (d, J=8.6 Hz, 2H), 7.53 (dd, J=8.6, 9.2 Hz, 1H), 7.80 (m, 1H), 7.89 (dd, J=2.7, 6.0 Hz, 1H), 8.14 (d, J=8.6 Hz, 2H), 9.09 (s, 1H), 11.15 (s, 1H), 13.58 (br, 1H).

MS (ES+): m/e=398.2 (M+H).

Example 16

2-Chloro-5-methoxy-N-[4-(3-methyl-1H-pyrazolo[3,4-b]pyrazin-6-yl)phenyl]benzenesulfonamide

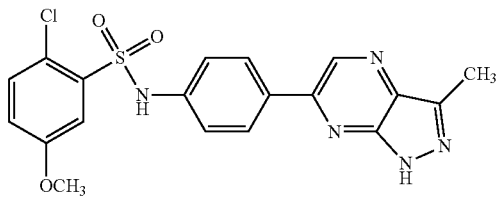 [SMILES: COc1ccc(Cl)c(S(=O)(=O)Nc2ccc(-c3cnc4c(C)n[nH]c4n3)cc2)c1]

The title compound was prepared in 14% yield according to the procedure described in example 13, employing 2-chloro-5-methoxy-benzenesulfonyl chloride instead of 5-chloro-2-cyano-benzenesulfonyl chloride as starting material.

$^1$H-NMR (DMSO-$d_6$): δ (ppm)=2.54 (s, 3H), 3.82 (s, 3H), 7.21 (dd, J=3.1, 8.7 Hz, 1H), 7.29 (d, J=8.8 Hz, 2H), 7.54 (d, J=8.7 Hz, 1H), 7.59 (d, J=3.1 Hz, 1H), 8.10 (d, J=8.8 Hz, 2H), 9.07 (s, 1H), 10.99 (s, 1H), 13.55 (br, 1H).

MS (ES+): m/e=430.2 (M+H), chloro pattern.

Example 17

N-[4-(3-Amino-1H-pyrazolo[3,4-b]pyrazin-6-yl)phenyl]-2-cyano-5-methyl-benzenesulfonamide

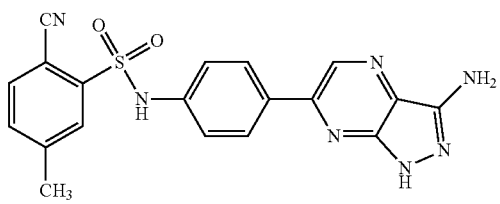 [SMILES: Cc1ccc(C#N)c(S(=O)(=O)Nc2ccc(-c3cnc4c(N)n[nH]c4n3)cc2)c1]

(i) [4-(6-Chloro-5-cyano-pyrazin-2-yl)-phenyl]carbamic acid tert-butyl ester (4-tert-Butoxycarbonyl-aminophenyl)boronic acid pinacol ester (8.26 g) was added to a reaction vessel containing a magnetic stirring bar together with 3,5-dichloro-pyrazine-2-carbonitrile (5.0 g), 1,1'-bis(diphenylphosphino)ferrocene-palladium(II) dichloride (1.68 g) and cesium carbonate (28.1 g), followed by 100 ml dioxane and 10 ml water, and the mixture heated to 100° C. under stirring. After 1 h the reaction mixture was cooled to RT and quenched with a saturated aqueous sodium bicarbonate solution (100 ml) and extracted with EtOAc (3×200 ml). The combined organic phases were dried over sodium sulfate, filtered and evaporated to afford the crude product as a brown oil which was purified by flash chromatography on silica gel using a mixture of EtOAc and heptane as the eluent. The obtained product was recrystallized from methyl tert-butyl ether to afford [4-(6-chloro-5-cyano-pyrazin-2-yl)-phenyl]-carbamic acid tert-butyl ester as a pale yellow solid after drying under vacuum. Yield: 6.92 g (73%).

(ii) [4-(3-Amino-1H-pyrazolo[3,4-b]pyrazin-6-yl)-phenyl]-carbamic acid tert-butyl ester

[4-(6-Chloro-5-cyano-pyrazin-2-yl)-phenyl]carbamic acid tert-butyl ester (1.0 g) was suspended in a mixture of 10 ml iPrOH and 10 ml 35% hydrazine in water at RT and heated to 120° C. by microwave irradiation for 70 min under stirring in a sealed vessel. The reaction mixture was left to cool to RT, and the precipitate was filtered off and washed with water to afford [4-(3-amino-1H-pyrazolo[3,4-b]pyrazin-6-yl)-phenyl]-carbamic acid tert-butyl ester as a yellow solid after drying under vacuum. Yield: 815 mg (83%).

(iii) N-[4-(3-Amino-1H-pyrazolo[3,4-b]pyrazin-6-yl)phenyl]-2-cyano-5-methyl-benzenesulfonamide To a reaction vessel containing a magnetic stirring bar and 180 mg [4-(3-amino-1H-pyrazolo[3,4-b]pyrazin-6-yl)-phenyl]-carbamic acid tert-butyl ester was added 3 ml 4N hydrogen chloride in dioxane solution and the mixture stirred at RT. After 2 h the reaction mixture was evaporated to dryness under reduced pressure and the residue redissolved in 3 ml pyridine and 131 mg 2-cyano-5-methyl-benzenesulfonyl chloride was added and the mixture heated to 100° C. in a sealed vessel. After 1 h the reaction mixture was cooled and evaporated to dryness, redissolved in DMF and purified by preparative HPLC (C18 reversed phase column, elution with a water/MeCN gradient with 0.1% TFA). The fractions containing the product were lyophilized to yield the title compound in the form or its salt with trifluoroacetic acid salt. Yield: 58 mg (20%).

MS (ES+): m/e=406.2 (M+H).

Example 18

N-[4-(3-Amino-1H-pyrazolo[3,4-b]pyrazin-6-yl)phenyl]-2-chloro-5-methoxy-benzenesulfonamide

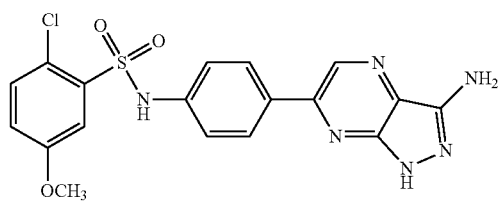 [SMILES: COc1ccc(Cl)c(S(=O)(=O)Nc2ccc(-c3cnc4c(N)n[nH]c4n3)cc2)c1]

The title compound was prepared in 22% yield according to the procedure described in example 17, employing 2-chloro-5-methoxy-benzenesulfonyl chloride instead of 2-cyano-5-methyl-benzenesulfonyl chloride as starting material.

$^1$H-NMR (DMSO-d$_6$): δ (ppm)=3.82 (s, 3H), 7.22 (dd, J=3.0, 8.7 Hz, 1H), 7.27 (d, J=8.8 Hz, 2H), 7.55 (d, J=8.7 Hz, 1H), 7.58 (d, J=3.1 Hz, 1H), 8.07 (d, J=8.8 Hz, 2H), 8.87 (s, 1H), 10.98 (s, 1H), 13.52 (br, 1H).

MS (ES+): m/e=431.1 (M+H), chloro pattern.

Example 19

N-[4-(3-Amino-1H-pyrazolo[3,4-b]pyrazin-6-yl)phenyl]-2-fluoro-5-methyl-benzenesulfonamide

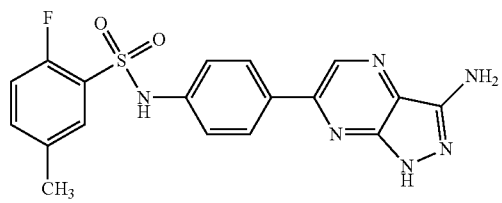 [SMILES: Cc1ccc(F)c(S(=O)(=O)Nc2ccc(-c3cnc4c(N)n[nH]c4n3)cc2)c1]

To a solution of 500 mg of 6-(4-amino-phenyl)-1H-pyrazolo[3,4-b]pyrazin-3-ylamine hydrochloride and 397 mg of 2-fluoro-5-methyl-benzenesulfonyl chloride in 4 ml DCM, 0.16 ml pyridine were added and the reaction mixture was stirred for 16 h at RT. Then, the solvents were removed under reduced pressure and the crude product was purified by chromatography on silica gel eluting with a gradient of n-heptane/EtOAc. The fractions containing the product were combined and the solvent evaporated under reduced pressure. Yield: 220 mg.

MS (ES+): m/e=399.2 (M+H).

Example 20

N-[4-(3-Amino-1H-pyrazolo[3,4-b]pyrazin-6-yl)-phenyl]-5-chloro-2-cyano-benzenesulfonamide

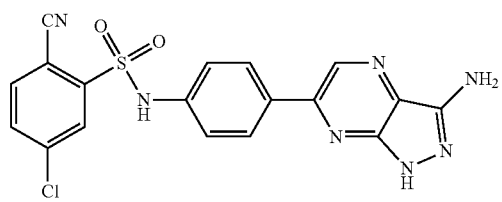

The title compound was prepared in according to the procedure described in example 17, employing 5-chloro-2-cyano-benzenesulfonyl chloride instead of 2-cyano-5-methyl-benzenesulfonyl chloride as starting material.

MS (ES+): m/e=426.1 (M+H), chloro pattern.

Example 21

N-[4-(3-Amino-1H-pyrazolo[3,4-b]pyrazin-6-yl)phenyl]-2,5-dichloro-thiophene-3-sulfonamide

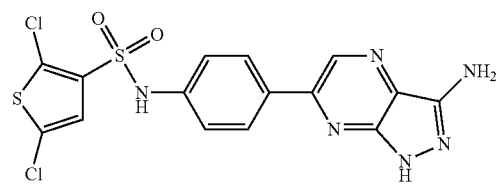 [SMILES: Nc1n[nH]c2nc(-c3ccc(NS(=O)(=O)c4cc(Cl)sc4Cl)cc3)cnc12]

The title compound was prepared by adapting the procedures described in example 19, employing 2,5-dichlorothiophene-3-sulfonyl chloride instead of 2-fluoro-5-methyl-benzenesulfonyl chloride.

$^1$H-NMR (DMSO-d$_6$): δ (ppm)=7.30 (d, J=8.8 Hz, 2H), 7.41 (s, 1H), 8.14 (d, J=8.8 Hz, 2H), 8.91 (s, 1H), 11.07 (s, 1H), 12.3 (br, 1H).

MS (ES+): m/e=441.1 (M+H), chloro pattern.

Example 22

N-[4-(3-Amino-1H-pyrazolo[3,4-b]pyrazin-6-yl)phenyl]-8-chloro-3,4-dihydro-2H-benzo[b][1,4]dioxepine-7-sulfonamide

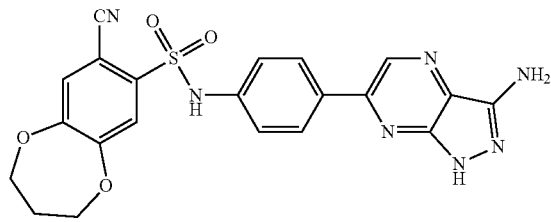 [SMILES: N#Cc1cc2c(cc1S(=O)(=O)Nc1ccc(-c3cnc4c(N)n[nH]c4n3)cc1)OCCCO2]

The title compound was prepared by adapting the procedures described in example 19, employing 8-chloro-3,4-dihydro-2H-benzo[b][1,4]dioxepine-7-sulfonyl chloride instead of 2-fluoro-5-methyl-benzenesulfonyl chloride.

$^1$H-NMR (DMSO-d$_6$): δ (ppm)=2.13 (t, J=5.6 Hz, 2H), 4.20 (t, J=5.6 Hz, 2H), 4.25 (t, J=5.6 Hz, 2H), 7.21 (s, 1H), 7.25 (d, J=8.8 Hz, 2H), 7.60 (s, 1H), 8.07 (d, J=8.8 Hz, 2H), 8.87 (s, 1H), 10.89 (s, 1H), 12.33 (br, 1H).

MS (ES+): m/e=473.2 (M+H), chloro pattern.

Example 23

N-[4-(3-Amino-1H-pyrazolo[3,4-b]pyrazin-6-yl)phenyl]-5-chloro-1,3-dimethyl-pyrazole-4-sulfonamide

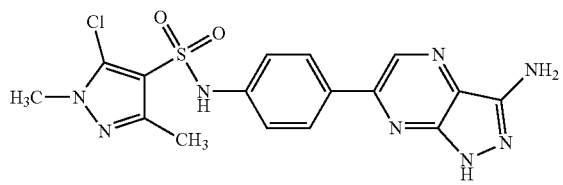 [SMILES: Cc1nn(C)c(Cl)c1S(=O)(=O)Nc1ccc(-c2cnc3c(N)n[nH]c3n2)cc1]

The title compound was prepared by adapting the procedures described in example 19, employing 5-chloro-1,3-dimethyl-pyrazole-4-sulfonyl chloride instead of 2-fluoro-5-methyl-benzenesulfonyl chloride.

$^1$H-NMR (DMSO-d$_6$): δ (ppm)=2.30 (s, 3H), 3.72 (s, 3H), 7.25 (d, J=8.8 Hz, 2H), 8.09 (d, J=8.8 Hz, 2H), 8.90 (s, 1H), 10.81 (s, 1H), 12.30 (br, 1H).

MS (ES+): m/e=419.1 (M+H), chloro pattern.

Example 24

2,3-Dichloro-N-[6-[4-[(2-fluoro-5-methyl-phenyl)sulfonylamino]phenyl]-1H-pyrazolo[3,4-b]pyrazin-3-yl]benzamide

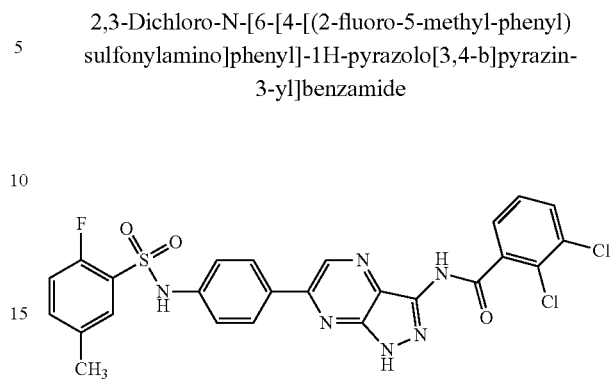

(i) N-[4-(3-Amino-1H-pyrazolo[3,4-b]pyrazin-6-yl)phenyl]-2-fluoro-5-methyl-benzenesulfonamide To a solution of 500 mg of 6-(4-amino-phenyl)-1H-pyrazolo[3,4-b]pyrazin-3-ylamine hydrochloride and 397 mg of 2-fluoro-5-methyl-benzenesulfonyl chloride in 4 ml DCM, 0.16 ml pyridine were added and the reaction mixture was stirred for 16 h at RT. Then, the solvents were removed under reduced pressure and the crude product was purified by chromatography on silica gel eluting with a gradient of n-heptane/EtOAc. The fractions containing the product were combined and the solvent evaporated under reduced pressure. Yield: 220 mg.

(ii) 2,3-Dichloro-N-[6-[4-[(2-fluoro-5-methyl-phenyl)sulfonylamino]phenyl]-1H-pyrazolo[3,4-b]pyrazin-3-yl]benzamide To a solution of 70 mg of N-[4-(3-amino-1H-pyrazolo[3,4-b]pyrazin-6-yl)phenyl]-2-fluoro-5-methyl-benzenesulfonamide in 0.5 ml pyridine, 13 mg of 2,3-dichloro-benzoyl chloride were added and the reaction mixture was stirred for 16 h at RT. Then, the reaction mixture was diluted with water and filtered through a chem Elut® cartridge by eluting with EtOAc. After removal of the solvents under reduced pressure the crude product was purified by preparative HPLC (C18 reversed phase column, elution with a water/MeCN gradient with 0.1% TFA). The fractions containing the product were lyophilized to yield the title compound in the form of its salt with trifluoroacetic acid. Yield: 5 mg.

$^1$H-NMR (DMSO-d$_6$): δ (ppm)=2.33 (s, 3H), 7.29 (d, J=8.8 Hz, 2H), 7.32 (m, 1H), 7.48 (m, 1H), 7.62 (d, J=8.8 Hz, 1H), 7.73 (m, 1H), 7.80 (d, J=8.8 Hz, 1H), 7.98 (d, J=8.8 Hz, 2H), 9.29 (s, 1H), 10.95 (s, 1H), 12.40 (br, 1H).

MS (ES+): m/e=571.3 (M+H), chloro pattern.

Example 25

N-[6-[4-[(2-Fluoro-5-methyl-phenyl)sulfonylamino]phenyl]-1H-pyrazolo[3,4-b]pyrazin-3-yl]tetrahydropyran-4-carboxamide

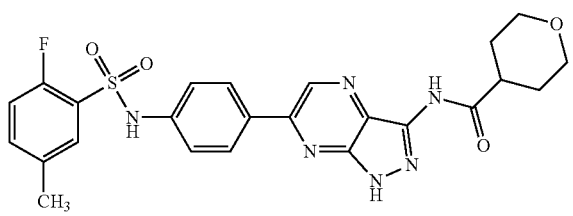 [SMILES: Cc1ccc(F)c(S(=O)(=O)Nc2ccc(-c3cnc4c(NC(=O)C5CCOCC5)n[nH]c4n3)cc2)c1]

The title compound was prepared by adapting the procedures described in example 24, employing tetrahydropyran-4-carbonyl chloride instead of 2,3-dichloro-benzoyl chloride.
MS (ES+): m/e=511.2 (M+H).

Example 26

N-[6-[4-[(2-Fluoro-5-methyl-phenyl)sulfonylamino]phenyl]-1H-pyrazolo[3,4-b]pyrazin-3-yl]piperidine-4-carboxamide

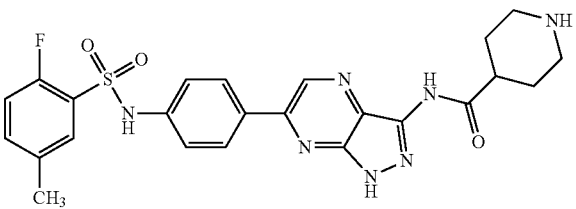 [SMILES: Cc1ccc(F)c(S(=O)(=O)Nc2ccc(-c3cnc4c(NC(=O)C5CCNCC5)n[nH]c4n3)cc2)c1]

The title compound was prepared by adapting the procedures described in example 24, employing piperidine-4-carbonyl chloride instead of 2,3-dichloro-benzoyl chloride.
MS (ES+): m/e=510.3 (M+H).

Example 27

N-[6-[4-[(2-Fluoro-5-methyl-phenyl)sulfonylamino]phenyl]-1H-pyrazolo[3,4-b]pyrazin-3-yl]cyclopentanecarboxamide

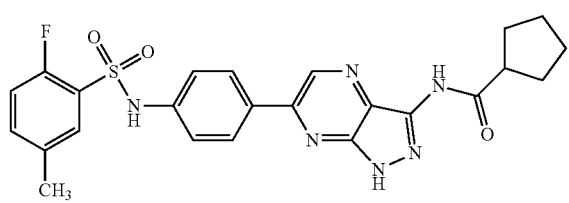 [SMILES: Cc1ccc(F)c(S(=O)(=O)Nc2ccc(-c3cnc4c(NC(=O)C5CCCC5)n[nH]c4n3)cc2)c1]

The title compound was prepared by adapting the procedures described in example 24, employing cyclopentanecarbonyl chloride instead of 2,3-dichloro-benzoyl chloride.
MS (ES−): m/e=493.4 (M−H).

Example 28

N-[6-[4-[(2-Fluoro-5-methyl-phenyl)sulfonylamino]phenyl]-1H-pyrazolo[3,4-b]pyrazin-3-yl]cyclopropanecarboxamide

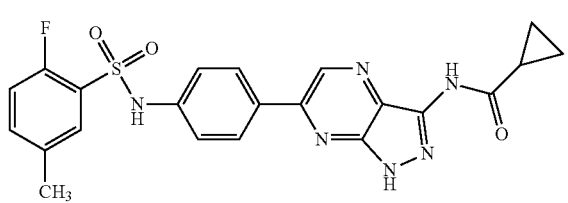 [SMILES: Cc1ccc(F)c(S(=O)(=O)Nc2ccc(-c3cnc4c(NC(=O)C5CC5)n[nH]c4n3)cc2)c1]

The title compound was prepared by adapting the procedures described in example 24, employing cyclopropanecarbonyl chloride instead of 2,3-dichloro-benzoyl chloride.
MS (ES+): m/e=467.3 (M+H).

Example 29

N-[6-[4-[(2-Fluoro-5-methyl-phenyl)sulfonylamino]phenyl]-1H-pyrazolo[3,4-b]pyrazin-3-yl]cyclohexanecarboxamide

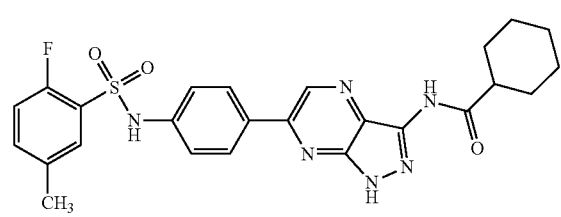

The title compound was prepared by adapting the procedures described in example 24, employing cyclohexanecarbonyl chloride instead of 2,3-dichloro-benzoyl chloride.
MS (ES+): m/e=509.4 (M+H).

Example 30

N-[6-[4-[(2-Fluoro-5-methyl-phenyl)sulfonylamino]phenyl]-1H-pyrazolo[3,4-b]pyrazin-3-yl]-2-phenyl-acetamide

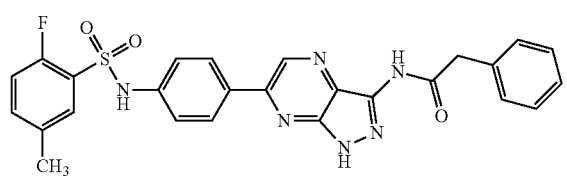 [SMILES: Cc1ccc(F)c(S(=O)(=O)Nc2ccc(-c3cnc4c(NC(=O)Cc5ccccc5)n[nH]c4n3)cc2)c1]

The title compound was prepared by adapting the procedures described in example 24, employing 2-phenylacetyl chloride instead of 2,3-dichloro-benzoyl chloride.
MS (ES+): m/e=517.4 (M+H).

Example 31

N-[6-[4-[(2-Fluoro-5-methyl-phenyl)sulfonylamino]phenyl]-1H-pyrazolo[3,4-b]pyrazin-3-yl]thiophene-3-carboxamide

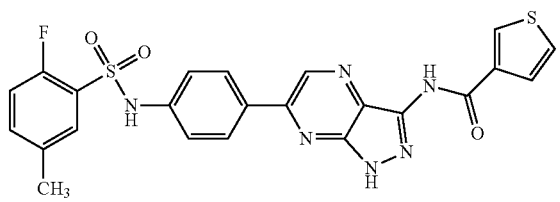 [SMILES: Cc1ccc(F)c(S(=O)(=O)Nc2ccc(-c3cnc4c(NC(=O)c5ccsc5)n[nH]c4n3)cc2)c1]

The title compound was prepared by adapting the procedures described in example 24, employing thiophene-3-carbonyl chloride instead of 2,3-dichloro-benzoyl chloride.
MS (ES+): m/e=509.3 (M+H).

Example 32

4-Chloro-N-[6-[4-[(2-fluoro-5-methyl-phenyl)sulfonylamino]phenyl]-1H-pyrazolo[3,4-b]pyrazin-3-yl]benzamide

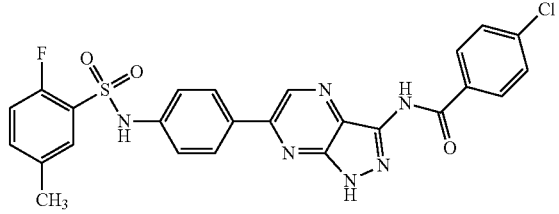 [SMILES: Cc1ccc(F)c(S(=O)(=O)Nc2ccc(-c3cnc4c(NC(=O)c5ccc(Cl)cc5)n[nH]c4n3)cc2)c1]

The title compound was prepared by adapting the procedures described in example 24, employing 4-chloro-benzoyl chloride instead of 2,3-dichloro-benzoyl chloride.
MS (ES+): m/e=537.3 (M+H), chloro pattern.

Example 33

N-[4-(3-Amino-1H-pyrazolo[3,4-b]pyrazin-6-yl)phenyl]naphthalene-1-sulfonamide

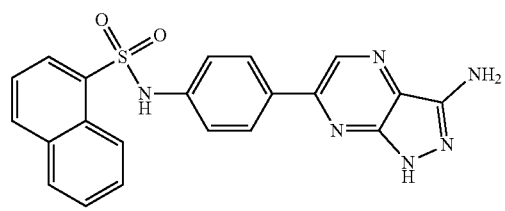 [SMILES: Nc1n[nH]c2nc(-c3ccc(NS(=O)(=O)c4cccc5ccccc45)cc3)cnc12]

The title compound was prepared by adapting the procedures described in example 19, employing naphthalene-1-sulfonyl chloride instead of 2-fluoro-5-methyl-benzenesulfonyl chloride.
MS (ES+): m/e=417.2 (M+H).

Example 34

N-[4-(3-Amino-1H-pyrazolo[3,4-b]pyrazin-6-yl)phenyl]-2,4,6-trichloro-benzenesulfonamide

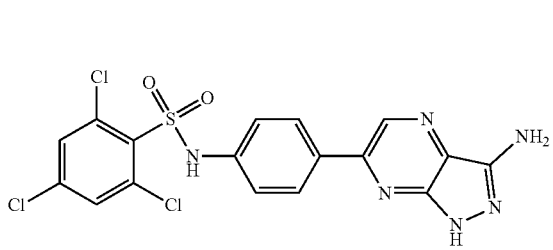 [SMILES: Nc1n[nH]c2nc(-c3ccc(NS(=O)(=O)c4c(Cl)cc(Cl)cc4Cl)cc3)cnc12]

The title compound was prepared by adapting the procedures described in example 19, employing 2,4,6-trichlorobenzenesulfonamide instead of 2-fluoro-5-methyl-benzenesulfonyl chloride.
MS (ES+): m/e=470.1 (M+H), chloro pattern.

Example 35

N-[4-(3-Amino-1H-pyrazolo[3,4-b]pyrazin-6-yl)phenyl]-5-chloro-2-fluoro-benzenesulfonamide

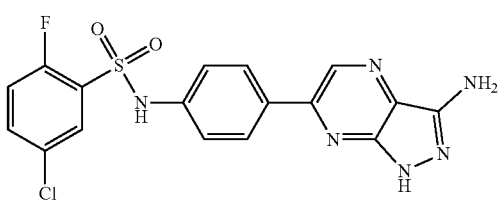 [SMILES: Nc1n[nH]c2nc(-c3ccc(NS(=O)(=O)c4cc(Cl)ccc4F)cc3)cnc12]

The title compound was prepared by adapting the procedures described in example 1, employing 5-chloro-2-fluoro-benzenesulfonyl chloride instead of 2,3-dichloro-benzenesulfonyl chloride as starting material. The following modification was made. The crude reaction mixture was evaporated to dryness, redissolved in DMF and purified by preparative HPLC (C18 reversed phase column, elution with a water/MeCN gradient with 0.1% TFA). The fractions containing the product were lyophilized to yield the title compound in the form of its salt with trifluoroacetic acid.
$^1$H-NMR (DMSO-$d_6$): δ (ppm)=7.27 (d, J=8.8 Hz, 2H), 7.55 (t, J=8.7 Hz, 1H), 7.81 (m, 1H), 7.88 (m, 1H), 8.10 (d, J=8.8 Hz, 2H), 8.91 (s, 1H), 11.10 (s, 1H).
MS (ES+): m/e=419.0 (M+H), chloro pattern.

Example 36

N-[4-(3-Amino-1H-pyrazolo[3,4-b]pyrazin-6-yl)phenyl]-2-chloro-4-trifluoromethyl-benzenesulfonamide

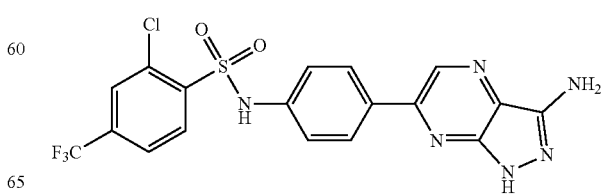

The title compound was prepared by adapting the procedures described in example 19, employing 2-chloro-4-trifluoromethyl-benzenesulfonyl chloride instead of 2-fluoro-5-methyl-benzenesulfonyl chloride.

MS (ES+): m/e=469.2 (M+H), chloro pattern.

Example 37

N-[4-(3-Amino-1H-pyrazolo[3,4-b]pyrazin-6-yl)phenyl]-2,4,5-trifluoro-benzenesulfonamide

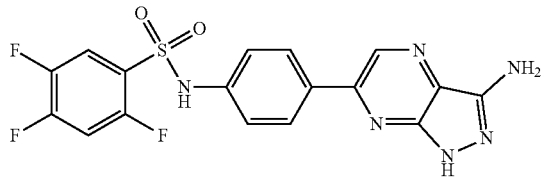 [SMILES: Nc1n[nH]c2nc(-c3ccc(NS(=O)(=O)c4cc(F)c(F)cc4F)cc3)cnc12]

The title compound was prepared by adapting the procedures described in example 19, employing 2,4,5-trifluoro-benzenesulfonyl chloride instead of 2-fluoro-5-methyl-benzenesulfonyl chloride.

MS (ES+): m/e=421.1 (M+H).

Example 38

N-[4-(3-Amino-1H-pyrazolo[3,4-b]pyrazin-6-yl)phenyl]-2,4,5-trichloro-benzenesulfonamide

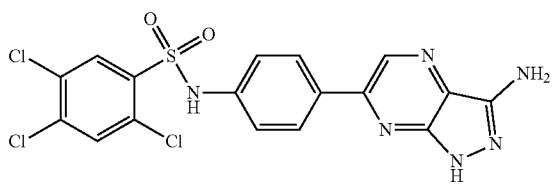 [SMILES: Nc1n[nH]c2nc(-c3ccc(NS(=O)(=O)c4cc(Cl)c(Cl)cc4Cl)cc3)cnc12]

The title compound was prepared by adapting the procedures described in example 19, employing 2,4,5-trichloro-benzenesulfonyl chloride instead of 2-fluoro-5-methyl-benzenesulfonyl chloride.

$^1$H-NMR (DMSO-$d_6$): δ (ppm)=7.28 (d, J=8.6 Hz, 2H), 8.09 (d, J=8.6 Hz, 2H), 8.24 (s, 1H), 8.87 (s, 1H), 11.18 (s, 1H), 12.30 (br, 1H).

MS (ES+): m/e=469.0 (M+H), chloro pattern.

Example 39

N-[4-(3-Amino-1H-pyrazolo[3,4-b]pyrazin-6-yl)phenyl]-5-chloro-2,4-difluoro-benzenesulfonamide

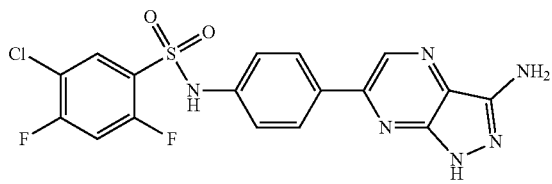 [SMILES: Nc1n[nH]c2nc(-c3ccc(NS(=O)(=O)c4cc(Cl)c(F)cc4F)cc3)cnc12]

The title compound was prepared by adapting the procedures described in example 19, employing 5-chloro-2,4-difluoro-benzenesulfonyl chloride instead of 2-fluoro-5-methyl-benzenesulfonyl chloride.

$^1$H-NMR (DMSO-$d_6$): δ (ppm)=7.29 (d, J=8.6 Hz, 2H), 7.84 (t, J=9.4 Hz, 1H), 8.10 (d, J=8.8 Hz, 2H), 8.90 (s, 1H), 11.14 (s, 1H), 12.30 (br, 1H).

MS (ES+): m/e=437.1 (M+H), chloro pattern.

Example 40

N-[4-(3-Amino-1H-pyrazolo[3,4-b]pyrazin-6-yl)phenyl]-2,3,4-trichloro-benzenesulfonamide)

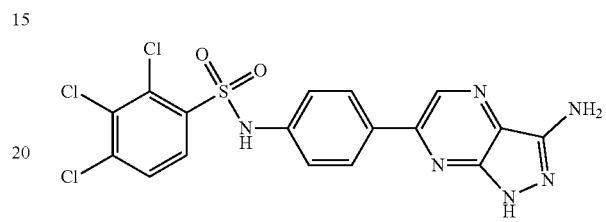

The title compound was prepared by adapting the procedures described in example 19, employing 2,3,4-trichloro-benzenesulfonyl chloride instead of 2-fluoro-5-methyl-benzenesulfonyl chloride.

MS (ES+): m/e=470.9 (M+H), chloro pattern.

Example 41

N-[4-(3-Amino-1H-pyrazolo[3,4-b]pyrazin-6-yl)phenyl]-2,3,4-trifluoro-benzenesulfonamide

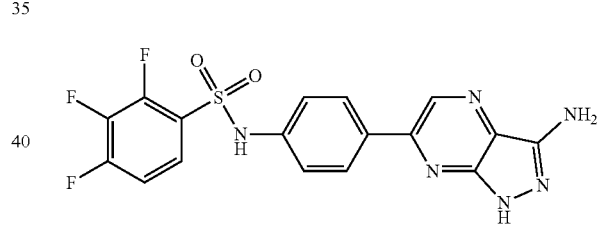

The title compound was prepared by adapting the procedures described in example 19, employing 2,3,4-trifluoro-benzenesulfonyl chloride instead of 2-fluoro-5-methyl-benzenesulfonyl chloride.

MS (ES+): m/e=421.2 (M+H).

Example 42

5-Chloro-N-[4-[3-[(5-chloro-2,4-difluoro-phenyl)sulfonylamino]-1H-pyrazolo[3,4-b]pyrazin-6-yl]phenyl]-2,4-difluoro-benzenesulfonamide

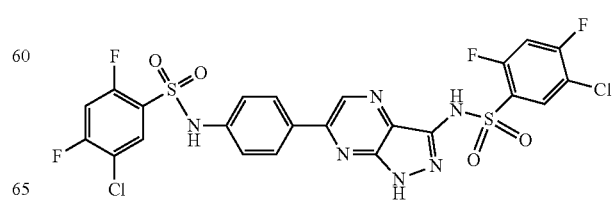

The title product was isolated as a by-product in the synthesis of N-[4-(3-amino-1H-pyrazolo[3,4-b]pyrazin-6-yl)-phenyl]-5-chloro-2,4-difluoro-benzenesulfonamide.
MS (ES+): m/e=647.1 (M+H), chloro pattern.

Example 43

5-Chloro-N-[4-[3-[(5-chloro-1,3-dimethyl-pyrazol-4-yl)sulfonylamino]-1H-pyrazolo[3,4-b]pyrazin-6-yl]phenyl]-1,3-dimethyl-pyrazole-4-sulfonamide

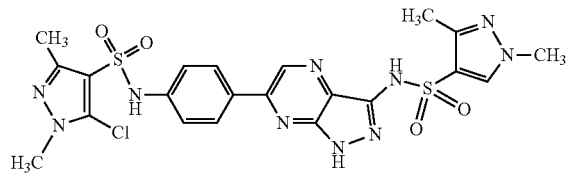

The title product was isolated as a by-product in the synthesis of 5-chloro-1,3-dimethyl-1H-pyrazole-4-sulfonic acid [4-(3-amino-1H-pyrazolo[3,4-b]pyrazin-6-yl)-phenyl]-amide.
MS (ES+): m/e=611.1 (M+H), chloro pattern.

Example 44

2,4,5-Trifluoro-N-[4-[3-[(2,4,5-trifluorophenyl)sulfonylamino]-1H-pyrazolo[3,4-b]pyrazin-6-yl]phenyl]benzenesulfonamide

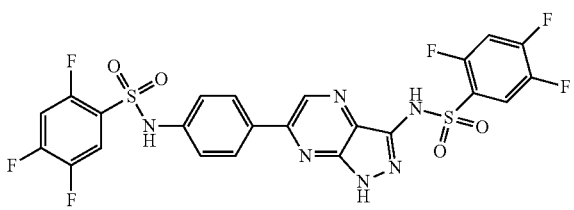 [SMILES: O=S(=O)(Nc1ccc(-c2cnc3c(NS(=O)(=O)c4cc(F)c(F)cc4F)n[nH]c3n2)cc1)c1cc(F)c(F)cc1F]

The title product was isolated as a by-product in the synthesis of N-[4-(3-amino-1H-pyrazolo[3,4-b]pyrazin-6-yl)-phenyl]-2,4,5-trifluoro-benzenesulfonamide.
MS (ES+): m/e=615.1 (M+H).

Example 45

N-[4-(3-Amino-1H-pyrazolo[3,4-b]pyrazin-6-yl)-phenyl]-5-cyano-2-fluoro-benzenesulfonamide

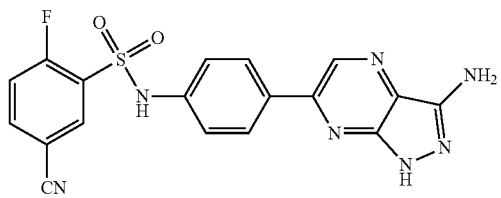 [SMILES: N#Cc1ccc(F)c(S(=O)(=O)Nc2ccc(-c3cnc4c(N)n[nH]c4n3)cc2)c1]

The title compound was prepared in 11% yield according to the procedure described in example 17, employing 5-cyano-2-fluoro-benzenesulfonyl chloride instead of 2-cyano-5-methyl-benzenesulfonyl chloride as starting material.
$^1$H-NMR (DMSO-d$_6$): δ (ppm)=5.70 (br s, 3H), 7.29 (d, J=8.7 Hz, 2H), 7.71 (m, 1H), 8.07 (d, J=8.7 Hz, 2H), 8.25 (m, 1H), 8.40 (dd, J=1.9, 6.5 Hz, 1H), 8.88 (s, 1H), 11.22 (s, 1H), 12.32 (s, 1H).
MS (ES+): m/e=410.2 (M+H).

Example 46

N-[4-(3-Amino-1H-pyrazolo[3,4-b]pyrazin-6-yl)-phenyl]-2-cyano-5-methoxy-benzenesulfonamide

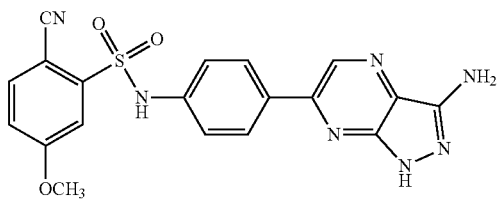

The title compound was prepared in 15% yield according to the procedure described in example 17, employing 2-cyano-5-methoxy-benzenesulfonyl chloride instead of 2-cyano-5-methyl-benzenesulfonyl chloride as starting material.
$^1$H-NMR (DMSO-d$_6$): δ (ppm)=3.89 (s, 3H), 5.70 (br s, 3H), 7.29 (d, J=8.8 Hz, 2H), 7.36 (dd, J=2.5, 8.6 Hz, 1H), 7.54 (d, J=2.5 Hz, 1H), 8.02 (d, J=8.6 Hz, 1H), 8.10 (d, J=8.8 Hz, 2H), 8.88 (s, 1H), 11.13 (s, 1H), 12.32 (s, 1H).
MS (ES+): m/e=422.3 (M+H).

Example 47

N-[4-(3-Amino-1H-pyrazolo[3,4-b]pyrazin-6-yl)-phenyl]-2-cyano-5-fluoro-benzenesulfonamide

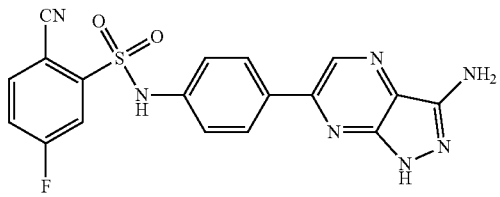 [SMILES: N#Cc1ccc(F)cc1S(=O)(=O)Nc1ccc(-c2cnc3c(N)n[nH]c3n2)cc1]

The title compound was prepared in 15% yield according to the procedure described in example 17, employing 2-cyano-5-fluoro-benzenesulfonyl chloride instead of 2-cyano-5-methyl-benzenesulfonyl chloride as starting material.
$^1$H-NMR (DMSO-d$_6$): δ (ppm)=5.71 (br s, 3H), 7.29 (d, J=8.7 Hz, 2H), 7.76 (m, 1H), 7.96 (dd, J=2.6, 8.2 Hz, 1H), 8.11 (d, J=8.7 Hz, 2H), 8.22 (dd, J=5.1, 8.6 Hz, 1H), 8.89 (s, 1H), 11.27 (s, 1H), 12.33 (s, 1H).
MS (ES+): m/e=410.2 (M+H).

Example 48

N-[4-(3-Amino-1H-pyrazolo[3,4-b]pyrazin-6-yl)-phenyl]-2-fluoro-5-methoxy-benzenesulfonamide

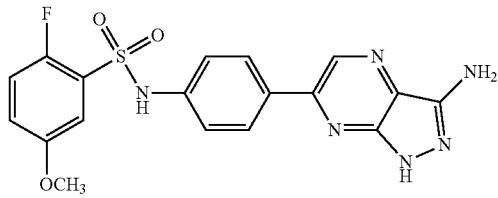

The title compound was prepared in 11% yield according to the procedure described in example 17, employing 2-fluoro-5-methoxy-benzenesulfonyl chloride instead of 2-cyano-5-methyl-benzenesulfonyl chloride as starting material.

$^1$H-NMR (DMSO-$d_6$): δ (ppm)=3.79 (s, 3H), 5.68 (br s, 3H), 7.21-7.26 (m, 1H), 7.28 (d, J=8.7 Hz, 2H), 7.32-7.39 (m, 2H), 8.06 (d, J=8.7 Hz, 2H), 8.87 (s, 1H), 10.97 (s, 1H), 12.30 (s, 1H).

MS (ES+): m/e=415.2 (M+H).

Example 49

1-[6-[4-[(2-Fluoro-5-methyl-phenyl)sulfonylamino]phenyl]-1H-pyrazolo[3,4-b]pyrazin-3-yl]-3-(3-pyridyl)-urea

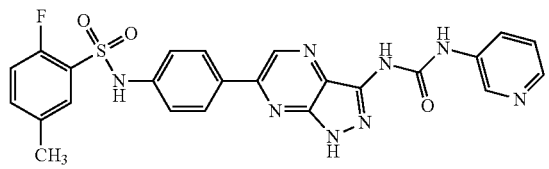

To a solution of 25 mg of N-[4-(3-amino-1H-pyrazolo[3,4-b]pyrazin-6-yl)phenyl]-2-fluoro-5-methyl-benzenesulfonamide in 0.5 ml dioxane, 9 mg of 3-isocyanato-pyridine and 7 mg 1,3-dimethylimidazolidin-2-one were added and the reaction mixture was stirred for 16 h at RT. Then the reaction mixture was concentrated under reduced pressure and the crude product was purified by preparative HPLC (C18 reversed phase column, elution with a water/MeCN gradient with 0.1% TFA). The fractions containing the product were lyophilized to yield the title compound in the form of its salt with trifluoroacetic acid. Yield: 2 mg.

MS (ES+): m/e=519.3 (M+H).

Example 50

1-(4-Chlorophenyl)-3-[6-[4-[(2-fluoro-5-methyl-phenyl)sulfonylamino]phenyl]-1H-pyrazolo[3,4-b]pyrazin-3-yl]-urea

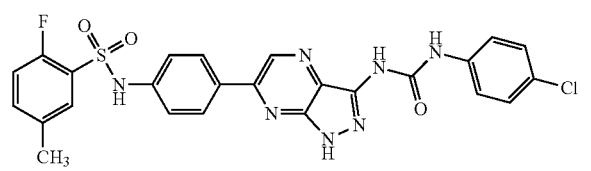 [SMILES: Cc1ccc(F)c(S(=O)(=O)Nc2ccc(-c3cnc4c(NC(=O)Nc5ccc(Cl)cc5)n[nH]c4n3)cc2)c1]

The title compound was prepared by adapting the procedures described in example 49, employing 1-chloro-4-isocyanato-benzene instead of 3-isocyanato-pyridine.

MS (ES+): m/e=552.2 (M+H), chloro pattern.

Example 51

2-Chloro-N-[4-[3-[[2-chloro-4-trifluoromethyl-phenyl]sulfonylamino]-1H-pyrazolo[3,4-b]pyrazin-6-yl]phenyl]-4-trifluoromethyl-benzenesulfonamide

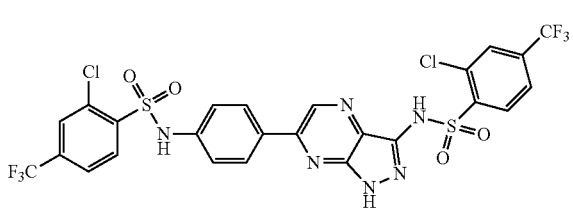 [SMILES: O=S(=O)(Nc1ccc(-c2cnc3c(NS(=O)(=O)c4ccc(C(F)(F)F)cc4Cl)n[nH]c3n2)cc1)c1ccc(C(F)(F)F)cc1Cl]

The title product was isolated as a by-product in the synthesis of N-[4-(3-amino-1H-pyrazolo[3,4-b]pyrazin-6-yl)phenyl]-2-chloro-4-trifluoromethyl-benzenesulfonamide.

MS (ES+): m/e=711.1 (M+H), chloro pattern.

Example 52

N-[6-[4-(1-Naphthylsulfonylamino)phenyl]-1H-pyrazolo[3,4-b]pyrazin-3-yl]naphthalene-1-sulfonamide

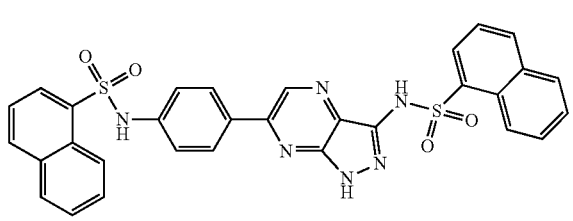 [SMILES: O=S(=O)(Nc1ccc(-c2cnc3c(NS(=O)(=O)c4cccc5ccccc45)n[nH]c3n2)cc1)c1cccc2ccccc12]

The title product was isolated as a by-product in the synthesis of N-[4-(3-amino-1 H-pyrazolo[3,4-b]pyrazin-6-yl)phenyl]naphthalene-1-sulfonamide.

MS (ES+): m/e=607.3 (M+H).

Example 53

2,4,6-Trichloro-N-[4-[3-[(2,4,6-trichlorophenyl)sulfonylamino]-1H-pyrazolo[3,4-b]pyrazin-6-yl]phenyl]benzenesulfonamide

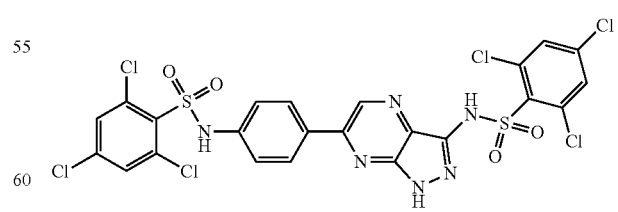

The title product was isolated as a by-product in the synthesis of N-[4-(3-amino-1H-pyrazolo[3,4-b]pyrazin-6-yl)phenyl]-2,4,6-trichloro-benzenesulfonamide.

MS (ES+): m/e=710.1 (M+H), chloro pattern.

Example 54

N-[3-Methyl-4-[[4-(3-methyl-1H-pyrazolo[3,4-b]pyrazin-6-yl)phenyl]sulfamoyl]phenyl]acetamide

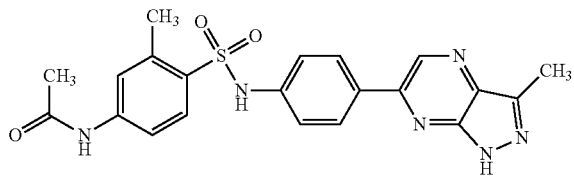 [SMILES: CC(=O)Nc1ccc(S(=O)(=O)Nc2ccc(-c3cnc4c(C)n[nH]c4n3)cc2)c(C)c1]

The title compound was prepared in 1% yield according to the procedure described in example 10, employing 4-acetylamino-2-methyl-benzenesulfonyl chloride instead of 2,3-dichloro-benzenesulfonyl chloride as starting material. The following modification was made. The crude reaction mixture was evaporated to dryness, redissolved in DMF and purified by preparative HPLC (C18 reversed phase column, elution with a water/MeCN gradient with 0.1% TFA). The fractions containing the product were lyophilized to yield the title compound in the form of its salt with trifluoroacetic acid.

MS (ES+): m/e=437.2 (M+H).

Example 55

2-Methyl-N-[4-(3-methyl-1H-pyrazolo[3,4-b]pyrazin-6-yl)phenyl]-5-nitro-benzenesulfonamide

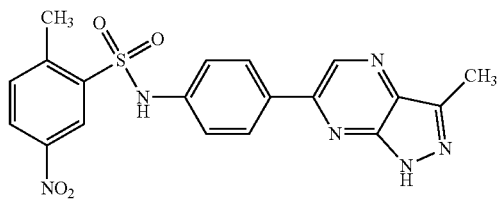

The title compound was prepared in 18% yield according to the procedure described in example 10, employing 2-methyl-5-nitro-benzenesulfonyl chloride instead of 2,3-dichloro-benzenesulfonyl chloride as starting material. The following modification as made. The crude reaction mixture was evaporated to dryness, redissolved in DMF and purified by preparative HPLC (C18 reversed phase column, elution with a water/MeCN gradient with 0.1% TFA). The fractions containing the product were lyophilized to yield the title compound in the form of its salt with trifluoroacetic acid.

MS (ES+): m/e=425.2 (M+H).

Example 56

N-[4-(3-Methyl-1H-pyrazolo[3,4-b]pyrazin-6-yl)phenyl]-2-nitro-4-trifluoromethyl-benzenesulfonamide

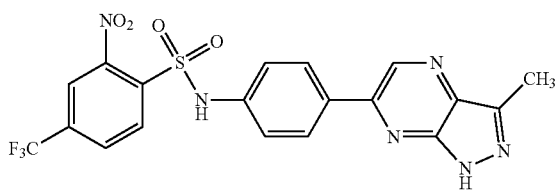 [SMILES: Cc1n[nH]c2nc(-c3ccc(NS(=O)(=O)c4ccc(C(F)(F)F)cc4[N+](=O)[O-])cc3)cnc12]

The title compound was prepared in 5% yield according to the procedure described in example 10, employing 2-nitro-4-trifluoromethyl-benzenesulfonyl chloride instead of 2,3-dichloro-benzenesulfonyl chloride as starting material. The following modification was made. The crude reaction mixture was evaporated to dryness, redissolved in DMF and purified by preparative HPLC (C18 reversed phase column, elution with a water/MeCN gradient with 0.1% TFA). The fractions containing the product were lyophilized to yield the title compound in the form of its salt with trifluoroacetic acid.

MS (ES+): m/e=479.1 (M+H).

Pharmacological Testing

The ability of the compounds of the invention to inhibit SGK-1 was assessed in an enzymatic activity assay by determining their effect on the ability of the isolated SGK enzyme to catalyze the transfer of phosphate from ATP to serine/threonine residues in a labeled substrate peptide, and in cellular assays by determining their effect on cellular function. In one of the cellular assays, the SGK-1 dependent phosphorylation of glycogen synthase kinase 3beta (GSK3beta) in U2OS cells was measured, in another one, a functional electrophysiological assay, the SGK-1 dependent activation of epithelial $Na^+$ channel (ENaC) currents in A6 cell monolayers, and in another one chondrocyte hypertrophic differentiation in mouse chondrogenic ATDC5 cells.

A) Enzymatic Activity Assay

The compounds were tested for serum and glucocorticoid-regulated kinase 1 (SGK-1) inhibitory activity in a substrate phosphorylation assay designed to measure the ability of the isolated enzyme to catalyze the transfer of phosphate from ATP to serine/threonine residues in a fluorescein-labeled substrate peptide, using recombinant human SGK-1 enzyme produced in a baculovirus system (Biomol, Hamburg, Germany, Cat. No. 4-331). The synthesized fluorescent labeled peptide substrate contained (5(6)-Carboxyfluorescein)-RPRAATF-$NH_2$. The phosphorylated substrate peptide and non-phosphorylated substrate peptide were separated with caliper life science's lab-chip technology based on a micro fluidics method. All fluid flow was established on the chip by applying a vacuum of a few psi to the waste well transporting fluid from various sources through interconnecting channels. Because the phosphoryl group is doubly negatively charged, under the pressure-driven hydrodynamic flow and the voltage-driven flow within the electric field, the fluorescent labeled peptide substrate and its phosphorylation product appear at different times in the detection window to the detection point. Substrate turnover can thus be determined as the ratio of the product peak area and the sum of substrate peak area and product peak area.

The enzyme reaction was carried out in a buffer containing 25 mM Tris-HCl (pH 7.4), 5 mM $MgCl_2$, 2 mM $MnCl_2$, 2 mM DTT, and 0.03% bovine serum albumine. The enzyme was pre-incubated with the test compound for 30 min at 24° C. The kinase reaction was initiated by addition of the substrate mixture containing the peptide substrate (final concentration 1 µM) and ATP (final concentration 10 µM). After 60 min incubation at 37° C., the enzyme reaction was terminated by adding a buffer containing 100 mM Hepes (pH 7.4) and 35 mM EDTA.

For the determination of the compound dose response, a 10 mM DMSO stock solution was diluted and tested in a ten-point, three-fold dilution series run in duplicate beginning at 30 µM final concentration. Data were analyzed using a four-parameter curve fit with a fixed minimum and maximum experimentally defined as the average positive and negative controls on each plate. $IC_{50}$ values (in µM (micromol/liter)) for inhibition of SGK-1 determined in this assay are given in Table 1.

TABLE 1

IC$_{50}$ values for inhibition of SGK-1 enzymatic activity by example compounds

| Example no. | IC$_{50}$ [μM] |
|---|---|
| 1 | 0.003 |
| 2 | 0.439 |
| 3 | 0.496 |
| 4 | 0.419 |
| 5 | 0.005 |
| 6 | 0.002 |
| 7 | 0.002 |
| 8 | 0.196 |
| 9 | 0.003 |
| 10 | 0.013 |
| 11 | 0.002 |
| 12 | 0.004 |
| 13 | 0.003 |
| 14 | 0.003 |
| 15 | 0.002 |
| 16 | 0.002 |
| 35 | 0.001 |
| 42 | 0.413 |
| 43 | 1.050 |
| 45 | 0.047 |
| 46 | 0.002 |

B) Determination of the Effect on SGK-1 Dependent Phosphorylation of GSK3beta in U2OS Cells It has been shown that glycogen synthase kinase 3beta (GSK3beta) is a phosphorylation target of SGK-1 (Sakoda, H., Gotoh, Y., Katagiri, H., Kurokawa, M., Ono, H., Onishi, Y., Anai, M., Ogihara, T., Fujishiro, M., Fukushima, Y., Abe, M., Shojima, N., Kikuchi, M., Oka, Y., Hirai, H., Asano, T.; Differing roles of Akt and serum- and glucocorticoid-regulated kinase in glucose metabolism, DNA synthesis, and oncogenic activity. J. Biol. Chem. 278 (2003), 25802-25807). The ability of the compounds of the invention to inhibit the enzymatic activity of serum and glucocorticoid-regulated Kinase 1 (SGK-1) was determined in a cellular assay which measures the SGK-1 dependent phosphorylation of GSK3beta in U2OS cells (ATCC HTB-96) overexpressing recombinant SGK-1 and GSK3beta after transfection with recombinant BacMam viruses.

U2OS cells were cultured in 1:1 Dulbecco modified Eagle medium/Ham's F12 and 10% heat inactivated fetal calf serum (FCS Gold) at 37° C., 7% CO$_2$ and 95% relative humidity. Cells were harvested and mixed with BacMam virus containing expression constructs for human SGK-1 (amino acids S61-L431 with serine 422 replaced by aspartate) at an MOI (multiplicity of infection) of 50 and BacMam virus containing expression constructs for human GSK3beta at an MOI of 125. Cell suspension mixed with BacMam viruses was seeded in 96 well μCLEAR plates (Greiner) at 3×10$^4$ cells per well in 250 μL medium. To reduce background phosphorylation of GSK3beta by AKT, 1 μL of a selective Akt-inhibitor was added (final concentration 2 μM). 1 μL of a solution of the test compound at 250×final concentration was added. Cells are incubated at 37° C., 7% CO$_2$ and 95% relative humidity. After 6 h, medium was aspirated and 50 μl of fixation solution (3.7% paraformaldehyde in phosphate buffered saline (PBS)) was added for 10 min. After removing the fixation solution, cells were permeabilised by adding 200 μl PBT (0.2% Triton X-100 in PBS) per well for 5 min. After removing PBT, cells were blocked by adding 200 μl of blocking solution (1% bovine serum albumine in PBS) per well. Blocking solution was removed and 50 μl of primary antibody (rabbit anti-phospho-GSK-3beta (Ser9), and mouse anti-GSK-3beta) were added for 1 h. After washing the cells 3 times with PBS, 50 μl of secondary antibody (Alexa Fluor 594 goat anti-rabbit IgG, and Alexa Fluor 488 goat anti-mouse IgG) were added and incubated for 1 h in the dark. After washing the cells 3 times with PBS, 200 μl of PBS were added. Fluorescence signals were measured with the ImageXpress MICRO (Molecular Devices). IC$_{50}$ values were calculated using the ratio of phosphorylated GSK3beta to total GSK3beta to compensate for unspecific effects and are given in Table 2.

TABLE 2

IC$_{50}$ values for inhibition of SGK-1 dependent phosphorylation of GSK3beta in U2OS cells by example compounds

| Example no. | IC$_{50}$ [μM] |
|---|---|
| 1 | 1.4 |
| 5 | 0.63 |
| 6 | 2.1 |
| 7 | 2.6 |
| 12 | 1.5 |
| 14 | 2.9 |
| 15 | 2.4 |
| 16 | 1.5 |
| 35 | 0.69 |

C) Functional Electrophysiological Assay for Determination of SGK-1 Dependent Activation of ENaC-Currents in A6 Cell Monolayers SGK-1 is up-regulated in A6 cells in response to induction of a hypoosmotic shock (Alvarez de la Rosa et al.; J. Gen. Physiol. 124 (2004), 395-407). As a consequence of SGK-1 induction, ENaC function in the plasma membrane is upregulated and the effect of SGK-1 inhibitors on functional ENaC surface expression can be investigated with Ussing chamber technology.

Materials and methods for Ussing chamber measurement of A6 cells: The renal *Xenopus laevis* cell line A6 (Rafferty, K. A.; Mass culture of amphibia cells: methods and observations concerning stability of cell type. In: Biology of Amphibian Tumors, edited by M. Mizell. New York: Springer-Verlag, 1969, p. 52-81) was used for the experiments. Cells were grown in cell culture flasks (Nunc) at 28° C. in a humidified atmosphere with 4% CO$_2$. The culture medium contained a 7:3 mixture of Leibovitz's L-15 (Sigma-Aldrich),/Coon's (Sigma-Aldrich) media supplemented with 10% fetal bovine serum (PAA), 20% sterile water, 25 mM NaHCO$_3$ (Sigma-Aldrich), 100 U/ml penicillin (PAA) and 100 μg/ml streptomycin (PAA). The osmolality of the medium was 270 mOsml/kg H$_2$O). Cells were detached with accutase (PAA) and seeded for electrophysiological measurements into transwell filter inserts (polyester 0.4 μm pore size, Corning) at a density of 0.4×10$^6$ cells/filter. Cells were cultivated for 7-10 days, and confluent A6 cell monolayers were identified by repetitive resistance measurements in cell culture medium using an EVOM$^2$ ohmmeter (World Precision Instruments). Monolayers with a resistance of >10 kOhm were considered confluent. Filters with confluent A6 cells were transferred into a continuously perfused Ussing-chamber, and electrophysiological parameters were measured under open circuit conditions using a transepithelial clamp amplifier (EP Design). Short circuit current (I'sc) was calculated by Ohm's law. The Ringer-solutions for Ussing chamber experiments contained NaCl: 122 mmol/l (isoosmotic=260 mOsml/kg H$_2$O) or 82 mmol/l (hypoosmotic=180 mOsml/kg H$_2$O); KHCO$_3$: 2.5 mmol/l; CaCl$_2$: 1 mmol/l; MgCl$_2$: 1 mmol/l; glucose: 5 mmol/l. The pH was adjusted to 8.2. All measurements were done at room temperature. Amiloride, an inhibitor of epithelial Na$^+$ channel (ENaC)-dependent ion transport, was employed at a concentration of 25 µM.

To evaluate the effects of SGK inhibitors on ENaC-mediated transepithelial currents, A9 monolayers were first equilibrated for 5 min with isoosmotic Ringer-solution from both the luminal and basolateral side of the cell layer. Amiloride was applied to the luminal site to establish the basal ENaC-dependent current (I'sc$_{basal}$). Cell layers were then perfused from the basolateral side for 10 min with compounds in isotonic buffer or control isotonic buffer. SGK signaling leading to increased ENaC activity and subsequent increase in I'sc was stimulated by application of hypoosmotic Ringer-solution for 45 min to both sides of the A6 cell layer. ENaC-dependent I'sc after the hypoosmotic shock (I'sc$_{hypo}$) was determined by application of amiloride at the end of the experiment. Total changes of amiloride-sensitive Isc was calculated as ΔI'sc=I'sc$_{hypo}$-I'sc$_{basal}$. The experimental protocol allows detecting and excluding compounds with an intrinsic effect on ENaC, however, there was no direct effect on ENaC by the compounds under investigation. The inhibition of ΔI'sc by the test compounds was determined relative to the ΔI'sc measured with control monolayers which were not treated with the test compound. IC$_{50}$ value were determined by fitting the data to the general dose-response equation For the compound of example 1, in this test an IC$_{50}$ value of 2.1 µM was determined.

D) Determination of the Effect on Chondrocyte Hypertrophic Differentiation in Mouse Chondrogenic ATDC5 Cells The ATDC5 cell assay was used as in vitro model to determine the effects of the compounds of the invention on chondrocyte hypertrophic differentiation by monitoring the expression levels of collagen type X (Col10a1) as specific marker of chondrocyte hypertrophy.

Background: ATDC5 cells are a clonal mouse embryonic cell line derived from multipotent AT805 teratocarcinoma cells (Atsumi T, Miwa Y, Kimata K, Ikawa Y.; A chondrogenic cell line derived from a differentiating culture of AT805 teratocarcinoma cells. Cell Differ. Dev. 30 (1990), 109-116). The cells can undergo insulin-dependent chondrogenic cell differentiation entailing distinct differentiation stages starting from an undifferentiated, subconfluent stage, a condensation stage, a cartilage nodule formation stage and a calcification stage within 45 days of in vitro culture. Chondrogenic differentiation can be shown by measuring the expression of the cartilage main collagen (Col2a1) and aggrecan (AGC1) and glycosaminoglycan-staining with Alcian Blue within two weeks after insulin-triggered differentiation, and hypertrophic differentiation can be monitored by the expression of collagen type X (Col10a1), a specific marker of chondrocyte hypertrophy within 21 days of in vitro culture. (Shukunami C, Shigeno C, Atsumi T, lshizeki K, Suzuki F, Hiraki Y.; Chondrogenic differentiation of clonal mouse embryonic cell line ATDC5 in vitro: differentiation-dependent gene expression of parathyroid hormone (PTH)/PTH-related peptide receptor. J. Cell. Biol. 133 (1996):457-468). Growth factor BMP-2 is known to stimulate cell differentiation and can stimulate early and late-phase ATDC5 differentiation (Shukunami C, Ohta Y, Sakuda M, Hiraki Y.; Sequential progression of the differentiation program by bone morphogenetic protein-2 in chondrogenic cell line ATDC5. Exp. Cell Res. 241 (1998), 1-11). Thyroid hormone triiodothyronine (T3) promotes hypertrophic differentiation of growth plate chondrocytes (Robson H, Siebler T, Stevens D A, Shalet S M, Williams G R; Thyroid hormone acts directly on growth plate chondrocytes to promote hypertrophic differentiation and inhibit clonal expansion and cell proliferation. Endocrinology. 141 (2000):3887-3897). Addition of BMP2 and T3 can accelerate ATDC5 hypertrophic differentiation leading to the strong induction Col10a1 expression between 10-14 days. SGK-inhibitors were added to differentiating ATDC5 cells for 14 days and Col10a1 gene expression was quantified to determine effects on chondrocyte hypertrophic differentiation.

Cell assay description: ATDC5 cells were maintained in 300 cm2 tissue culture flasks in DMEM/Ham's F12+5% FCS supplemented with 10 µg/ml human transferrin, 30 nM sodium selenite, 50 µg/ml kanamycin and grown at 37° C. in 5% $CO_2$ in 95% air. To initiate cell differentiation, 9.9×10$^4$ cells were plated in 24 well plates and grown for 2 days. Medium was exchanged with DMEM/Ham's F12+5% FCS supplemented with 10 µg/ml human transferrin, 30 nM sodium selenite, 50 µg/ml ascorbic acid and 1 µg/ml BMP2. The assay was run in triplicates, compounds were added in 10% DMSO, and medium changed every 2-3 days including supplementation of compound. At day 7 after initiation of cell differentiation, 1 µM T3 was used as additional supplement in the cell culture.

After two weeks of cell culture, RNA was isolated and converted to cDNA for determination of gene expression by quantitative real-time PCR. Cells were lysed in 600 µl of RLT-buffer (Qiagen) and total RNA was isolated using the RNA-easy Mini RNA isolation Kit (Qiagen) which was run on a Qiacube system (Qiagen) according to the supplier's instructions. RNA was isolated in 30 µl of pure water and the RNA content measured by UV-spectroscopy (Nanodrop, Peqlab). For cDNA synthesis 50 ng total RNA was reverse transcribed using the High Capacity cDNA Reverse Transcription Kit (Applied Biosystems, Product Number 4368813) according to the manufacturers instructions. Briefly, a 20 µl reaction was set up, containing 4 mM dNTPs, random primers, RNAse inhibitor and 1 µl MultiScribe reverse transcriptase and incubated for 10 min at 25° C., 120 min at 37° C., 5 min at 85° C.

Quantitative Real-Time PCR: Taqman Fast PCR reaction was performed in a 20 µl volume using Taqman Fast Advanced Master Mix (Applied Biosystems, product number 4444965) and Taqman Gene expression assays for RPL37a (Applied Biosystems, product number Mm01253851_g1) as housekeeping gene and Col10a1 (Applied Biosystems, product number Mm00487041_m1) for Collagen type X expression. Briefly, 2 µl of the cDNA-reaction was combined with 10 µl 2× Taqman Fast Advanced Master Mix, 1 µl of Taqman Gene Expression Assay containing primers and 5'-Fam-labelled minor groove binding Taqman probe according to the manufacturers instructions in fast thermal cycling 96 well plates. 40 amplification rounds were run in a Viaa7 Real Time PCR System (Applied Biosystems), with 1 sec at 95° C. for denaturing and 20 sec at 60° C. for annealing/extension. Fluorescence data were collected and converted to Ct-Values and expressed values were calculated based on the comparative Ct method (Nat. Protoc. 3 (2008), 1101-1108); Analyzing real-time PCR data by the comparative C(T) method).

For the compound of example 6, in this test for the inhibition of collagen type X expression an IC$_{50}$ value of 0.559 µM was determined.

The invention claimed is:
1. A compound of the formula I, in any of its stereoisomeric forms or a mixture of stereoisomeric forms in any ratio, or a pharmaceutically acceptable salt thereof:

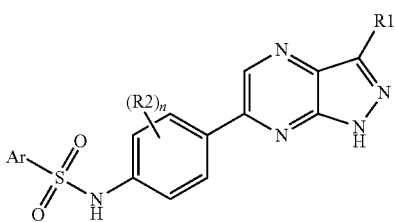

wherein
- Ar is selected from the series consisting of phenyl and a 5-membered or 6-membered monocyclic aromatic heterocycle comprising 1, 2 or 3 identical or different ring heteroatoms selected from the series consisting of nitrogen, oxygen and sulfur and bonded via a ring carbon atom, which are all unsubstituted or substituted by one or more identical or different substituents R10;
- n is selected from the series consisting of 0, 1 and 2;
- R1 is selected from the series consisting of hydrogen, —N(R11)-R12, —N(R13)-C(O)—R14, —N(R13)-S(O)$_2$—R15, —N(R13)-C(O)—NH—R14, —C(O)—N(R16)-R17, —CN, (C$_1$-C$_4$)-alkyl and —(C$_1$-C$_4$)-alkyl-O—R18;
- R2 is selected from the series consisting of halogen, —(C$_1$-C$_4$)-alkyl, —O—(C$_1$-C$_4$)-alkyl and —CN;
- R10 is selected from the series consisting of halogen, (C$_1$-C$_4$)-alkyl, (C$_3$-C$_7$)-cycloalkyl, —(C$_1$-C$_4$)-alkyl-(C$_3$-C$_7$)-cycloalkyl, —O—(C$_1$-C$_4$)-alkyl, —O—(C$_3$-C$_7$)-cycloalkyl, —O—(C$_1$-C$_4$)-alkyl-(C$_3$-C$_7$)-cycloalkyl-, —N(R19)-R20, —N(R21)-N(R19)-R20, —N(R21)-C(O)—R22, —NO$_2$, —C(O)—N(R23)-R24 and —CN, and two groups R10 bonded to adjacent ring carbon atoms in Ar, together with the carbon atoms carrying them, can form a 5-membered to 8-membered unsaturated ring which comprises 0, 1 or 2 identical or different ring heteroatoms selected from the series consisting of nitrogen, oxygen and sulfur, and which is unsubstituted or substituted by one or more identical or different substituents selected from the series consisting of halogen, —(C$_1$-C$_4$)-alkyl, —O—(C$_1$-C$_4$)-alkyl and —CN;
- R11 and R12 are independently of one another selected from the series consisting of hydrogen, (C$_1$-C$_4$)-alkyl, (C$_3$-C$_7$)-cycloalkyl and —(C$_1$-C$_4$)-alkyl-(C$_3$-C$_7$)-cycloalkyl, or R11 and R12, together with the nitrogen atom carrying them, form a monocyclic, 4-membered to 7-membered, saturated heterocycle which, in addition to the nitrogen atom carrying R11 and R12, comprises 0 or 1 further ring heteroatom selected from the series consisting of nitrogen, oxygen and sulfur, and which is unsubstituted or substituted by one or more identical or different substituents selected from the series consisting of fluorine and (C$_1$-C$_4$)-alkyl;
- R13 is selected from the series consisting of hydrogen, (C$_1$-C$_4$)-alkyl and (C$_3$-C$_7$)-cycloalkyl;
- R14 and R15 are independently of one another selected from the series consisting of (C$_1$-C$_8$)-alkyl, (C$_3$-C$_7$)-cycloalkyl, —(C$_1$-C$_4$)-alkyl-(C$_3$-C$_7$)-cycloalkyl, phenyl, —(C$_1$-C$_4$)-alkyl-phenyl, Het and —(C$_1$-C$_4$)-alkyl-Het, wherein phenyl and Het all are unsubstituted or substituted by one or more identical or different substituents R30;
- R16 is selected from the series consisting of hydrogen, (C$_1$-C$_4$)-alkyl and (C$_3$-C$_7$)-cycloalkyl;
- R17 is selected from the series consisting of hydrogen, (C$_1$-C$_8$)-alkyl, (C$_3$-C$_7$)-cycloalkyl, -(C$_1$-C$_4$)-alkyl-(C$_3$-C$_7$)-cycloalkyl, phenyl, —(C$_1$-C$_4$)-alkyl-phenyl, Het and -(C$_1$-C$_4$)-alkyl-Het, wherein phenyl and Het all are unsubstituted or substituted by one or more identical or different substituents R30, or R16 and R17, together with the nitrogen atom carrying them, form a monocyclic, 4-membered to 7-membered, saturated heterocycle which, in addition to the nitrogen atom carrying R16 and R17, comprises 0 or 1 further ring heteroatom selected from the series consisting of nitrogen, oxygen and sulfur, and which is unsubstituted or substituted by one or more identical or different substituents selected from the series consisting of fluorine and (C$_1$-C$_4$)-alkyl;
- R18 is selected from the series consisting of hydrogen and (C$_1$-C$_4$)-alkyl;
- R19 is selected from the series consisting of hydrogen, (C$_1$-C$_4$)-alkyl and (C$_3$-C$_7$)-cycloalkyl;
- R20 is selected from the series consisting of hydrogen, (C$_1$-C$_8$)-alkyl, (C$_3$-C$_7$)-cycloalkyl, -(C$_1$-C$_4$)-alkyl-(C$_3$-C$_7$)-cycloalkyl, phenyl, —(C$_1$-C$_4$)-alkyl-phenyl, Het and -(C$_1$-C$_4$)-alkyl-Het, wherein phenyl and Het all are unsubstituted or substituted by one or more identical or different substituents R30, or R19 and R20, together with the nitrogen atom carrying them, form a monocyclic, 4-membered to 7-membered, saturated heterocycle which, in addition to the nitrogen atom carrying R19 and R20, comprises 0 or 1 further ring heteroatom selected from the series consisting of nitrogen, oxygen and sulfur, and which is unsubstituted or substituted by one or more identical or different substituents selected from the series consisting of fluorine and (C$_1$-C$_4$)-alkyl;
- R21 is selected from the series consisting of hydrogen, (C$_1$-C$_4$)-alkyl and (C$_3$-C$_7$)-cycloalkyl;
- R22 is selected from the series consisting of (C$_1$-C$_4$)-alkyl, (C$_3$-C$_7$)-cycloalkyl and —(C$_1$-C$_4$)-alkyl-(C$_3$-C$_7$)-cycloalkyl;
- R23 and R24 are independently of one another selected from the series consisting of hydrogen and (C$_1$-C$_4$)-alkyl;
- R30 is selected from the series consisting of halogen, (C$_1$-C$_4$)-alkyl, —O—(C$_1$-C$_4$)-alkyl and —CN;
- Het is a monocyclic, 4-membered to 7-membered, saturated, partially unsaturated or aromatic heterocycle which comprises 1 or 2 identical or different ring heteroatoms selected from the series consisting of nitrogen, oxygen and sulfur, and which is bonded via a ring carbon atom;
- wherein all cycloalkyl groups can be substituted by one or more identical substituents selected from the series consisting of fluorine and (C$_1$-C$_4$)-alkyl;
- wherein all alkyl groups, independently of any other substituents which can be present on an alkyl group, can be substituted by one or more fluorine substituents.

2. The compound of claim 1, in any of its stereoisomeric forms or a mixture of stereoisomeric forms in any ratio, or a pharmaceutically acceptable salt thereof, wherein Ar is selected from the series consisting of phenyl and a 5-membered or 6-membered monocyclic aromatic heterocycle comprising 1 or 2 identical or different ring heteroatoms selected from the series consisting of nitrogen, oxygen and sulfur and bonded via a ring carbon atom, which are all unsubstituted or substituted by one or more identical or different substituents R10;
  n is selected from the series consisting of 0, 1 and 2;

R1 is selected from the series consisting of hydrogen, —N(R11)-R12, —N(R13)-C(O)—R14, —N(R13)-S(O)$_2$—R15, —N(R13)-C(O)—NH—R14, (C$_1$-C$_4$)-alkyl and —(C$_1$-C$_4$)-alkyl-O—R18;

R2 is selected from the series consisting of halogen, —(C$_1$-C$_4$)-alkyl and —CN;

R10 is selected from the series consisting of halogen, (C$_1$-C$_4$)-alkyl, —O—(C$_1$-C$_4$)-alkyl, —N(R19)-R20, —N(R21)-N(R19)-R20, —N(R21)-C(O)—R22, —NO$_2$, —C(O)—N(R23)-R24 and —CN, and two groups R10 bonded to adjacent ring carbon atoms in Ar, together with the carbon atoms carrying them, can form a 5-membered to 7-membered unsaturated ring which comprises 0, 1 or 2 identical or different ring heteroatoms selected from the series consisting of nitrogen, oxygen and sulfur, and which is unsubstituted or substituted by one or more identical or different substituents selected from the series consisting of halogen, —(C$_1$-C$_4$)-alkyl and —CN;

R11 and R12 are independently of one another selected from the series consisting of hydrogen and (C$_1$-C$_4$)-alkyl, or R11 and R12, together with the nitrogen atom carrying them, form a monocyclic, 4-membered to 6-membered, saturated heterocycle which, in addition to the nitrogen atom carrying R11 and R12, comprises 0 or 1 further ring heteroatom selected from the series consisting of nitrogen, oxygen and sulfur, and which is unsubstituted or substituted by one or more identical or different substituents selected from the series consisting of fluorine and (C$_1$-C$_4$)-alkyl;

R13 is selected from the series consisting of hydrogen and (C$_1$-C$_4$)-alkyl;

R14 and R15 are independently of one another selected from the series consisting of (C$_3$-C$_7$)-cycloalkyl, phenyl, —(C$_1$-C$_4$)-alkyl-phenyl, Het and —(C$_1$-C$_4$)-alkyl-Het, wherein phenyl and Het all are unsubstituted or substituted by one or more identical or different substituents R30;

R18 is selected from the series consisting of hydrogen and (C$_1$-C$_4$)-alkyl;

R19 is selected from the series consisting of hydrogen and (C$_1$-C$_4$)-alkyl;

R20 is selected from the series consisting of hydrogen, (C$_1$-C$_8$)-alkyl, (C$_3$-C$_7$)-cycloalkyl and —(C$_1$-C$_4$)-alkyl-(C$_3$-C$_7$)-cycloalkyl;

or R19 and R20, together with the nitrogen atom carrying them, form a monocyclic, 4-membered to 6-membered, saturated heterocycle which, in addition to the nitrogen atom carrying R19 and R20, comprises 0 or 1 further ring heteroatom selected from the series consisting of nitrogen, oxygen and sulfur, and which is unsubstituted or substituted by one or more identical or different substituents selected from the series consisting of fluorine and (C$_1$-C$_4$)-alkyl;

R21 is selected from the series consisting of hydrogen and (C$_1$-C$_4$)-alkyl;

R22 is selected from (C$_1$-C$_4$)-alkyl and (C$_3$-C$_7$)-cycloalkyl;

R23 and R24 are independently of one another selected from the series consisting of hydrogen and (C$_1$-C$_4$)-alkyl;

R30 is selected from the series consisting of halogen, (C$_1$-C$_4$)-alkyl and —CN;

Het is a monocyclic, 4-membered to 7-membered, saturated, partially unsaturated or aromatic heterocycle which comprises 1 or 2 identical or different ring heteroatoms selected from the series consisting of nitrogen, oxygen and sulfur, and which is bonded via a ring carbon atom;

wherein all cycloalkyl groups can be substituted by one or more identical substituents selected from the series consisting of fluorine and (C$_1$-C$_4$)-alkyl;

wherein all alkyl groups, independently of any other substituents which can be present on an alkyl group, can be substituted by one or more fluorine substituents.

3. The compound of claim 1, in any of its stereoisomeric forms or a mixture of stereoisomeric forms in any ratio, or a pharmaceutically acceptable salt thereof, wherein Ar is selected from the series consisting of phenyl and a 5-membered or 6-membered monocyclic aromatic heterocycle comprising 1 or 2 identical or different ring heteroatoms selected from the series consisting of nitrogen, oxygen and sulfur and bonded via a ring carbon atom, which are all unsubstituted or substituted by one or more identical or different substituents R10;

n is selected from the series consisting of 0 and 1;

R1 is selected from the series consisting of hydrogen, —N(R11)-R12, —N(R13)-C(O)—R14, —N(R13)-S(O)$_2$—R15, —N(R13)-C(O)—NH—R14 and (C$_1$-C$_4$)-alkyl;

R2 is selected from the series consisting of halogen and —(C$_1$-C$_4$)-alkyl;

R10 is selected from the series consisting of halogen, (C$_1$-C$_4$)-alkyl, —O—(C$_1$-C$_4$)-alkyl, —N(R19)-R20, —N(R21)-N(R19)-R20, —N(R21)-C(O)—R22, —NO$_2$ and —CN, and two groups R10 bonded to adjacent ring carbon atoms in Ar, together with the carbon atoms carrying them, can form a 5-membered to 7-membered unsaturated ring which comprises 0, 1 or 2 identical or different ring heteroatoms selected from the series consisting of nitrogen, oxygen and sulfur, and which is unsubstituted or substituted by one or more identical or different substituents selected from the series consisting of halogen and —(C$_1$-C$_4$)-alkyl;

R11 and R12 are independently of one another selected from the series consisting of hydrogen and (C$_1$-C$_4$)-alkyl, or R11 and R12, together with the nitrogen atom carrying them, form a monocyclic, 5-membered or 6-membered, saturated heterocycle which, in addition to the nitrogen atom carrying R11 and R12, comprises 0 or 1 further ring heteroatom selected from the series consisting of nitrogen, oxygen and sulfur, and which is unsubstituted or substituted by one or more identical or different substituents selected from the series consisting of fluorine and (C$_1$-C$_4$)-alkyl;

R13 is selected from the series consisting of hydrogen and (C$_1$-C$_4$)-alkyl;

R14 and R15 are independently of one another selected from the series consisting of (C$_3$-C$_7$)-cycloalkyl, phenyl, —(C$_1$-C$_4$)-alkyl-phenyl, Het and —(C$_1$-C$_4$)-alkyl-Het, wherein phenyl and Het all are unsubstituted or substituted by one or more identical or different substituents R30;

R19 is selected from the series consisting of hydrogen and (C$_1$-C$_4$)-alkyl;

R20 is selected from the series consisting of hydrogen and (C$_1$-C$_4$)-alkyl;

or R19 and R20, together with the nitrogen atom carrying them, form a monocyclic, 4-membered to 6-membered, saturated heterocycle which, in addition to the nitrogen atom carrying R19 and R20, comprises 0 or 1 further ring heteroatom selected from the series consisting of nitrogen, oxygen and sulfur, and which is unsubstituted or substituted by one or more identical or different substituents selected from the series consisting of fluorine and ($C_1$-$C_4$)-alkyl;

R21 is selected from the series consisting of hydrogen and ($C_1$-$C_4$)-alkyl;

R22 is ($C_1$-$C_4$)-alkyl;

R30 is selected from the series consisting of halogen, ($C_1$-$C_4$)-alkyl and —CN;

Het is a monocyclic, 5-membered or 6-membered, saturated, partially unsaturated or aromatic heterocycle which comprises 1 or 2 identical or different ring heteroatoms selected from the series consisting of nitrogen, oxygen and sulfur, and which is bonded via a ring carbon atom;

wherein all cycloalkyl groups can be substituted by one or more identical substituents selected from the series consisting of fluorine and ($C_1$-$C_4$)-alkyl;

wherein all alkyl groups, independently of any other substituents which can be present on an alkyl group, can be substituted by one or more fluorine substituents.

4. The compound of claim 1, in any of its stereoisomeric forms or a mixture of stereoisomeric forms in any ratio, or a pharmaceutically acceptable salt thereof, wherein Ar is phenyl which is unsubstituted or substituted by one or more identical or different substituents R10;

n is selected from the series consisting of 0 and 1;

R1 is selected from the series consisting of hydrogen, —N(R11)-R12, —N(R13)-C(O)—R14, —N(R13)-S(O)$_2$—R15, —N(R13)-C(O)—NH—R14 and ($C_1$-$C_4$)-alkyl;

R2 is selected from the series consisting of halogen and —($C_1$-$C_4$)-alkyl;

R10 is selected from the series consisting of halogen, ($C_1$-$C_4$)-alkyl, —O—($C_1$-$C_4$)-alkyl, —N(R19)-R20, —N(R21)-N(R19)-R20, —N(R21)-C(O)—R22, —NO$_2$ and —CN, and two groups R10 bonded to adjacent ring carbon atoms in Ar, together with the carbon atoms carrying them, can form a 5-membered to 7-membered unsaturated ring which comprises 0, 1 or 2 oxygen atoms as ring heteroatoms, and which is unsubstituted or substituted by one or more identical or different substituents selected from the series consisting of halogen and —($C_1$-$C_4$)-alkyl;

R11 and R12 are independently of one another selected from the series consisting of hydrogen and ($C_1$-$C_4$)-alkyl;

R13 is selected from the series consisting of hydrogen and ($C_1$-$C_4$)-alkyl;

R14 and R15 are independently of one another selected from the series consisting of ($C_3$-$C_7$)-cycloalkyl, phenyl, —($C_1$-$C_4$)-alkyl-phenyl, Het and —($C_1$-$C_4$)-alkyl-Het, wherein phenyl and Het all are unsubstituted or substituted by one or more identical or different substituents R30;

R19 is selected from the series consisting of hydrogen and ($C_1$-$C_4$)-alkyl;

R20 is selected from the series consisting of hydrogen and ($C_1$-$C_4$)-alkyl;

R21 is selected from the series consisting of hydrogen and ($C_1$-$C_4$)-alkyl;

R22 is ($C_1$-$C_4$)-alkyl;

R30 is selected from the series consisting of halogen and ($C_1$-$C_4$)-alkyl;

Het is a monocyclic, 5-membered or 6-membered, saturated, partially unsaturated or aromatic heterocycle which comprises 1 ring heteroatom selected from the series consisting of nitrogen, oxygen and sulfur, and which is bonded via a ring carbon atom;

wherein all cycloalkyl groups can be substituted by one or more identical substituents selected from the series consisting of fluorine and ($C_1$-$C_4$)-alkyl;

wherein all alkyl groups, independently of any other substituents which can be present on an alkyl group, can be substituted by one or more fluorine substituents.

5. The compound of claim 1, in any of its stereoisomeric forms or a mixture of stereoisomeric forms in any ratio, or a pharmaceutically acceptable salt thereof, wherein Ar is selected from the series consisting of 2,3-dichloro-phenyl, 2,5-dichloro-phenyl, 5-chloro-2-hydrazino-phenyl, 5-chloro-2-cyano-phenyl, 2-cyano-5-methyl-phenyl, 2-fluoro-5-methyl-phenyl, 2-chloro-5-methoxy-phenyl, 2,5-dichloro-thiophen-3-yl, 8-chloro-3,4-dihydro-2H-benzo[b][1,4]dioxepin-7-yl, 5-chloro-1,3-dimethyl-pyrazol-4-yl, naphthalen-1-yl, 2,4,6-trichloro-phenyl, 5-chloro-2-fluoro-phenyl, 2,4,5-trifluoro-phenyl, 2,4,5-trichloro-phenyl, 5-chloro-2,4-difluoro-phenyl, 2,3,4-trichloro-phenyl, 2,3,4-trifluoro-phenyl, 2-chloro-4-trifluoromethyl-phenyl, 5-cyano-2-fluoro-phenyl, 2-cyano-5-methoxy-phenyl, 2-cyano-5-fluoro-phenyl, 2-fluoro-5-methoxy-phenyl, 4-acetylamino-2-methyl-phenyl, 2-methyl-5-nitro-phenyl, and 2-nitro-4-trifluoromethyl-phenyl;

n is selected from the series consisting of 0 and 1;

R1 is selected from the series consisting of hydrogen, —N(R11)-R12, —N(R13)-C(O)—R14, —N(R13)-S(O)$_2$—R15, —N(R13)-C(O)—NH—R14 and ($C_1$-$C_4$)-alkyl;

R2 is selected from the series consisting of halogen and —($C_1$-$C_4$)-alkyl;

R11 and R12 are independently of one another selected from the series consisting of hydrogen and ($C_1$-$C_4$)-alkyl;

R13 is selected from the series consisting of hydrogen and ($C_1$-$C_4$)-alkyl;

R14 and R15 are independently of one another selected from the series consisting of ($C_3$-$C_7$)-cycloalkyl, phenyl, —($C_1$-$C_4$)-alkyl-phenyl, Het and —($C_1$-$C_4$)-alkyl-Het, wherein phenyl and Het all are unsubstituted or substituted by one or more identical or different substituents R30;

R30 is selected from the series consisting of halogen and ($C_1$-$C_4$)-alkyl;

Het is a monocyclic, 5-membered or 6-membered, saturated, partially unsaturated or aromatic heterocycle which comprises 1 ring heteroatom selected from the series consisting of nitrogen, oxygen and sulfur, and which is bonded via a ring carbon atom;

wherein all cycloalkyl groups can be substituted by one or more identical substituents selected from the series consisting of fluorine and ($C_1$-$C_4$)-alkyl;

wherein all alkyl groups, independently of any other substituents which can be present on an alkyl group, can be substituted by one or more fluorine substituents.

6. The compound of claim 1, in any of its stereoisomeric forms or a mixture of stereoisomeric forms in any ratio, or a pharmaceutically acceptable salt thereof, wherein Ar is selected from the series consisting of 2,3-dichloro-phenyl, 2,5-dichloro-phenyl, 5-chloro-2-hydrazino-phenyl, 5-chloro-2-cyano-phenyl, 2-cyano-5-methyl-phenyl, 2-fluoro-5-methyl-phenyl, 2-chloro-5-methoxy-phenyl, 2,5-dichloro-thiophen-3-yl, 8-chloro-3,4-dihydro-2H-benzo[b][1,4]dioxepin-7-yl, 5-chloro-1,3-dimethyl-pyrazol-4-yl, naphthalen-1-yl, 5-cyano-2-fluoro-phenyl, 2-cyano-5-methoxy-phenyl, 2-cyano-5-fluoro-phenyl, 2-fluoro-5-methoxyphenyl, 4-acetylamino-2-methyl-phenyl, 2-methyl-5-nitro-phenyl, and 2-nitro-4-trifluoromethyl-phenyl;

n is selected from the series consisting of 0 and 1;

R1 is selected from the series consisting of hydrogen, —N(R11)-R12, —N(R13)-C(O)—R14, —N(R13)-S(O)$_2$—R15, —N(R13)-C(O)—NH—R14 and (C$_1$-C$_4$)-alkyl;

R2 is selected from the series consisting of halogen and —(C$_1$-C$_4$)-alkyl;

R11 and R12 are independently of one another selected from the series consisting of hydrogen and (C$_1$-C$_4$)-alkyl;

R13 is selected from the series consisting of hydrogen and (C$_1$-C$_4$)-alkyl;

R14 and R15 are independently of one another selected from the series consisting of (C$_3$-C$_7$)-cycloalkyl, phenyl, —(C$_1$-C$_4$)-alkyl-phenyl, Het and —(C$_1$-C$_4$)-alkyl-Het, wherein phenyl and Het all are unsubstituted or substituted by one or more identical or different substituents R30;

R30 is selected from the series consisting of halogen and (C$_1$-C$_4$)-alkyl;

Het is a monocyclic, 5-membered or 6-membered, saturated, partially unsaturated or aromatic heterocycle which comprises 1 ring heteroatom selected from the series consisting of nitrogen, oxygen and sulfur, and which is bonded via a ring carbon atom;

wherein all cycloalkyl groups can be substituted by one or more identical substituents selected from the series consisting of fluorine and (C$_1$-C$_4$)-alkyl;

wherein all alkyl groups, independently of any other substituents which can be present on an alkyl group, can be substituted by one or more fluorine substituents.

7. The compound of claim 1, in any of its stereoisomeric forms or a mixture of stereoisomeric forms in any ratio, or a pharmaceutically acceptable salt thereof, wherein R1 is selected from the series consisting of hydrogen and (C$_1$-C$_4$)-alkyl.

8. The compound of claim 1, in any of its stereoisomeric forms or a mixture of stereoisomeric forms in any ratio, or a pharmaceutically acceptable salt thereof, wherein R1 is selected from the series consisting of —N(R11)-R12, —N(R13)-C(O)—R14, —N(R13)-S(O)$_2$—R15 and —N(R13)-C(O)—NH—R14.

9. The compound of claim 1, or a pharmaceutically acceptable salt thereof, which is selected from the series consisting of:

N-[4-(3-amino-1H-pyrazolo[3,4-b]pyrazin-6-yl)phenyl]-2,3-dichloro-benzenesulfonamide,
2,5-dichloro-N-[4-(1H-pyrazolo[3,4-b]pyrazin-6-yl)phenyl]benzenesulfonamide,
2,5-dichloro-N-[2-fluoro-4-(1H-pyrazolo[3,4-b]pyrazin-6-yl)phenyl]benzenesulfonamide,
2,3-dichloro-N-[2-fluoro-4-(1H-pyrazolo[3,4-b]pyrazin-6-yl)-phenyl]-benzenesulfonamide,
N-[4-(3-amino-1H-pyrazolo[3,4-b]pyrazin-6-yl)phenyl]-2,5-dichloro-benzenesulfonamide,
N-[4-(3-amino-1H-pyrazolo[3,4-b]pyrazin-6-yl)phenyl]-5-chloro-2-hydrazino-benzenesulfonamide,
N-[4-(3-amino-1H-pyrazolo[3,4-b]pyrazin-6-yl)-2-fluoro-phenyl]-5-chloro-2-fluoro-benzenesulfonamide,
N-[4-(3-amino-1H-pyrazolo[3,4-b]pyrazin-6-yl)-2-fluoro-phenyl]-2,5-dichloro-benzenesulfonamide,
N-[4-(3-amino-1H-pyrazolo[3,4-b]pyrazin-6-yl)-2-fluoro-phenyl]-2,3-dichloro-benzenesulfonamide,
2,5-dichloro-N-[4-(3-methyl-1H-pyrazolo[3,4-b]pyrazin-6-yl)phenyl]benzenesulfonamide,
2,3-dichloro-N-[4-(3-methyl-1H-pyrazolo[3,4-b]pyrazin-6-yl)phenyl]benzenesulfonamide,
5-chloro-2-fluoro-N-[4-(3-methyl-1H-pyrazolo[3,4-b]pyrazin-6-yl)phenyl]benzenesulfonamide,
5-chloro-2-cyano-N-[4-(3-methyl-1H-pyrazolo[3,4-b]pyrazin-6-yl)phenyl]benzenesulfonamide,
2-cyano-5-methyl-N-[4-(3-methyl-1H-pyrazolo[3,4-b]pyrazin-6-yl)phenyl]benzenesulfonamide,
2-fluoro-5-methyl-N-[4-(3-methyl-1H-pyrazolo[3,4-b]pyrazin-6-yl)phenyl]benzenesulfonamide,
2-chloro-5-methoxy-N-[4-(3-methyl-1H-pyrazolo[3,4-b]pyrazin-6-yl)phenyl]benzenesulfonamide,
N-[4-(3-amino-1H-pyrazolo[3,4-b]pyrazin-6-yl)phenyl]2-cyano-5-methyl-benzenesulfonamide,
N-[4-(3-amino-1H-pyrazolo[3,4-b]pyrazin-6-yl)phenyl]-2-chloro-5-methoxy-benzenesulfonamide,
N-[4-(3-amino-1H-pyrazolo[3,4-b]pyrazin-6-yl)phenyl]-2-fluoro-5-methyl-benzenesulfonamide,
N-[4-(3-amino-1H-pyrazolo[3,4-b]pyrazin-6-yl)-phenyl]-5-chloro-2-cyano-benzenesulfonamide,
N-[4-(3-amino-1H-pyrazolo[3,4-b]pyrazin-6-yl)phenyl]-2,5-dichloro-thiophene-3-sulfonamide,
N-[4-(3-amino-1H-pyrazolo[3,4-b]pyrazin-6-yl)phenyl]-8-chloro-3,4-dihydro-2H-benzo[b][1,4]dioxepine-7-sulfonamide,
N-[4-(3-amino-1H-pyrazolo[3,4-b]pyrazin-6-yl)phenyl]-5-chloro-1,3-dimethyl-pyrazole-4-sulfonamide,
N-[6-[4-[(2-fluoro-5-methyl-phenyl)sulfonylamino]phenyl)-1H-pyrazolo[3,4-b]pyrazin-3-yl]cyclopropanecarboxamide,
N-[6-[4-[(2-fluoro-5-methyl-phenyl)sulfonylamino]phenyl]-1H-pyrazolo[3,4-b]pyrazin-3-yl]tetrahydropyran-4-carboxamide,
N-[6-[4-[(2-fluoro-5-methyl-phenyl)sulfonylamino]phenyl]-1H-pyrazolo[3,4-b]pyrazin-3-yl]piperidine-4-carboxamide,
N-[6-[4-[(2-fluoro-5-methyl-phenyl)sulfonylamino]phenyl]-1H-pyrazolo[3,4-b]pyrazin-3-yl)cyclopentanecarboxamide,
2,3-dichloro-N-[6-[4-[(2-fluoro-5-methyl-phenyl)sulfonylamino]phenyl]-1H-pyrazolo[3,4-b]pyrazin-3-yl]benzamide,
N-[6-[4-[(2-fluoro-5-methyl-phenyl)sulfonylamino]phenyl)-1H-pyrazolo[3,4-b]pyrazin-3-yl]cyclohexanecarboxamide,
N-[6-[4-[(2-fluoro-5-methyl-phenyl)sulfonylamino]phenyl)-1H-pyrazolo[3,4-b]pyrazin-3-yl]-2-phenyl-acetamide,
N-[6-[4-[(2-fluoro-5-methyl-phenyl)sulfonylamino]phenyl]-1H-pyrazolo[3,4-b]pyrazin-3-yl]thiophene-3-carboxamide, 4-chloro-N-[6-[4-[(2-fluoro-5-methyl-phenyl)sulfonylamino]phenyl]-1H-pyrazolo[3,4-b]pyrazin-3-yl]benzamide,
N-[4-(3-amino-1H-pyrazolo[3,4-b]pyrazin-6-yl)phenyl]naphthalene-1-sulfonamide,
N-[4-(3-amino-1H-pyrazolo[3,4-b]pyrazin-6-yl)phenyl]-2,4,6-trichloro-benzenesulfonamide,
N-[4-(3-amino-1H-pyrazolo[3,4-b]pyrazin-6-yl)phenyl]-5-chloro-2-fluoro-benzenesulfonamide,
N-[4-(3-amino-1H-pyrazolo[3,4-b]pyrazin-6-yl)phenyl]-2,4,5-trifluoro-benzenesulfonamide,
N-[4-(3-amino-1H-pyrazolo[3,4-b]pyrazin-6-yl)phenyl]-2,4,5-trichloro-benzenesulfonamide,
N-[4-(3-amino-1H-pyrazolo[3,4-b]pyrazin-6-yl)phenyl]-5-chloro-2,4-difluoro-benzenesulfonamide,
N-[4-(3-amino-1H-pyrazolo[3,4-b]pyrazin-6-yl)phenyl]-2,3,4-trichloro-benzenesulfonamide, N-[4-(3-amino-1H-pyrazolo[3,4-b]pyrazin-6-yl)phenyl]-
2,3,4-trifluoro-benzenesulfonamide,
N-[4-(3-amino-1H-pyrazolo[3,4-b]pyrazin-6-yl)phenyl]-
2-chloro-4-trifluoromethyl-benzenesulfonamide,
5-chloro-N-[4-[3-[(5-chloro-2,4-difluoro-phenyl)sulfo-
nylamino]-1H-pyrazolo[3,4-b]pyrazin-6-yl]phenyl]-2,
4-difluoro-benzenesulfonamide, 5-chloro-N-[4-[3-[(5-
chloro-1,3-dimethyl-pyrazol-4-yl)sulfonylamino]-1H-
pyrazolo[3,4-b]pyrazin-6-yl]phenyl]-1,3-dimethyl-
pyrazole-4-sulfonamide, 2,4,5-trifluoro-N-[4-[3-[(2,4,
5-trifluorophenyl)sulfonylamino]-1H-pyrazolo[3,4-b]
pyrazin-6-yl]phenyl]benzenesulfonamide,
N-[4-(3-amino-1H-pyrazolo[3,4-b]pyrazin-6-yl)-phenyl]-
5-cyano-2-fluoro-benzenesulfonamide,
N-[4-(3-amino-1H-pyrazolo[3,4-b]pyrazin-6-yl)-phenyl]-
2-cyano-5-methoxy-benzenesulfonamide,
N-[4-(3-amino-1H-pyrazolo[3,4-b]pyrazin-6-yl)-phenyl]-
2-cyano-5-fluoro-benzenesulfonamide,
N-[4-(3-amino-1H-pyrazolo[3,4-b]pyrazin-6-yl)-phenyl]-
2-fluoro-5-methoxy-benzenesulfonamide,
1-[6-[4-[(2-fluoro-5-methyl-phenyl)sulfonylamino]phe-
nyl]-1H-pyrazolo[3,4-b]pyrazin-3-yl]-3-(3-pyridyl)
urea,
1-(4-chlorophenyl)-3-[6-[4-[(2-fluoro-5-methyl-phenyl)
sulfonylamino]phenyl]-1H-pyrazolo[3,4-b]pyrazin-3-
yl]urea,
2-chloro-N-[4-[3-[[2-chloro-4-trifluoromethyl-phenyl]
sulfonylamino]-1H-pyrazolo[3,4-b]pyrazin-6-yl]phe-
nyl]-4-trifluoromethyl-benzenesulfonamide,
N-[6-[4-(1-naphthylsulfonylamino)phenyl]-1H-pyrazolo
[3,4-b]pyrazin-3-yl]naphthalene-1-sulfonamide,
2,4,6-trichloro-N-[4-[3-[(2,4,6-trichlorophenyl)sulfony-
lamino]-1H-pyrazolo[3,4-b]pyrazin-6-yl]phenyl]ben-
zenesulfonamide,
N-[3-methyl-4-[[4-(3-methyl-1H-pyrazolo[3,4-b]
pyrazin-6-yl)phenyl]sulfamoyl]phenyl]acetamide,
2-methyl-N-[4-(3-methyl-1H-pyrazolo[3,4-b]pyrazin-6-
yl)phenyl]-5-nitro-benzenesulfonamide, and
N-[4-(3-methyl-1H-pyrazolo[3,4-b]pyrazin-6-yl)phenyl]-
2-nitro-4-trifluoromethyl-benzenesulfonamide.

10. A pharmaceutical composition comprising the compound of claim 1, in any of its stereoisomeric forms or a mixture of stereoisomeric forms in any ratio, or a pharmaceutically acceptable salt thereof, and a pharmaceutically acceptable carrier.

11. A method of modulating serum and glucocorticoid-regulated kinase 1 activity in a patient in need thereof, the method comprising administering to said patient a therapeutically effective amount of the pharmaceutical composition of claim 10.

12. The method of claim 11, wherein said pharmaceutical composition comprises a compound of Formula I as provided in claim 1 in which R1 in Formula I is selected from the group consisting of hydrogen, —N(R11)-R12, —N(R13)-C(O)—R14, —N(R13)-S(O)$_2$—R15, —N(R13)-C(O)—NH—R14 and ($C_1$-$C_4$)-alkyl.

13. The method of claim 11, wherein said pharmaceutical composition comprises a compound of Formula I as provided in claim 1 in which R1 in Formula I is selected from the group consisting of —N(R11)-R12, —N(R13)-C(O)—R14, —N(R13)-S(O)$_2$—R15 and —N(R13)-C(O)—NH—R14.

14. The method of claim 11, wherein said pharmaceutical composition comprises a compound of Formula I as provided in claim 1 in which R1 in Formula I is selected from the group consisting of hydrogen and ($C_1$-$C_4$)-alkyl.

15. A method of treating degenerative cartilage changes in a patient in need thereof, the method comprising administering to said patient a therapeutically effective amount of the pharmaceutical composition of claim 10.

16. A method of treating osteoarthritis in a patient in need thereof, the method comprising administering to said patient a therapeutically effective amount of the pharmaceutical composition of claim 10.

17. A process for preparing the compound of formula I according to claim 1, or a pharmaceutically acceptable salt thereof, comprising:

(i) reacting a compound of the formula II:

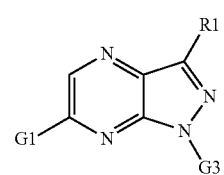

wherein R1 is as defined in claim 1;
G1 is halogen or sulfonyloxy; and
G3 is hydrogen;
with a compound of the formula III:

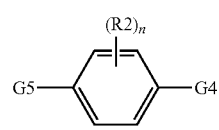

wherein R2 and n are as defined in claim 1;
G4 is Ar—S(O)$_2$—NH—, where Ar is as defined in the compound of the formula I according to claim 1; and
G5 is a trialkylstannyl group, a boronic acid group, a boronic acid ester group or a cyclic boronic acid ester group;
to give a compound of formula I:

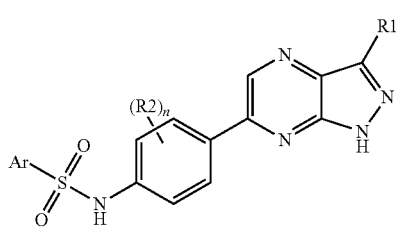

wherein R1, R2 and n are as defined in claim 1; and
Ar is as defined in the compound of formula I according to claim 1; and
(ii) optionally converting the compound of formula I above into a pharmaceutically acceptable salt thereof.

* * * * *